US011834652B2

(12) United States Patent
Acar et al.

(10) Patent No.: US 11,834,652 B2
(45) Date of Patent: Dec. 5, 2023

(54) COMPOSITIONS AND METHODS FOR SCARLESS GENOME EDITING

(71) Applicant: YALE UNIVERSITY, New Haven, CT (US)

(72) Inventors: Murat Acar, New Haven, CT (US); Gregory Elison, New Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 688 days.

(21) Appl. No.: 16/348,092

(22) PCT Filed: Nov. 8, 2017

(86) PCT No.: PCT/US2017/060557
§ 371 (c)(1),
(2) Date: May 7, 2019

(87) PCT Pub. No.: WO2018/089437
PCT Pub. Date: May 17, 2018

(65) Prior Publication Data
US 2019/0359972 A1    Nov. 28, 2019

Related U.S. Application Data

(60) Provisional application No. 62/419,161, filed on Nov. 8, 2016.

(51) Int. Cl.
| C12N 15/10 | (2006.01) |
| C12N 15/11 | (2006.01) |
| C12N 9/22 | (2006.01) |
| C12N 15/81 | (2006.01) |
| C12N 15/79 | (2006.01) |

(52) U.S. Cl.
CPC ............. *C12N 15/102* (2013.01); *C12N 9/22* (2013.01); *C12N 15/11* (2013.01); *C12N 15/81* (2013.01); *C12N 2310/20* (2017.05); *C12N 2800/80* (2013.01)

(58) Field of Classification Search
CPC ........ C12N 15/102; C12N 9/22; C12N 15/11; C12N 15/81
See application file for complete search history.

(56) References Cited

U.S. PATENT DOCUMENTS

2016/0024529 A1    1/2016    Carstens

FOREIGN PATENT DOCUMENTS

WO    2016089866 A1    6/2016

OTHER PUBLICATIONS

International Search Report and Written Opinion for PCT International Application No. PCT/US2017/060557 dated Feb. 1, 2018.
Acar, et al., "A general mechanism for network-dosage compensation in gene circuits", Science 329(5999), Sep. 2010, 1656-1660.
Acar, et al., "Enhancement of cellular memory by reducing stochastic transitions", Nature 435(7039), May 2005, 228-232 (abstract only).
Dicarlo, et al., "Genome engineering in *Saccharomyces cerevisiae* using CRISPR-Cas systems", Nucleic Acids Res. 41(7), Apr. 2013, 4336-4343.
Jinek, et al., "A programmable dual RNA-guided DNA endonuclease in adaptive bacterial immunity.", 2012, Science 337:816-821.
Yang, et al., "Optimization of scarless human stem cell genome editing", Nucleic Acids Res. 41(19), Oct. 2013, 9049-9061.

*Primary Examiner* — Marsha Tsay
(74) *Attorney, Agent, or Firm* — Saul Ewing LLP; Kathryn Doyle; Domingos J. Silva

(57) ABSTRACT

The present invention includes compositions and methods for promoting scarless genome editing in a cell. In one aspect, methods of the invention utilize the CRISPR/Cas9 system to introduce a cut site into a genomic location to be edited. In another aspect, methods of the invention integrate an edited sequence into that genomic location in a scarless manner.

11 Claims, 30 Drawing Sheets

Specification includes a Sequence Listing.

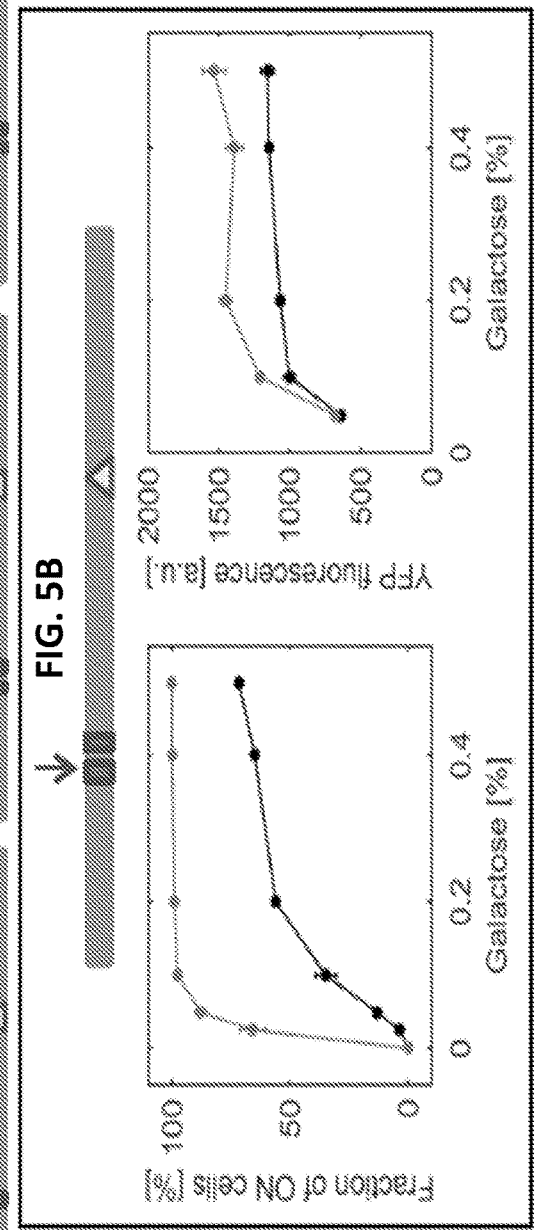
FIG. 5A
FIG. 5B
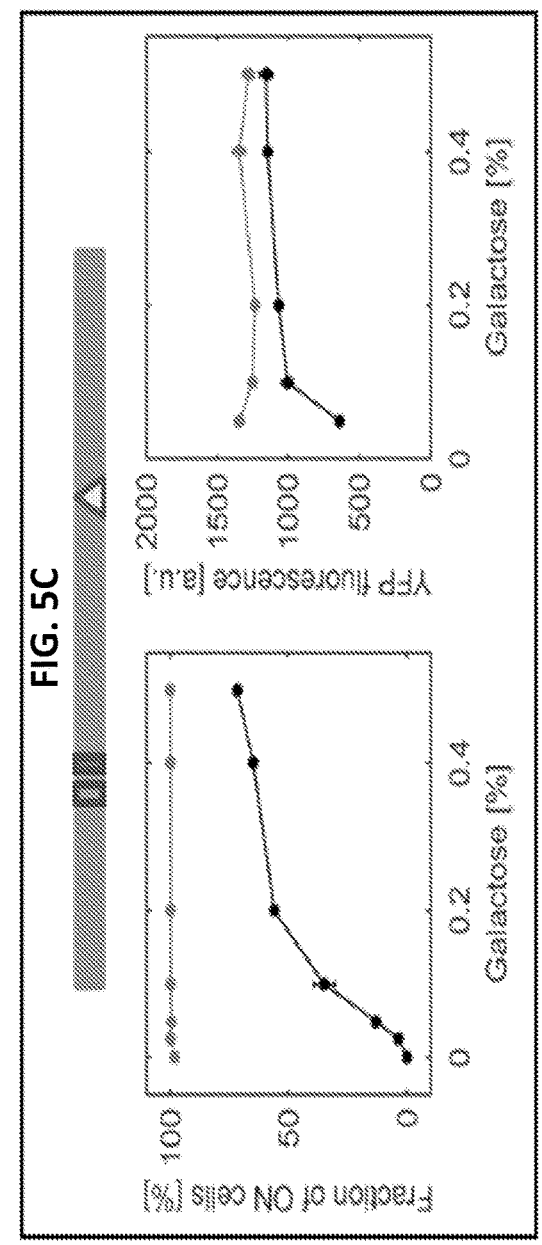
FIG. 5C

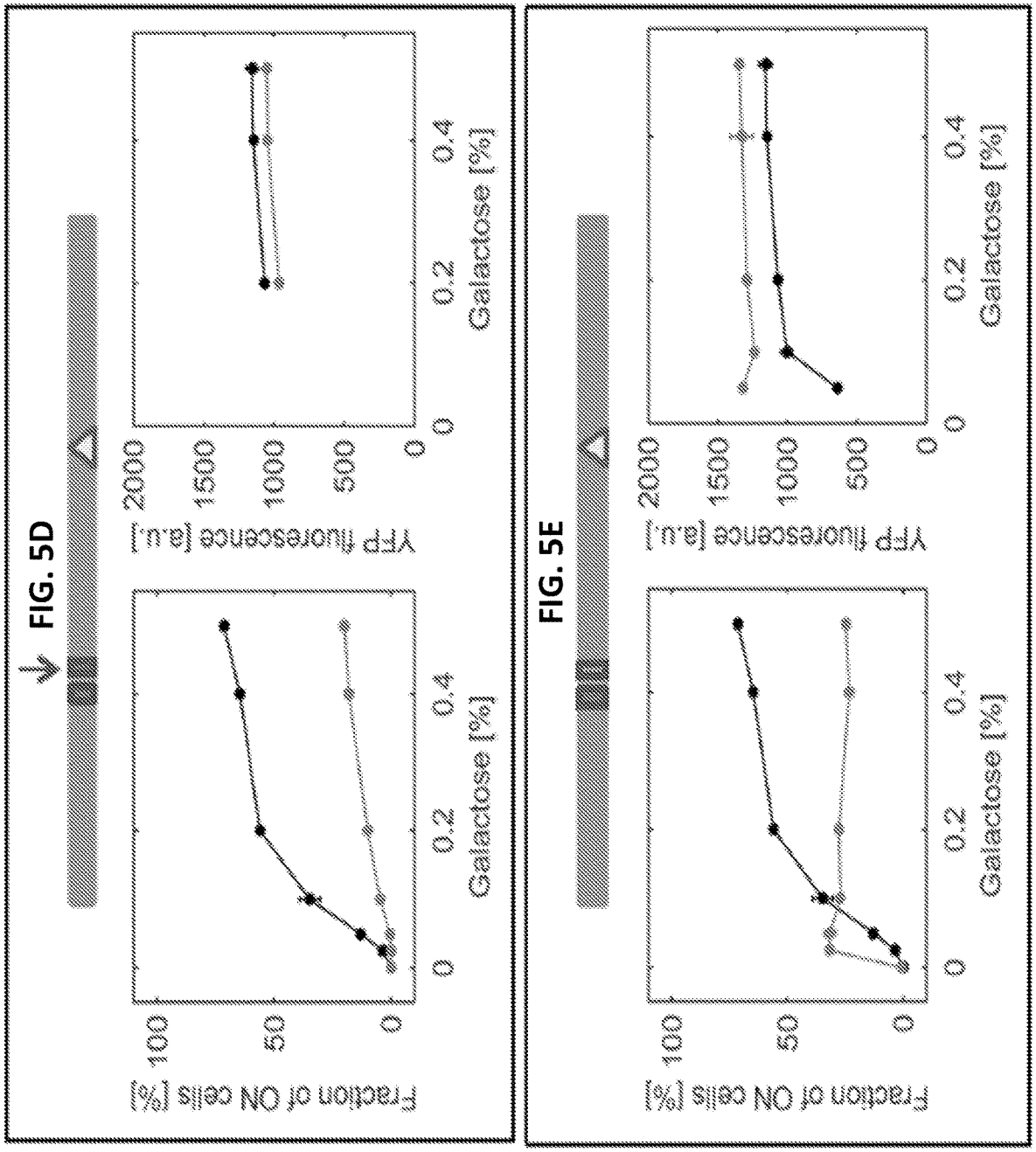

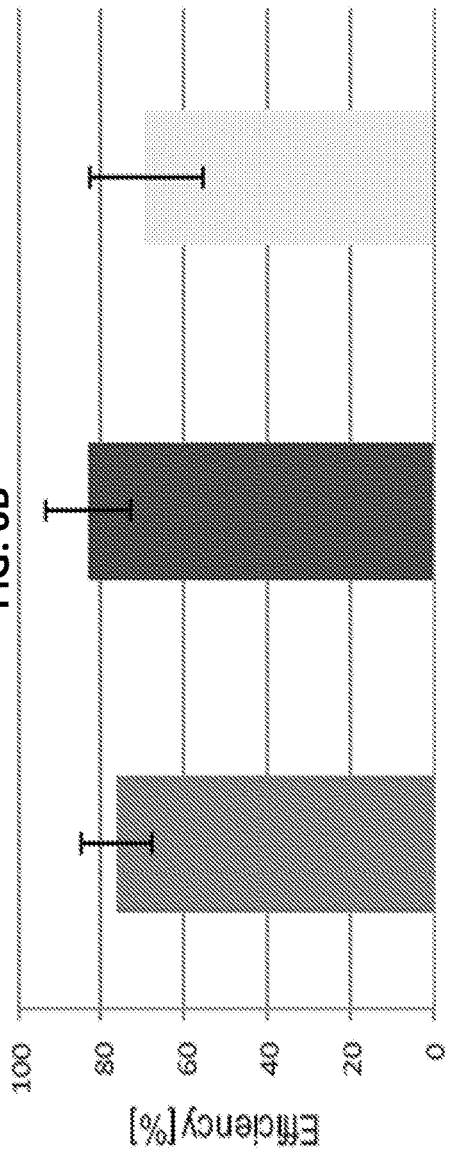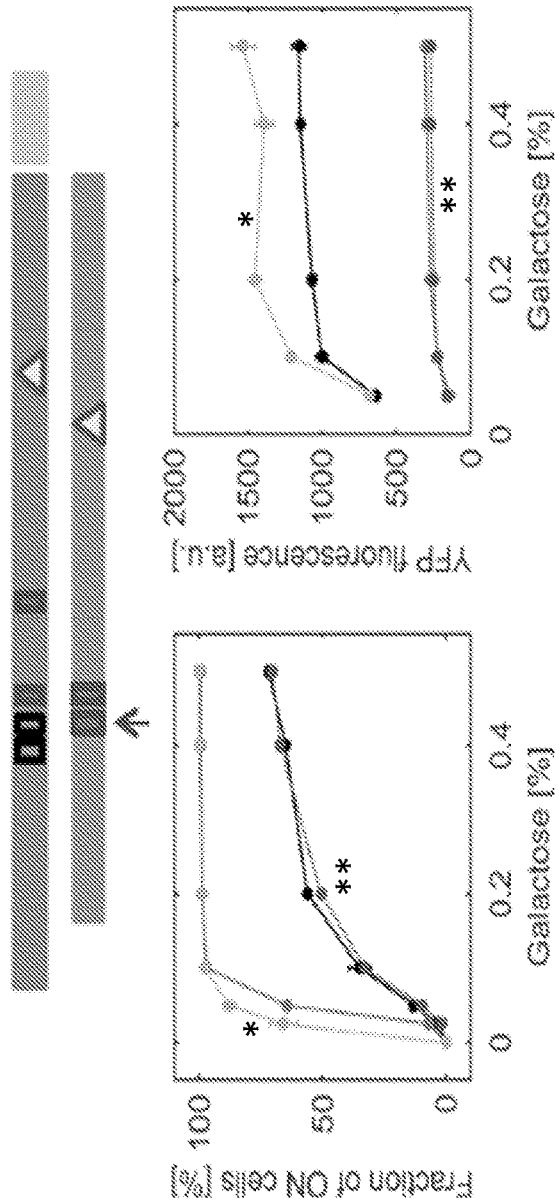

Left, Middle, and Right Canonical Gal4 Binding site Consensus Sequence: CGG...N₁₁...CCG Fourth Gal4 Noncanonical Binding site Sequence: CTCGC...N₁₁...CCGAACAAT Wild Type *GAL1* promoter sequence   (SEQ ID NO: 1)

ttatattgaatttcaaaattcttacttttttggatggacgcaaagaagtttaataatcatattac
atggcattaccaaccatatacatatccaatctactactagtgttgaaatgtaaagagcccca
ttatcttagcctaaaaaaccctctcttggaactttcagtaataacgcttaactgctcatgctatatg
aagtaagtcgcgtccctgaacgcagagtgtgctgcgtcctgt
cttcaccggtcgcgtcctgaacgcagagtgtgcaagatctac
aatactagctttatggtatgaagaaaatggcagtaacctggcccacaacttcaaattaac
gaatcaattaacaaccataggatgataatgcgattagttttttagccttatttctgggtaattaatca
gcgaagcgatgatttgaccattaacagataTATAAAtggaaaagctcataaagtatcaacaaaattgttaat
ctttcaacattcagttgtattactctattcaaatgtcataaaqtatcaacaaaattgttaat
atacctctatacttaacgtcaaggagagaaaaactata Wild Type *GAL80* promoter sequence   (SEQ ID NO: 2)

atggcgcaagtttccgctttgtaatatatatattataccctctctctcccctgcaatataagtt
taattctaattatattaatccatatatcctcttcattacaacgacctcaaa
atgtctgctacatccatcataaccaaagtccataactttttttgacctgaTATAtacattac
atatcactgctgtgcctgtccgaccagcgtaacatctgcgatagttggtttccgtcttccactccc
gtc

FIG. 7A

GE13: 1st Gal4 binding site removed (SEQ ID NO: 3)

ttatattgaatttcaaaaattcttacttcttttttggatggacgcaaagaagttaataatcatatattac
atggcattaccaccatatacacctaatcttactacttatatgttgaaatgtaaagagcccca
ttatcttagcctaaaaaacctctcttgaacttcagtaatacgcttaactgctcattgctatattg
aagtaagatgcgtcctcgtctcttcaccggtcgcgtc tgcgtcctcgtctcttcaccggtcgcgtc
ctgaaacgcagatgtgc aaagattctacaatactagctttatgg
ttatgaagaggaataattggcagtagttttttagcctagttttttagtcataacaacc
ataggatgataatgcgattagttttttagccttattctgggtaataacagcgagcgatgatttt
gatcattaacagataTATAAAtggaaaaagtgcataaaagtcatattaacatttcagt
ttgtattacttcttattcaaatgtcaaatgtcaatgtcaatgtcataatataccctctatactttaa
cgtcaaggagaaaaactata

GE15: 1st – 3rd Gal4 binding sites removed (SEQ ID NO: 4)

Ttatattgaatttcaaaaattcttacttcttttttggatggacgcaaagaagttaataatcatatattac
atggcattaccaccatatacacctaatcttactacttatatgttgaaatgtaaagagcccca
ttatcttagcctaaaaaacctctcttgaacttcagtaatacgcttaactgctcattgctatattg
aagtaagatgcgtcctcgtctcttcaccggtcgcgtcagtgcagaaaaaaatggcagtaacctggccc
aaagattctacaatactagctaaattaacgaatcaaatgaaataatgcgataatgcgataatgcgattaTATAAAtgaaaagctgc
cacaaaacctcaaattaacgaatcaaattaacgcgatgatttcagtttgtatctatatacctctactta
tttctgggtaataacagcgagcgatgatttttcagtttgtatctattaacagtttttagccta
ataaccacttaactaatatcaacatctcaactctcaagttcttattcaatgtcataaaagta
tcaacaaaaattgttaatataccctcttaacgtcaaggagaaaaactata

FIG. 7B

GE39: 1st Gal4 binding sites recoded (SEQ ID NO: 5)

ttatattgaatttcaaaattctactttttttggatggacgcaagaagttaatatcatattac
atgcattaccaccatatacatccaaaacctctctcttggaactttcagtaatacgctaattgctcattgctatattg
ttatcttagcctaaaaaacctctctcttggaactttcagtaatacgctaattgctcattgctatattg
aagtaTCTATTAGAAGCCGAAAagtgcgtcctcgt
cttcaccggtcgcgtcctgaaacgcagatgcgagatgtgcaaagattctac
aatactagctttatggttatgaagaaaaatggcagtaacctgccccaaacctcaattaac
gaatcaaattaacaaccatagagtaatgcgattagtttttagcctagttcctgggtaataatca
gcgaagcgatgattttgatctattaacagataTATAAAtgaatgaatgcataagaatatcaacaaaaatgttaat
atacctctatactttaacgtcaaggagaaaactata

GE40: 1st and 2nd Gal4 binding sites recoded (SEQ ID NO: 6)

ttatattgaatttcaaaattctactttttttggatggacgcaagaagttaatatcatattac
atgcattaccaccatatacatccaaaacctctctcttggaactttcagtaatacgctaattgctcattgctatattg
ttatcttagcctaaaaaacctctctcttggaactttcagtaatacgctaattgctcattgctatattg
aagtaTCTATTAGAAGCCGAAAagTTTGCGACAGCCCTTTAgcgtcctcgt
cttcaccggtcgcgtcctgaaacgcagatgcgagatgtgcaaagattctac
aatactagctttatggttatgaagaaaaatggcagtaacctgccccaaacctcaattaac
gaatcaaattaacaaccatagagtaatgcgattagtttttagcctagttcctgggtaataatca
gcgaagcgatgattttgatctattaacagataTATAAAtgaatgaatgcataaagtatcaacaaaaatgttaat
atacctctatactttaacgtcaaggagaaaactata

FIG. 7C

GE41: 1st – 3rd Gal4 binding sites recoded (SEQ ID NO: 7)

```
tt gaatttcaaaaattctactttttttggatggacgcaaagaagtttaataatcatattac
atggcattaccaccatacatcctaatcctacttatgtctgaatgtgaaagagccca
ttatctagcctaaaaaacctctcttggaacttcagtaatacgctcaactgctcattgctatattg
aagtaTCTATTAGAAGCCGAAAagTTTGCCGACAGCCCTTTTATAAAGACTCTCCTTATgcgtcctcgt
cttcaccggtcgcgttcctgaaacgcagatgtgcaaagattctac
aatactagctttatggttatgaagaggaaaaattggcagtaacctgcccacaacttcaaattaac
gaatcaaatttaacaaccatagatgaatgcgatatgtctattttagcctatttcgggtaataatca
gcgaaggagatgatcttcagtttgatctattaacagataTATATAAtggaaaagtcgataaccacttaactaata
cttcaacatttcagtttgatctattaacagataTATATAAtggaaaagtcgataaccacttaactaata
atacctctatacttaacgtcaaggagaaaaaactata
```

GE46: Extra Gal4 binding site added upstream of the existing site (SEQ ID NO: 8)

```
atggcgcaagtttccgcttgtaatatatatatatccctttcctctctcccctgcaatatatagtt
taattctaatattaatccctatatatatttctcattactaagacgactctata
aacgacctcaaaatgtctgcacatcacatgtcctgcacattcataataaccaaaagctcataacttttttga
acctgaaTATATAtacatcacatgtcctgcacattcataataaccaaaagctcataacttttttga
ttccgttcttccactcccgtc
```

GE47: Extra Gal4 binding site added downstream of the existing site (SEQ ID NO: 9)

```
atggcgcaagtttccgcttgtaatatatatatatccctttcctctctcccctgcaatatatagtt
taattctaatattaatccctatatatatttctcattacatcacatgtcctgcacattcataataaccaaaagctcataacttttttgaa
acctgaaTATATAacatcacatgtcctgcacattcataataaccaaaagctcataacttttttgaa
cctgaaTATATAtacatcacactgctgtacaatcacactgctgccgaccagcgtatacaatctcgatagttggt
ttccgttcttccactcccgtc
```

FIG. 7D

GE48: Gal4 binding site recoded upstream of the existing site (SEQ ID NO: 10)

```
atggcgaagttccgcttgtaatatatattatcctctctcccttccccgaatataatagtt
taattctacatatatatatatatatatatattaaccctctctctctccccgaataataatXXXXXXXXXX
atgtcgtgtacatcaataatacaagctcatactcttttgaacctgaaTATATacatcac
atcactgctgctgctgcgaccagcgtacaatcgatagtgttcccgttccttcccctccc
gtc
```

GE49: Gal4 binding site recoded downstream of the existing site (SEQ ID NO: 11)

```
atggcgaagttccgcttgtaatatatattatcctctctcccttccccgaatataatagtt
taattctacatatatatatatatattatttctctattccattaXXXXXXXXXX
atatcctgctgctgtcctgtaatattaccaagctcatactcttttgaacctgaaTATATacatcac
atcactgctgctgcgaccagcgtacaatcgatagtgttcccgttccttcccctccc
gtc
```

GE51: 2nd Gal4 binding site recoded (SEQ ID NO: 12)

```
tatatattgattccaaatttctactcttttttggatgactggaacgaagttaatcatcatac
atgccataccacatatatatcatcctattctatctattgtgttggaatgctaaagcccca
tctcttaagctaagcatccttcctcttcagtgactccagtcagtaacgcttactgctatatg
aagta[TTCCACCCTTT]AaagtcctcgtXXXXXXXXXX
cttcaccggtcgcgttcctgaacgcagtgtgcXXXXXXXXXX
aatactaaccaataggctgtatgaagaaaatggcatgtagttgXXXXXXXXXX
gatcaataaacaatccagttgtgattactacttaXXXXXXXXXX
gcgaagcatgatgttggatccttatcttgatctXXXXXXXXXX
cttcaccacatccagttgaggtcaagccttcXXXXXXXXXX
atacctatactcttaacgtcaaggagaaacctata
```

FIG. 7E

GE52: 3rd Gal4 binding site removed (SEQ ID NO: 13)

ttatattgatttcaaaaattcttacttttttttggatggacgcaaagaagttaataatcatattac
atggcattaccaccatatacattctaatatccatactattcttttgtgaaatgtaaagagccca
ttatcttagcctaaaaaacctctctcttggaactttcagtaatacgtcattgctctatattg
aagtagtcctcgtctcaccgtcgcgtc
ctgaaacgcagatgtgcagtaacgcagatgtgcaaatggcagtaacctggcccacaaacctggccccaaaacctggccccacaaacctg
ttatgaagaggaaaattggcagtaacctggcccacaaacctg
ataggatgatgattagtttttagccttagtttttagcctta
gatctataacagataTATAAAtggaaaagctgcataaagtgcataaagtgcataaagt
ttgtattactctattcaaatgtcataaagtgcataaagtgcata
cgtcaaggagagaaaaactata

GE53: 3rd Gal4 binding site recoded (SEQ ID NO: 14)

ttatattgatttcaaaaattcttacttttttttggatggacgcaaagaagttaataatcatattac
atggcattaccaccatatacattctaatatccatactattcttttgtgaaatgtaaagagccca
ttatcttagcctaaaaaacctctctcttggaactttcagtaatacgtcattgctctattg
aagtagtcctcgtctcaccgtcgcgtc ATAAAGACTCTCCTTAT gcgtcctcgt aagattctac
cttcaccgtcgcgtcctgaaacgcagatgtgca
aatactagtttatggttatgaagaggaaaaatggcagtaacctggcccaaacctggccccaaaccttcaaattaac
gaatcaaattaacaaccatagatgataatgcgattagttttttagccttatttagccttatttaggtaattaatca
gcgaagcagatgattttgatctattaacagataTATAAAtggaaaagctgcataaagtgcataaagtcattaactaata
ctttacaatttcagttgattacttctatttgattactttattcaaatgtcataaagtatcaacaaaaatgttaat
ataccctctatacctttaacgtcaaggagagaaaaactat

FIG. 7F

GE54: 1st and 3rd Gal4 binding sites removed (SEQ ID NO: 15)

ttatattgaatttcaaaaattcttacttttttggatggacgcaaagaagtttaatgatcatattac
atgcattaccaccatacacatatcctatcttactcttactatatgttgtgaaatgtaaagagcccca
ttatcttagcctaaaaaaccttctctttggaacttcagtaatacgctaactgtcattgctatattg
aagtaagatgcgtcctcgtctttcaccgtcgtgcgtcctgaaacgcagatgtgc
aagatctacaatactagcttatggttatgaagatgatgcga
tggcagtaacctgccccacaaacctggtttagcctatttctgggtaattaatcagcgagcgatgatttcatcttgtatctattaacagatat
ttagtttttagcctatttctgggtaattaatcagcgagcgatgatttcatcttgtatctattaacagatat
ATAAAtggaaaagctgcataaagtatcaacaaaaattgttgt
caaatgtcataaaatcaacaaaaattgttaatgtgaatgtttaaagttattaacgtcaaggagaaaaac
tata

GE55: 1st and 3rd Gal4 binding sites recoded (SEQ ID NO: 16)

ttatattgaatttcaaaaattcttacttttttggatggacgcaaagaagtttaatgatcatattac
atgcattaccaccatacacatatcctatcttactcttactatatgttgtgaaatgtaaagagcccca
ttatcttagcctaaaaaaccttctctttggaacttcagtaatacgctaactgtcattgctatattg
aagtaagTCTATTAGCGGAAagtgcctcgtctttcaccgtcgtgcgtcctgaaacgcagatgtgc
cttcaccggtcgtcgtgaaacgcagatgtgc
cttcaccggtcgtcgtgaaacgcagatgtgcATAAGACTCCTTATtgcgtcctcgt
aatactagctttatgttatgaagagaaaattggcagtaacctggccccacaaacctcaaattaac
gaatcaattaacaaccataggatgatagtcgatagttttagcctttatttctgggtaattaatca
gcgagcgatgatttcagttgtatctattaacagataTATAAAttcaatgtcataaaagtattaactaata
ctttcaacatttcagttgtatctattaacagataTATAAAttcaatgtcataaaagtattaactaata
atacctctatactttaacgtcaaggagaaaaactata

FIG. 7G

GE56: 2nd and 3rd Gal4 binding sites removed (SEQ ID NO: 17)

ttatattgaatttcaaaaattcttacttttttggatggacgcaaagaagttaataatcatattac
atggcattaccaccatatacatccatatctaatctactctacttatatgttgtggaaatgtaaagagcccca
ttatccttagcctaaaaaccttcagttctcttggaacttcagtaatacgtcacgcttatgtcacgctatattg
aagtgtgctcctcgtctcaccggtcgcgtcgcgaacgcagatgtgc
aagattctacaatactagcttttatggttatgcaacaacaggatgatgaatgcgat
ggcgagtaacctgcgcccacaactttcaaatcaaatttaacaggcgaaggtaagggaaggtaagggaagggatgaatt
tagttttttagccttattctgggtaatcaactcaacttcaacttcaacttaatcagcgaagcgatgatttttgatcttattaactactcttattc
TAAAtggaaaagtcataaaagtatcaacaacactttaatcaacaaaatgtcatcaacaacactttaatcaaaaaact
ata

GE57: 2nd and 3rd Gal4 binding sites recoded (SEQ ID NO: 18)

ttatattgaatttcaaaaattcttacttttttggatggacgcaaagaagttaataatcatattac
atggcattaccaccatatacatccatatctaatctactctacttatatgttgtggaaatgtaaagagcccca
ttatccttagcctaaaaaccttcagttctcttggaacttcagtaatacgtcacgcttatgtcacgctatattg
aagtaTTTGCGACAGCCTTTTAATAAAGACTCCTTATtgcgtcctcgt
cttcaccggtcgcgtcgcgaacgcagatgtgcaaagattctac
aatactagcttttatggttatgcaacaacaggatgatgaatgcgat
gaatcaaattaacaggcgaaggatgaatgcgatcaaattcatattcttaactatcaactttcatcaactttcatcaactttcatca
gcgaagcgatgatttttgatcttattaactactcttattcagttttgatctatattacttttcagttttgatcta
cttcaacattcttattactcttaacgtcaaggagaaaaaactata

FIG. 7H

GE60: Gal1: 1st and 2nd Gal4 binding sites recoded. Gal80: Gal4 binding site added upstream of existing site (SEQ ID NO: 19)

```
ttaattgaattcaaaaattcttacttttttggatggacgcaagaagtttaataatcatattac
atggcattaccaccatatacataaccatatctactactatgttgtggaaatgtaaagagcccca
ttatcttagctaaaatcctctcttgaactctactatacgctaactgtcattgtcatatatg
aagta[TCTATTAGAAGCCGAAA]agtTTTGCGACAGCCCTTTT]atgcgtccctcgt
cttcaccgtcgcgttcctgaaacgcagatgtgcgaaagatctac
aatactagtttatggttatgtgagaggaaaaatgcagtaacctggcccaaacctcaaattaac
gaatcaaattaacaatagaggataatgattaacagataTATAAtgaaaagtcataacaataa
gcgagcgatgatttcagttctattaacaacattttaatactactttaacgtcaaggagaaaaactata
ataccttctatactttaacgtcaaggagaaaaactata
```

```
atggcaagttttccgctttgtaatatatattatatttctctctccctgaatatagtt
taattctaataattaatatatcctataatatttctcattacta[aTATAA]atacaatagtt
aacgaccctcaaaatgtctgctacatcacactgctcacatattcatataaccaaaagctcatattctttttga
acctgaaTATATAtacatacataatgtctgctacatcacactgctcacatattcatataaccaaaagctcatataacaatctcgatagtgg
ttttcccgtctctttccactccgtc
```

Section II: gRNA cassette sequence (SEQ ID NO: 20)

```
tctttgaaagataaatgtatgattatgcttcactcattatacagaaactgatgtttcttcgag
tatatacaaggtgattacatgtacgttcgaagtacaactctagatttgtagtgccctcttggctagcg
gtaaagtggcgcaatttttcacactgacagtgtcctgtcaaagattttggtcaaacgctgtagagagt
gaaagttgtgcgatgttcggctgcatgttgttcggctgcatgttgttcggctgcatgttgNNNNNNNNNN
NNNNNNNNNNNNgtttagctagaaataaggctagtcgttatcaacttgaaaaagtg
gcaccgatcggtggtggtgctttttgttttttttatgtct
```

FIG. 7I

GE42: 4ᵗʰ Gal4 binding site removed (SEQ ID NO: 21)

```
ttatattgatttcaaaaattcttacttttttggatggacgcaaagaagttaataatcatattac
atggcattaccaccatatacataatccatatcttactcttactattcttggaatgtaaagagcccca
ttatcttagcctaaaaacctctcttggaactttcagtaatacgctaactgctcattgctctatatg
aagtat                  agtcgtcctcgt
cttcacggtcgcgttcctgaacgcagagatgtgcaaagatgtgaagatctacaatactagcttt atggttatgaag
aggaaaattggcagtaacctgcccccacaaactggcagtaaccctgcccccacaaatgatgatgatg
atactgattagttttagccttatttctgggtaattaatcactactttaactactttgatctatt
aacagataTATAAAtgaaaagctgcataaagtcataaatgtcataaatgtcataacatttcagtttgtatta
ctttcttattcaaatgtcataaaagtcataaatgtcataacattcaacaaaaatgttaatacttaacgtcaagg
agaaaaactata
```

GE43: 4ᵗʰ Gal4 binding site recoded (SEQ ID NO: 22)

```
ttatattgatttcaaaaattcttacttttttggatggacgcaaagaagttaataatcatattac
atggcattaccaccatatacataatccatatcttactcttactattcttggaatgtaaagagcccca
ttatcttagcctaaaaacctctcttggaactttcagtaatacgctaactgctcattgctctatatg
aagtat                  agtcgtcctcgt
cttcacggtcgcgttcctgaacgcagatgtgcCTCGCGCCACTGCTCCGAACAATaagattct
acaatactagcttttatggttatgaaggagagaaaattggcagtaacctgcccccacaaacctcaaatta
acgaataactaacaaccatagtgattagtttttagccttattctgggtaattaat
cagcgaagcgatgatttgatcattaacagataTATAAAtgaaaagctgcataaccacttaactaa
tactttcaacatttcagtttgtattacttcttattcaaatgtcataaaagtcataacattgtta
atacctctatactttaacgtcaaggagaaaaactata
```

FIG. 7J

GE66: 1$^{st}$ and 2$^{nd}$ Gal4 binding sites recoded. 5bp immediately downstream of 3$^{rd}$ Gal4 binding site moved immediately upstream of 1$^{st}$ Gal4 binding site    (SEQ ID NO: 23)

```
ttatattgaatttcaaaaattcttacttttttttgatgacgaagaagttaataatcatattac
atgcattaccaccatatatccatatcttacttatgttgtgaatgtaaagagcccca
ttatcttagcctaaaaaacctctcttcttgaacttcagtaatacgctaactgtcattgctctattg
aagta[tgcgt]g[TTCTATTAGAAGCCGAAA]a[gTTTGCGACAGCCCTTT]cctcgt
cttcacggtcgcgtcctgaaacgcagatgtgc                           aaagattctac
aatactagcttttatggttatgaagagaaaaattggcagtaacctgccccacaaacctcaaattaac
gaatcaaattaacaaccataggatgataatgcgattagttttttagccttatttctgggtaattaatca
gcgaagcgatgatttcagtctgatctattaacagataTATAAAtggaaaagctgcataaccacttaactaata
ctttcaacatttcagtttgtgttgtattacttcttcattcaaatgcataaagtatcaacaaaatgttaat
atacctctatacttaactgtcaaggagaaaaactata
```

GE67: 1$^{st}$ and 2$^{nd}$ Gal4 binding sites recoded. 10bp immediately downstream of 3$^{rd}$ Gal4 binding site moved immediately upstream of 1$^{st}$ Gal4 binding site    (SEQ ID NO: 24)

```
ttatattgaatttcaaaaattcttacttttttttgatgacgaagaagttaataatcatattac
atgcattaccaccatatatccatatcttacttatgttgtgaatgtaaagagcccca
ttatcttagcctaaaaaacctctcttcttgaacttcagtaatacgctaactgtcattgctctattg
aagta[tgcgtcctcg]g[TTCTATTAGAAGCCGAAA]a[gTTTGCGACAGCCCTTT]t
cttcacggtcgcgtcctgaaacgcagatgtgc                           aaagattctac
aatactagcttttatggttatgaagagaaaaattggcagtaacctgccccacaaacctcaaattaac
gaatcaaattaacaaccataggatgataatgcgattagttttttagccttatttctgggtaattaatca
gcgaagcgatgatttcagtctgatctattaacagataTATAAAtggaaaagctgcataaccacttaactaata
ctttcaacatttcagtttgtgttgtattacttcttcattcaaatgcataaagtatcaacaaaatgttaat
atacctctatacttaactgtcaaggagaaaaactata
```

FIG. 7K

GE68: 1st and 2nd Gal4 binding sites recoded. 17bp immediately downstream of 3rd Gal4 binding site moved immediately upstream of 1st Gal4 binding site    (SEQ ID NO: 25)

ttatattgatttcaagaattcttacttttttggatggacgcaagaagttaataatcatattac
atggcattaccaccatatacatatccatatcttactattatatgttgtgaaatgtaaagagcccca
ttatcttagcctaaaaaacctctctcttgaacttcagtaatacgctaactgctcattgctatattg
aagtatgcgtcctcgtcttcacTCTATTAGAAGCCCAAAagTTTGCGACAGCCCTTTTTa
cggtcgcgtcctgaaacgcagcagtgtgc         aagattc
tacatactagctttatgaagagagcaaaatggcagtaacctggcccacaaacctcaatt
aacgaatcaaattaacaaccataggatgataaatgcgattagttttttagcctatctctgggtaataa
tcagcgaagcgatgatttgatctcttattaacagataTATAAAtgaaaagctgcataaccacttaacta
atacttcaacatttcagtttgtattacttcttattcaaatgtcataaaagtatcaacaaaaatgtt
aatatacctctatacttaacgtcaaggagagaaaaactata First, Second, and Third canonical Gal4 binding site consensus sequence: CGG..N$_{11}$..CCG
(SEQ ID NO: 26)

Fourth non-canonical Gal4 binding site sequence: CTCGC..N$_{11}$..CCGAACAAT
(SEQ ID NO: 27)

FIG. 7L

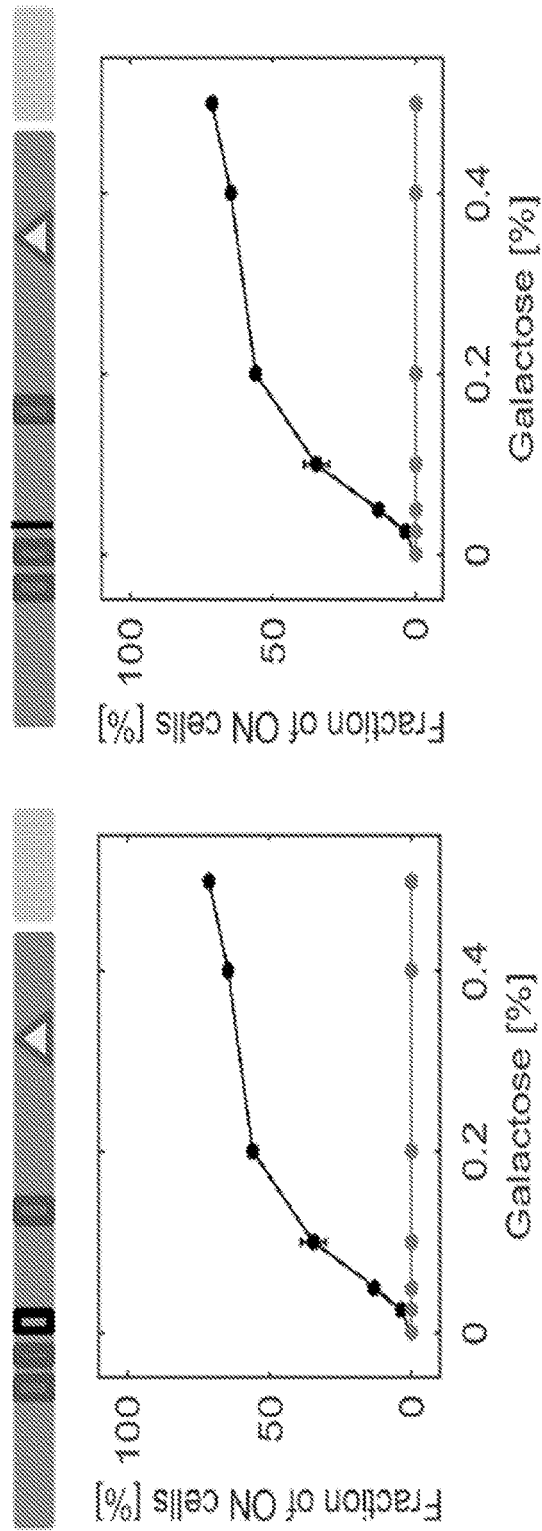
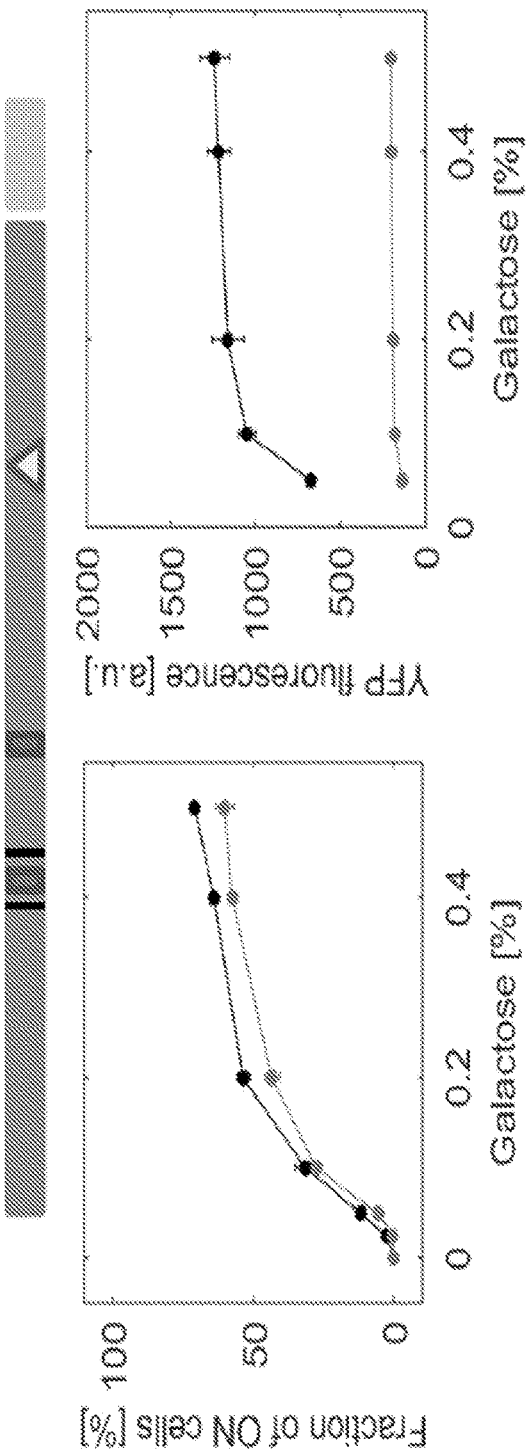
FIG. 8A  FIG. 8B  FIG. 8C

| Strain Name | Genetic Description |
|---|---|
| WP35 | Mata, ho::HIS5-P$_{GAL1}^{WT}$-YFP, P$_{GAL80}^{WT}$-GAL80 |
| GE1 | Mata, ho::HIS5-P$_{GAL1}^{WT}$-YFP, P$_{GAL80}^{WT}$-GAL80, trp1::TRP1-P$_{TEF1}$-CAS9 |
| GE13 | Mata, ho::HIS5-P$_{GAL1}^{13}$-YFP, P$_{GAL80}^{WT}$-GAL80, trp1::TRP1-P$_{TEF1}$-CAS9 |
| GE15 | Mata, ho::HIS5-P$_{GAL1}^{15}$-YFP, P$_{GAL80}^{WT}$-GAL80, trp1::TRP1-P$_{TEF1}$-CAS9 |
| GE39 | Mata, ho::HIS5-P$_{GAL1}^{39}$-YFP, P$_{GAL80}^{WT}$-GAL80, trp1::TRP1-P$_{TEF1}$-CAS9 |
| GE40 | Mata, ho::HIS5-P$_{GAL1}^{40}$-YFP, P$_{GAL80}^{WT}$-GAL80, trp1::TRP1-P$_{TEF1}$-CAS9 |
| GE41 | Mata, ho::HIS5-P$_{GAL1}^{41}$-YFP, P$_{GAL80}^{WT}$-GAL80, trp1::TRP1-P$_{TEF1}$-CAS9 |
| GE42 | Mata, ho::HIS5-P$_{GAL1}^{42}$-YFP, P$_{GAL80}^{WT}$-GAL80, trp1::TRP1-P$_{TEF1}$-CAS9 |
| GE43 | Mata, ho::HIS5-P$_{GAL1}^{43}$-YFP, P$_{GAL80}^{WT}$-GAL80, trp1::TRP1-P$_{TEF1}$-CAS9 |
| GE46 | Mata, ho::HIS5-P$_{GAL1}^{WT}$-YFP, P$_{GAL80}^{46}$-GAL80, trp1::TRP1-P$_{TEF1}$-CAS9 |
| GE47 | Mata, ho::HIS5-P$_{GAL1}^{WT}$-YFP, P$_{GAL80}^{47}$-GAL80, trp1::TRP1-P$_{TEF1}$-CAS9 |
| GE48 | Mata, ho::HIS5-P$_{GAL1}^{WT}$-YFP, P$_{GAL80}^{48}$-GAL80, trp1::TRP1-P$_{TEF1}$-CAS9 |
| GE49 | Mata, ho::HIS5-P$_{GAL1}^{WT}$-YFP, P$_{GAL80}^{49}$-GAL80, trp1::TRP1-P$_{TEF1}$-CAS9 |
| GE51 | Mata, ho::HIS5-P$_{GAL1}^{51}$-YFP, P$_{GAL80}^{WT}$-GAL80, trp1::TRP1-P$_{TEF1}$-CAS9 |
| GE52 | Mata, ho::HIS5-P$_{GAL1}^{52}$-YFP, P$_{GAL80}^{WT}$-GAL80, trp1::TRP1-P$_{TEF1}$-CAS9 |
| GE53 | Mata, ho::HIS5-P$_{GAL1}^{53}$-YFP, P$_{GAL80}^{WT}$-GAL80, trp1::TRP1-P$_{TEF1}$-CAS9 |
| GE54 | Mata, ho::HIS5-P$_{GAL1}^{54}$-YFP, P$_{GAL80}^{WT}$-GAL80, trp1::TRP1-P$_{TEF1}$-CAS9 |
| GE55 | Mata, ho::HIS5-P$_{GAL1}^{55}$-YFP, P$_{GAL80}^{WT}$-GAL80, trp1::TRP1-P$_{TEF1}$-CAS9 |
| GE56 | Mata, ho::HIS5-P$_{GAL1}^{56}$-YFP, P$_{GAL80}^{WT}$-GAL80, trp1::TRP1-P$_{TEF1}$-CAS9 |
| GE57 | Mata, ho::HIS5-P$_{GAL1}^{57}$-YFP, P$_{GAL80}^{WT}$-GAL80, trp1::TRP1-P$_{TEF1}$-CAS9 |
| GE60 | Mata, ho::HIS5-P$_{GAL1}^{WT}$-YFP, P$_{GAL80}^{60}$-GAL80, trp1::TRP1-P$_{TEF1}$-CAS9 |
| GE66 | Mata, ho::HIS5-P$_{GAL1}^{66}$-YFP, P$_{GAL80}^{WT}$-GAL80, trp1::TRP1-P$_{TEF1}$-CAS9 |
| GE67 | Mata, ho::HIS5-P$_{GAL1}^{67}$-YFP, P$_{GAL80}^{WT}$-GAL80, trp1::TRP1-P$_{TEF1}$-CAS9 |
| GE68 | Mata, ho::HIS5-P$_{GAL1}^{68}$-YFP, P$_{GAL80}^{WT}$-GAL80, trp1::TRP1-P$_{TEF1}$-CAS9 |

FIG. 9

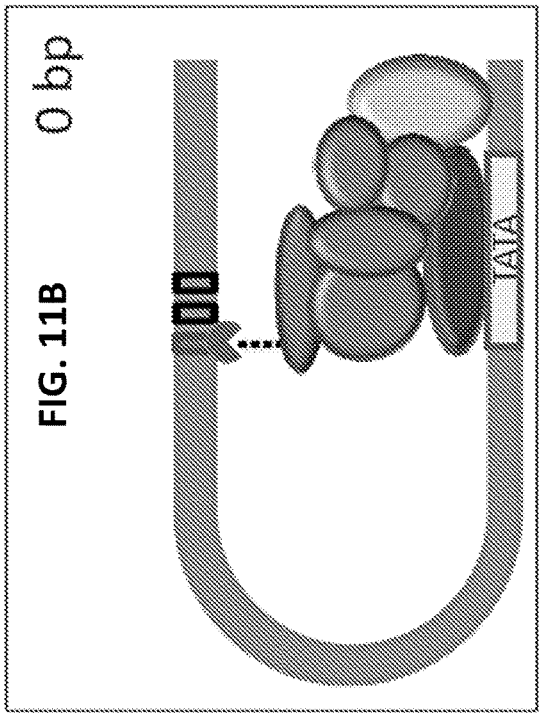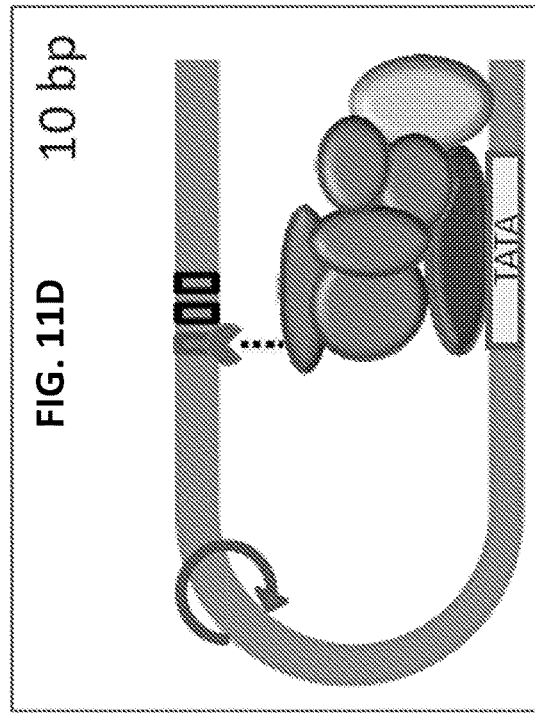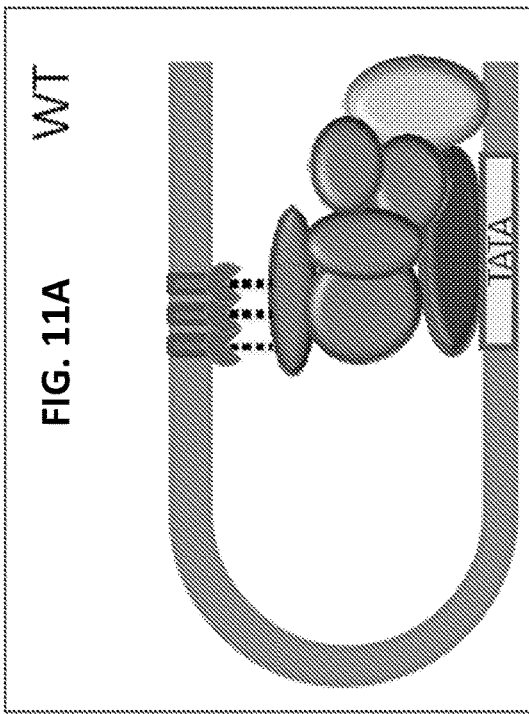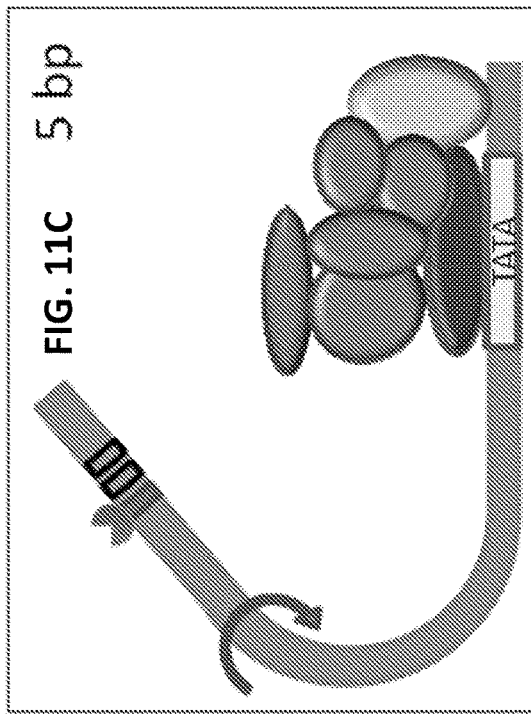

COMPOSITIONS AND METHODS FOR SCARLESS GENOME EDITING

CROSS-REFERENCE TO RELATED APPLICATIONS

The present application is a 35 U.S.C. § 371 national phase application from, and claims priority to, International Application No. PCT/US2017/060557, filed Nov. 8, 2017, and published under PCT Article 21(2) in English, which claims priority under 35 U.S.C. § 119(e) to U.S. Provisional Application No. 62/419,161, filed Nov. 8, 2016, each of which is incorporated herein by reference in its entirety.

STATEMENT REGARDING FEDERALLY SPONSORED RESEARCH OR DEVELOPMENT

This invention was made with government support under GM007499 and AG050461 awarded by National Institutes of Health. The government has certain rights in the invention.

BACKGROUND OF THE INVENTION

In the few years since its development, the CRISPR/Cas9 genome editing technique has been extensively used for the genetic modification of a large variety of organisms, including the budding yeast *S. cerevisiae*. However, while the technique has been remarkably successful, it still fails to afford completely scarless editing of the genome. For successful editing to take place, the final sequence must have either the protospacer adjacent motif (PAM) sequence or the targeting sequence altered. Recent papers and protocols acknowledge that they can only achieve scarlessness if the desired edit happens to disrupt the targeting or PAM sequence of the gRNA being used. This has not been a problem for most applications involving proteins, as these edits can be made in such a way as not to change the resulting polypeptide. However, when investigating less well defined genomic regions, such as promoters, where the effects of minor base pair changes are unknown, the current CRISPR/Cas9 genome editing techniques provide material of questionable quality.

There is thus a need in the art for a scarless version of the CRISPR genome editing technique, which introduces only desired edits with no unwanted changes across a fairly large region of DNA. The present invention addresses and satisfies this need.

SUMMARY OF THE INVENTION

As described herein, the present invention relates in certain aspects to compositions and methods for scarless genome editing.

In one aspect, the invention provides a method of performing scarless genome editing in a cell comprising a cell genome. In certain embodiments, the method comprises introducing into the cell Cas9 or a variant thereof, a first guide RNA (gRNA), a second gRNA, and a first polynucleotide. In certain embodiments, the first gRNA comprises a nucleotide sequence that is complementary to a cell genome sequence that is upstream of a first genomic region of interest. In certain embodiments, the second gRNA comprises a nucleotide sequence that is complementary to a cell genome sequence that is downstream of the first genomic region of interest. In certain embodiments, the first polynucleotide comprises a nucleotide sequence that is homologous to a cell genome sequence upstream and adjacent to the nucleotide sequence targeted by the first gRNA, a nucleotide sequence comprising a given CRISPR cut site, and a nucleotide sequence that is homologous to a cell genome sequence downstream and adjacent to the nucleotide sequence targeted by the second gRNA. In certain embodiments, the first genomic region of interest is excised from the cell genome and replaced in the cell genome with the first polynucleotide. In certain embodiments, Cas9 or a variant thereof, a third gRNA, and a second polynucleotide are introduced into the cell. In certain embodiments, the third gRNA comprises a nucleotide sequence that is complementary to the first polynucleotide. In certain embodiments, the second polynucleotide comprises a nucleotide sequence that is homologous to a cell genome sequence upstream and adjacent to the first polynucleotide, a nucleotide sequence that is a second genomic region of interest, and a nucleotide sequence that is homologous to a cell genome sequence downstream and adjacent to the first polynucleotide. In certain embodiments, the first polynucleotide is excised from the cell genome and replaced in the cell genome with the second polynucleotide.

In another aspect the invention includes a scarless genome editing system comprising Cas9 or a variant thereof, a first guide RNA (gRNA), a second gRNA, a third gRNA, a first polynucleotide, and a second polynucleotide, for performing scarless genome editing in a cell comprising a cell genome, wherein a first genomic region of interest is replaced in the cell genome with a second genomic region of interest. In certain embodiments, the first gRNA comprises a nucleotide sequence that is complementary to a cell genome sequence that is upstream of the first genomic region of interest. In certain embodiments, the second gRNA comprises a nucleotide sequence that is complementary to a cell genome sequence that is downstream of the first genomic region of interest. In certain embodiments, the first polynucleotide comprises a nucleotide sequence that is homologous to a cell genome sequence that is upstream and adjacent to the nucleotide sequence targeted by the first gRNA, a nucleotide sequence comprising a given CRISPR cut site, and a nucleotide sequence that is homologous to a cell genome sequence that is downstream and adjacent to the nucleotide sequence targeted by the second gRNA. In certain embodiments, the third gRNA comprises a nucleotide sequence that is complementary to the first polynucleotide. In certain embodiments, the second polynucleotide comprises a nucleotide sequence that is homologous to a cell genome sequence that is upstream and adjacent to the first polynucleotide, a nucleotide sequence that is a second genomic region of interest, and a nucleotide sequence that is homologous to a cell genome sequence downstream and adjacent to the first polynucleotide.

In various embodiments of the above aspects or any other aspect of the invention delineated herein, the first genomic region of interest comprises a promoter sequence. In certain embodiments, the first genomic region of interest comprises a non-coding sequence. In certain embodiments, the first genomic region of interest comprises a coding sequence. In certain embodiments, the first genomic region of interest comprises a DNA sequence. In certain embodiments, the first genomic region of interest comprises an RNA sequence.

In certain embodiments, the nucleotide sequence comprising a given CRISPR cut site comprises a protospacer adjacent motif (PAM) sequence. In certain embodiments, the PAM sequence comprises 5'-NGG-3'.

In certain embodiments, the cell is a eukaryotic cell. In certain embodiments, the cell is a prokaryotic cell. In certain embodiments, the cell is a plant cell. In certain embodiments, the cell is a fungal cell. In certain embodiments, the cell is a metazoan cell. In certain embodiments, the eukaryotic cell is a mammalian cell. In certain embodiments, the eukaryotic cell is a human cell. In certain embodiments, the eukaryotic cell is a yeast cell.

In certain embodiments, the method is multiplexed by editing at least one additional genomic region of interest. In certain embodiments, the scarless genome editing system is multiplexed. In certain embodiments, at least two different genomic regions are edited simultaneously. In certain embodiments, at least two different genomic regions are edited sequentially in time. In certain embodiments, at least two different genomic regions are edited separately in time.

In certain embodiments, the method further comprises editing a third genomic region of interest comprising introducing into the cell Cas9 or a variant thereof, a fourth guide RNA (gRNA), a fifth gRNA, and a third polynucleotide. In certain embodiments, the fourth gRNA comprises a nucleotide sequence that is complementary to a cell genome sequence that is upstream of the third genomic region of interest. In certain embodiments, the fifth gRNA comprises a nucleotide sequence that is complementary to a cell genome sequence that is downstream of the third genomic region of interest. In certain embodiments, the third polynucleotide comprises a nucleotide sequence that is homologous to a cell genome sequence upstream and adjacent to the nucleotide sequence targeted by the fourth gRNA, a nucleotide sequence comprising a given CRISPR cut site, and a nucleotide sequence that is homologous to a cell genome sequence downstream and adjacent to the nucleotide sequence targeted by the fifth gRNA. In certain embodiments, the third genomic region of interest is excised from the cell genome and replaced in the cell genome with the third polynucleotide. In certain embodiments, Cas9 or a variant thereof, a sixth gRNA, and a fourth polynucleotide are introduced into the cell. In certain embodiments, the sixth gRNA comprises a nucleotide sequence that is complementary to the third polynucleotide. In certain embodiments, the fourth polynucleotide comprises a nucleotide sequence that is homologous to a cell genome sequence upstream and adjacent to the third polynucleotide, a nucleotide sequence that is a fourth genomic region of interest, and a nucleotide sequence that is homologous to a cell genome sequence downstream and adjacent to the third polynucleotide. In certain embodiments, the third polynucleotide is excised from the cell genome and replaced in the cell genome with the fourth polynucleotide.

BRIEF DESCRIPTION OF THE DRAWINGS

The following detailed description of specific embodiments of the invention will be better understood when read in conjunction with the appended drawings. For the purpose of illustrating the invention, exemplary embodiments are shown in the drawings. It should be understood, however, that the invention is not limited to the precise arrangements and instrumentalities of the embodiments shown in the drawings.

FIG. 1A shows the introduction of a novel CRISPR cut site to the GAL1 promoter of the $P_{GAL1}$-YFP construct integrated in the ho locus of the yeast genome. $P_{GAL1}$ is flanked by the YFP gene downstream and genomic DNA upstream. Two gRNA/Cas9 complexes target cut sites immediately adjacent to $P_{GAL1}$ resulting in its loss from the genome. The addition of a donor oligonucleotide with a novel CRISPR cut site flanked by regions of homology to the upstream genome and YFP allows repair. The repair results in a new region in which the old cut sites have been removed and a novel one is inserted. FIG. 1B shows introduction of an edited $P_{GAL1}$ oligonucleotide back to the original location. The novel CRISPR cut site is cut by a gRNA/Cas9 complex. Repair is facilitated by the addition of a donor oligonucleotide consisting of an edited $P_{GAL1}$ and homology to the upstream genome and YFP. The repair gives rise to an edited $P_{GAL1}$ upstream of YFP. FIG. 1C shows the efficiency of CRISPR editing. Of the colonies tested for CRISPR editing, 63% contained the correct sequence after the first stage of editing for $P_{GAL80}$, and 77% contained the correct sequence after the second stage of editing for $P_{GAL1}$. Error bars indicate SEM (N=2 for stage one; N=3 for stage two).

FIG. 2A shows relevant components of the yeast GAL network. GAL4 is constitutively expressed and activates $P_{GAL80}$ and $P_{GAL1}$. GAL80 inhibits the activity of GAL4, thus inhibiting both its own and $P_{GAL1}$ expression. FIG. 2B shows the architecture of the GAL1 promoter. The first line represents the wild type GAL1 promoter. The boxes are Gal4 binding sites and the triangle is the TATA box. The second line represents a GAL1 promoter in which the first Gal4 binding site has been recoded (empty box). The third line represents a GAL1 promoter in which the first Gal4 binding site has been removed entirely (black line), shortening the length of the promoter by 17 bp. FIG. 2C shows phenotypic characterization of wild type $P_{GAL1}$-YFP activity. The bar at the top indicates that the data refers to the wild type architecture of the GAL1 promoter. The seven histograms show the flow cytometry data at seven concentrations of galactose as indicated from 0% to 0.5%. The top right panel shows the fraction of ON cells as galactose concentration increases and the bottom right panel shows the mean expression level of the ON state for concentrations with at last 5% ON cells. Error bars indicate SEM (N=3). FIG. 2D shows the phenotypic characterization of an edited GAL1 promoter used in $P_{GAL1}$-YFP. The bar at the top indicates that the data refers to an edited GAL1 promoter with the first and second Gal4 binding sites recoded. The top and bottom right panels show the fraction of ON cells and mean ON expression levels, respectively, as galactose concentration increases (grey). The data from the wild type GAL1 promoter (black) were included for comparison purposes. The mean ON expression level plots only include galactose concentrations at which both strains have at least 5% ON cells. Error bars indicate SEM (N=3).

In FIGS. 3A-3D, wild type data are plotted in black as the reference while the data of each bar-illustrated strain are shown in grey. Each panel depicts either the fraction of ON cells in percent or the mean expression level of the ON cell in arbitrary units (a.u.). The mean ON expression level plots only include galactose concentrations at which both strains plotted have at least 5% ON cells. Error bars indicate SEM (N=3).

In FIGS. 4A-4B, wild type data are plotted in black as the reference while the data of each bar-illustrated strain are shown in grey. Each panel depicts either the fraction of ON cells in percent or the mean expression level of the ON cells in arbitrary units (a.u.), reported by the edited $P_{GAL1}$-YFP. Error bars indicate SEM (N=2).

FIGS. 5A-5E are a series of graphs and images showing editing of the GAL80 promoter and phenotypic characterizations. FIG. 5A illustrates promoter elements and edits on the GAL80 promoter. The first depicts the wild type GAL80 promoter with a single Gal4 binding site (box) and a TATA box (triangle). The second shows a second Gal4 binding site (arrow) inserted before the original site. The third has a recoded Gal4 binding site (empty box) before the original site. For FIGS. 5B-5E, each horizontal bar indicates one strain and illustrates the specific edits introduced in the GAL80 promoter. The filled boxes are Gal4 binding sites while recoding an existing sequence to a Gal4 binding site is depicted by an empty box. A pointing arrow indicates the second Gal4 binding site inserted. The wild type data are plotted in black as the reference while the data of each bar-illustrated strain are shown in grey. Each panel depicts either the fraction of ON cells in percent or the mean expression level of the ON cells in arbitrary units (a.u.), reported by the unedited $P_{GAL1}$-YFP. The mean ON expression level plots only include galactose concentrations at which both strains plotted have at least 5% ON cells. Error bars indicate SEM (N=3).

FIGS. 6A-6C are a series of graphs and images illustrating introduction of simultaneous edits into the GAL1 and GAL80 promoters. FIG. 6A is a cartoon diagram showing the two-step CRISPR editing technique. The second step of the technique introduces two edited sequences (GAL1 and GAL80 promoters) simultaneously. FIG. 6B shows the editing efficiency for the second step of the technique. 76% of the colonies had the correct GAL1 promoter edits, 83% had the correct GAL80 promoter edits, and 69% were correct for both GAL1 and GAL80 promoters. Error bars indicate SEM (N=3). FIG. 6C shows phenotypic characterization of the strain carrying the dual promoter edits. Each horizontal bar indicates the GAL1 (top) or GAL80 (bottom) promoter and illustrates the specific edits introduced in them. The filled boxes are Gal4 binding sites while recoding an existing sequence to a Gal4 binding site is depicted by an empty box. An empty box shows recoding a previously existing Gal4 binding site to a null sequence with the same length. A triangle indicates the TATA box. The wild type data is plotted in black as the reference while the data from the dual-bar-illustrated edited strain are shown in grey. The left and right panel depicts, respectively, the fraction of ON cells in percent or the mean expression level of the ON cells in arbitrary units (a.u.), reported by the edited $P_{GAL1}$-YFP. Data points labeled (*) and (**) show the phenotypic levels measured from a strain carrying the same edits but only on the GAL1 (GAL80) promoter, not both. The mean ON expression level plot only includes galactose concentrations at which all strains plotted have at least 5% ON cells. Error bars indicate SEM (N=3).

FIGS. 7A-7L show exemplary promoter sequences (SEQ ID NOs: 1-27) used in the study. Gal4 binding sites are highlighted in black. Recoded Gal4 binding sites are boxed. The TATA box is highlighted in grey.

FIGS. 8A-8C are a set of graphs and images showing further editing of the canonical Gal4 binding sites on the GAL1 promoter. Each horizontal bar indicates one strain and illustrates the specific edits introduced in the GAL1 promoter. The filled boxes are Gal4 binding sites while removing a Gal4 binding site by recoding is depicted by an empty box. A triangle indicates the TATA box and the black line indicates the removal of a Gal4 binding site. In FIGS. 8A-8C, wild type data are plotted in black as the reference while the data of each bar-illustrated strain are shown in grey. Each panel depicts either the fraction of ON cells in percent or the mean expression level of the ON cell in arbitrary units (a.u.). The mean ON expression level plot only includes galactose concentrations at which both strains plotted have at least 5% ON cells. Error bars indicate SEM (N=3).

FIG. 9 is a table showing exemplary yeast strains constructed in the present study. All strains are derived from a blank W303 strain and contain the edits shown herein. The superscript number after a promoter indicates that the promoter has been edited and references the number of the edited strain in question. Specific strains are depicted herein. A 'WT' indicates that the promoter has not been edited for the strain in question.

FIG. 10A depicts a strain with first and second Gal4 binding sites recoded. This is the parent of the three strains (carrying specific spacing changes) whose phenotypes displayed in the remaining panels of this figure. FIG. 10B depicts a strain with the 5 bp sequence immediately downstream of the third Gal4 binding site moved immediately upstream of the first Gal4 binding site. FIG. 10C depicts a strain with the 10 bp sequence immediately downstream of the third Gal4 binding site moved immediately upstream of the first Gal4 binding site. FIG. 10D depicts a strain with the 17 bp sequence immediately downstream of the third Gal4 binding site moved immediately upstream of the first Gal4 binding site.

FIGS. 11A-11D are a series of images that model incorporating distance-based factors influencing GAL1 promoter activity. The filled boxes are Gal4 binding sites while removing a Gal4 binding site by recoding is depicted by an empty box. The TATA box is also depicted. Gal4 proteins are depicted by pacman symbols. TATA binding protein is shown above the TATA box. DNA polymerase is depicted as the light grey oval on the right side of each drawing. Mediator proteins are shown in grey. Black dotted lines indicate interactions between Gal4 proteins and the mediator complex. Arrows indicate the turn of the DNA helix. FIG. 11A is a schematic of the wild type GAL1 promoter. FIG. 11B is a schematic of the promoter architecture present in the parent strain from which the three strains carrying three spacing changes were constructed. The first and second Gal4 binding sites have been recoded. FIG. 11C is a schematic of the promoter having the third Gal4 binding site move 5 bp towards the TSS and TATA box (rotated nearly half circle around the DNA helix). FIG. 11D is a schematic of the promoter having the third Gal4 binding site move 10 bp towards the TSS and TATA box (rotated almost one full circle around the DNA helix).

FIG. 13A shows strains in which the first three Gal4 binding sites in the GAL1 promoter have been removed (left panel) and recoded (right panel). Strain data error bars indicate SEM (N=3). FIG. 13 shows a strain in which the fourth Gal4 binding site has been removed. Strain data error bars indicate SEM (N=2). FIG. 13C shows a strain in which the fourth Gal4 binding site has been recoded. Strain data error bars indicate SEM (N=2).

DETAILED DESCRIPTION OF THE INVENTION

Definitions

Figure 1A:
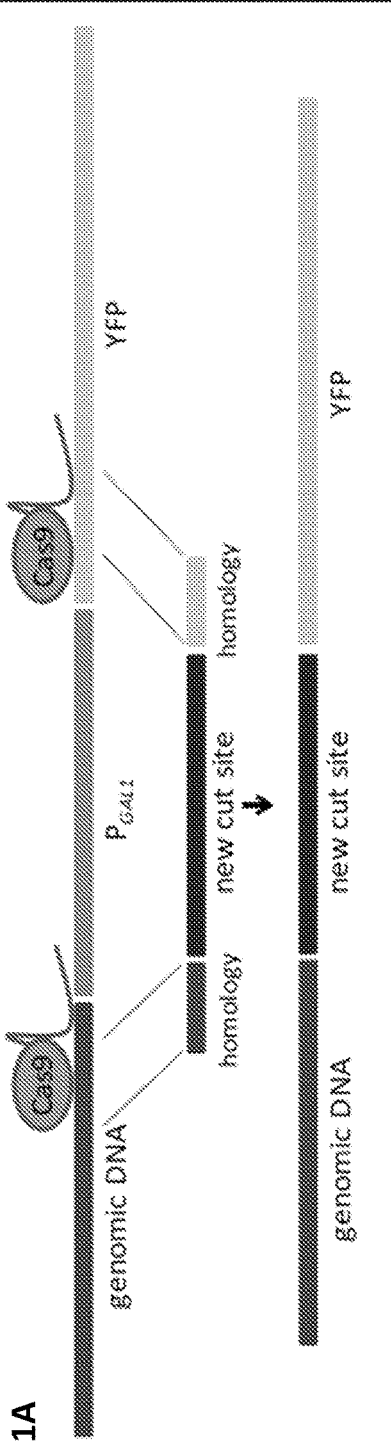
FIGS. 1A-1C are a series of images and a graph illustrating an exemplary two-step CRISPR editing method of the invention.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, exemplary materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein the term "amount" refers to the abundance or quantity of a constituent in a mixture.

As used herein, the term "bp" refers to base pair.

The term "complementary" refers to the degree of antiparallel alignment between two nucleic acid strands. Complete complementarity requires that each nucleotide be across from its opposite. No complementarity requires that each nucleotide is not across from its opposite. The degree of complementarity determines the stability of the sequences to be together or anneal/hybridize. Furthermore various DNA repair functions as well as regulatory functions are based on base pair complementarity.

The term "CRISPR/Cas" or "clustered regularly interspaced short palindromic repeats" or "CRISPR" refers to DNA loci containing short repetitions of base sequences followed by short segments of spacer DNA from previous exposures to a virus or plasmid. Bacteria and archaea have evolved adaptive immune defenses termed CRISR/CRISPR-associated (Cas) systems that use short RNA to direct degradation of foreign nucleic acids. In bacteria, the CRISPR system provides acquired immunity against invading foreign DNA via RNA-guided DNA cleavage.

The "CRISPR/Cas9" system or "CRISPR/Cas9-mediated gene editing" refers to a type II CRISPR/Cas system that has been modified for genome editing/engineering. It is typically comprised of a "guide" RNA (gRNA) and a non-specific CRISPR-associated endonuclease (Cas9). "Guide RNA (gRNA)" is used interchangeably herein with "short guide RNA (sgRNA)". The gRNA is a short synthetic RNA composed of a "scaffold" sequence necessary for Cas9-binding and a user-defined ~20 nucleotide "spacer" or "targeting" sequence which defines the genomic target to be modified. The genomic target of Cas9 can be changed by changing the targeting sequence present in the gRNA. "Cas9" should be interpreted to include any and all types and/or variants of Cas9. Examples of Cas9 variants include but are not limited to Cas9-nickase (Cas9n), nuclease dead Cas9 (dCas9) fused to the non-specific endonuclease FokI (dCas9-FokI), "enhanced Cas9", "high-fidelity Cas9", eSpCas9, spCas9-HF1, HypaCas9, S. pyogenes VQR, EQR and VRER mutants, "non-Sp" Cas9s, and full-nuclease variants.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

As used herein, "genome editing" refers to any modification or alteration of a genome, including but not limited to editing nucleotide sequences, deleting nucleotide(s), or adding nucleotide(s). After genome editing has been performed, the number of nucleotides can be kept the same but changed in type/order, or the number of nucleotides may change. Genome editing can be performed on chromosomal, mobile, or synthetic forms of DNA or RNA.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

By the term "modified" as used herein, is meant a changed state or structure of a molecule or cell of the invention. Molecules may be modified in many ways, including chemically, structurally, and functionally. Cells may be modified through the introduction of nucleic acids.

A "mutation" as used therein is a change in a DNA sequence resulting in an alteration from a given reference sequence (which may be, for example, an earlier collected DNA sample from the same subject). The mutation can comprise deletion and/or insertion and/or duplication and/or substitution of at least one deoxyribonucleic acid base such as a purine (adenine and/or thymine) and/or a pyrimidine (guanine and/or cytosine). Mutations may or may not produce discernible changes in the observable characteristics (phenotype) of an organism (subject).

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). Likewise the term "nucleotide sequence" is meant to include RNA and/or DNA.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T".

"PAM" and "protospacer adjacent motif" are used interchangably herein, and refer to a DNA sequence following the DNA sequence targeted by the Cas9 nuclease in the CRISPR/Cas9 system which is frequently, though non-exclusively, 2-6 base pairs in length. In one non-limiting example, the PAM comprises the sequence 5'-NGG-3'. In certain embodiments, the PAM site may also be considered a 'landing pad' for Cas9 enzyme.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "polynucleotide" includes DNA, cDNA, RNA, DNA/RNA hybrid, antisense RNA, siRNA, miRNA, snoRNA, genomic DNA, synthetic forms, and mixed polymers, both sense and antisense strands, and may be chemically or biochemically modified to contain non-natural or derivatized, synthetic, or semisynthetic nucleotide bases. Also, included within the scope of the invention are alterations of a wild type or synthetic gene, including but not limited to deletion, insertion, substitution of one or more nucleotides, or fusion to other polynucleotide sequences.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

A "primer" is an oligonucleotide, usually of about 15, 20, 25, 30, 35, 40, 45 or 50 nucleotides in length, that is capable of hybridizing in a sequence specific fashion to the target sequence and being extended during the PCR.

The term "promoter" as used herein is defined as a DNA sequence recognized by the synthetic machinery of the cell, or introduced synthetic machinery, required to initiate the specific transcription of a polynucleotide sequence.

A "sample" or "biological sample" as used herein means a biological material from a subject, including but is not limited to organ, tissue, exosome, blood, plasma, saliva, urine and other body fluid. A sample can be any source of material obtained from a subject.

The term "scarless" as used herein refers to the absence of scarring, i.e. unintended deletions, insertions or mutations, in nucleotide bases following genome editing. An unscarred genome would be one in which no deletions, insertions or mutations other than those intentionally created are present. Scarring can occur, for example, after cleavage of DNA that generates blunt ends. Likewise, "scarless genome editing" refers to the process of genome editing wherein no scarring of the genome occurs.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

A "target site" or "target sequence" refers to a genomic nucleic acid sequence that defines a portion of a nucleic acid to which a binding molecule may specifically bind under conditions sufficient for binding to occur.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention provides novel CRISPR genome editing techniques that allow modification of genomic regions with no undesired base pair changes. In the compositions and methods described herein, CRISPR/Cas9 is utilized to create double strand breaks flanking a region of interest, in order to completely remove it from the genome and introduce a novel targeting sequence and PAM site in its place. This new site is then cut in a second round of editing, in which the original region is reintroduced along with any desired modifications. This two-step editing method allows any desired edits to be introduced across the genomic region in question, while maintaining all other base pairs as they are in the parent strain. In addition, once the intermediate strain is created, it may be reused indefinitely, thus every subsequent new edit to the same genomic region only requires one transformation instead of two.

In a non-limiting example, an illustrative method of the present invention was used as described herein for the in vivo editing of the canonical GAL1 promoter in yeast. The Gal4 binding sites from the promoter were systematically removed or recoded in order to study the phenotypic consequences of these changes at the single cell level. The activity from the edited promoter architectures was compared to the bimodal activity profile of the wild type GAL1 promoter, and deviations from the wild type behavior were analyzed in terms of the fraction of ON cells and the expression level of the ON state. It was discovered that the fourth binding site does not have any effect on transcriptional activity. Removing or recoding the first site prevented any activity from the promoter despite the presence of the second and third binding sites. Surprisingly, however, further removing the third Gal4 binding site (together with the first one) partially restored the wild type activity in the GAL1 promoter. Using the method described herein to edit the GAL80 promoter, analyzing the activity of the edited GAL80 promoter architectures, and interpreting the results in the context of the results from the edited GAL1 promoters supported the conclusion that the relative positioning of promoter elements is of great importance for determining in vivo promoter activity levels at endogenous chromosomal locations.

Despite the availability of whole-genome sequences for almost all model organisms, making faithful predictions on gene expression levels based solely on the corresponding promoter sequences is still a challenge. Previous studies aiming to decode genotype-phenotype relationships have often used either plasmid-based approaches or methods involving the integration of selection markers together with the promoter sequences to assess. The inevitable copy number fluctuations of plasmids and the disruptive nature of marker integrations make the results from these studies questionable. Elucidating the rules governing genotype-to-phenotype mapping requires a precise and marker-free genome editing method, such as the presently described methods. Through use of the methods of the invention, new insights were elucidated into the activity of canonical promoters in live yeast cells. Utilizing the CRISPR/Cas9 complex, the method involves the introduction of a novel cut site into a genomic location to edit, followed by the integration of an edited sequence into the same location in a scarless manner. Using this method to edit the GAL1 and GAL80 promoter sequences, it was discovered that the relative positioning of promoter elements was of great importance for setting promoter activity levels in single cells. In certain embodiments, the scarless application of the CRISPR technique presented herein can be extended to other organisms, such as for example other eukaryotic cells, such as for example mammalian cells, such as for example human cells, to decode genotype-phenotype relationships in a wide array of cellular systems.

Methods

In one aspect, the invention includes a method of performing scarless genome editing in a cell comprising a cell genome. The method comprises introducing into the cell Cas9 or a variant thereof, a first guide RNA (gRNA), a second gRNA, and a first polynucleotide. The first gRNA comprises a nucleotide sequence that is complementary to a cell genome sequence that is upstream of a first genomic region of interest. The second gRNA comprises a nucleotide sequence that is complementary to a cell genome sequence that is downstream of the first genomic region of interest. The first polynucleotide comprises a nucleotide sequence that is homologous to a cell genome sequence upstream and adjacent to the nucleotide sequence targeted by the first gRNA, a nucleotide sequence comprising a given CRISPR cut site, and a nucleotide sequence that is homologous to a cell genome sequence downstream and adjacent to the nucleotide sequence targeted by the second gRNA. The first genomic region of interest is excised from the cell genome and replaced in the cell genome with the first polynucleotide. At this time, the first and second gRNA as well as the first genomic region of interest are eliminated from the cell. Then, Cas9, a third gRNA, and a second polynucleotide are introduced to the cell. The third gRNA comprises a sequence that is complementary to the first polynucleotide. The second polynucleotide comprises a nucleotide sequence that is homologous to a cell genome sequence upstream and adjacent to the first polynucleotide, a nucleotide sequence that is a second genomic region of interest, and a nucleotide sequence that is homologous to a cell genome sequence downstream and adjacent to the first polynucleotide. The first polynucleotide is excised from the cell genome and replaced in the cell genome with the second polynucleotide.

It should be understood that the compositions and methods of the present invention apply to editing both DNA and RNA. The term "genome" as used herein is not limited to only chromosomal DNA and RNA, but rather could also include mobile DNA and RNA or synthetic DNA or RNA. The mobile DNA elements may be carried on plasmids, centromeric plasmids, or other mobile platforms. The methods of the invention can work both in live cells and in vitro.

In certain embodiments, the first genomic region of interest is a promoter sequence. In other embodiments, the first genomic region of interest is a non-coding sequence. In other embodiments, the first genomic region of interest is a coding sequence. In yet other embodiments, the second genomic region of interest is a modified version of the first genomic region of interest. For example, the second genomic region of interest can be a modified version of the first genomic region of interest, in that it comprises a nucleotide deletion, mutation, substitution, rearrangement, or addition with respect to the first genomic region of interest. The genomic region of interest can be a DNA or RNA sequence.

In certain embodiments, the first polynucleotide introduces a new/given CRISPR cut site and its associated protospacer adjacent motif (PAM) sequence into the cell genome. In one non-limiting example, the PAM sequence is 5'-NGG-3', however any PAM can be introduced by the methods of the present invention. In one embodiment, the PAM is considered a "landing pad".

The compositions and methods of the present invention can be multiplexed, allowing multiple genomic loci to be edited. Such multiplexed method can encompass editing of two or more genomic regions, as illustrated herein. In one embodiment, the method can further comprise editing a third genomic region of interest by introducing into the cell Cas9 or a variant thereof, a fourth guide RNA (gRNA), a fifth gRNA, and a third polynucleotide. The fourth gRNA comprises a nucleotide sequence that is complementary to a cell genome sequence that is upstream of the third genomic region of interest. The fifth gRNA comprises a nucleotide sequence that is complementary to a cell genome sequence that is downstream of the third genomic region of interest. The third polynucleotide comprises a nucleotide sequence that is homologous to a cell genome sequence upstream and adjacent to the nucleotide sequence targeted by the fourth gRNA, a nucleotide sequence comprising a given CRISPR cut site, and a nucleotide sequence that is homologous to a cell genome sequence downstream and adjacent to the nucleotide sequence targeted by the fifth gRNA. The third genomic region of interest is excised from the cell genome and replaced in the cell genome with the third polynucleotide. Then, Cas9 or a variant thereof, a sixth gRNA, and a fourth polynucleotide are introduced into the cell. The sixth gRNA comprises a nucleotide sequence that is complementary to the third polynucleotide. The fourth polynucleotide comprises a nucleotide sequence that is homologous to a cell genome sequence upstream and adjacent to the third polynucleotide, a nucleotide sequence that is a fourth genomic region of interest, and a nucleotide sequence that is homologous to a cell genome sequence downstream and adjacent to the third polynucleotide. The third polynucleotide is excised from the cell genome and replaced in the cell genome with the fourth polynucleotide. In certain embodiments, the editing of the third genomic region is performed approximately simultaneously with the editing of the first genomic region. In certain embodiments, the editing of the third genomic region is performed before the editing of the first genomic region. In certain embodiments, the editing of the third genomic region is performed after the editing of the first genomic region. The method can further comprise editing additional genomic regions of interest. For example, additional gRNAs and polynucleotides corresponding to additional genomic regions of interest can be designed and used according to the methods of the present invention.

In certain embodiments, the cell is a eukaryotic cell. The eukaryotic cell can be selected from the group consisting of a mammalian cell, a human cell, or a yeast cell. In certain embodiments, the cell is a prokaryotic cell, or a plant cell, or a fungal cell, or a metazoan cell. It should be understood by one skilled in the art that the invention is not limited to only these cells but rather any cell type or cell line can be used.

Certain non-limiting applications of the method include somatic gene, DNA, or RNA therapy in host cells, including but not limited to mammalian cells. Other non-limiting applications include somatic gene, DNA, or RNA enhancement in host cells, including but not limited to mammalian cells. Using the methods described herein, partial or whole replacement of a gene, DNA, or RNA with an altered gene, DNA, or RNA replacement(s) performed at specific or pre-defined genome location(s) or RNA territories can be achieved for the goals of disease treatment, or phenotypic or functional enhancement (for example, in a non-limiting embodiment, reversal of age-related phenotypes or rejuvenation-oriented genetic therapies). The methods of the invention can be applied to any diseases that occur due to known or to-be-identified genetic or epigenetic mechanisms, including but not limited to, cancer, diabetes, neurodegenerative diseases, Alzheimer's disease and Alzheimer's disease-related dementia, heart diseases, and lung diseases. In certain embodiments, the methods of the invention can be used to treat diseases and/or modify characteristics in any organisms such as crop plants (e.g. modifying plants for adaptability, crop resistance, and/or insect resistance; allowing for production of chemical or biological materials in plants). In other embodiments, the methods can be used to conduct genome engineering in organisms such as bacteria, yeasts, and plants for non-disease related purposes (e.g. producing commercially relevant chemical or biological products, modifying biochemical pathways, performing synthetic biology modification, using organisms as biofactories).

In certain embodiments, the efficiency of the first step or the second step of the method can be improved by any means known to one of ordinary skill in the art. For example, efficiency improvements can be achieved by introducing a fluorescent or non-fluorescent selection marker as the product of the first step (marker being the nucleotide sequence to introduce). Then, selection of the cells carrying the marker can enhance the efficiency of the first step. At the end of the second step, on the other hand, selection of the cells not carrying the marker can improve the efficiency of the second step.

Compositions, Systems and Kits

In one aspect, the invention includes a scarless genome editing system. The system comprises Cas9 or a variant thereof, a first guide RNA (gRNA), a second gRNA, a third gRNA, a first polynucleotide, and a second polynucleotide. The system performs scarless genome editing in a cell comprising a cell genome and a first genomic region of interest is replaced in the cell genome with a second genomic region of interest. The first gRNA comprises a nucleotide sequence that is complementary to a cell genome sequence that is upstream of the first genomic region of interest, and the second gRNA comprises a nucleotide sequence that is complementary to a cell genome sequence that is downstream of the first genomic region of interest. The first polynucleotide comprises a nucleotide sequence that is homologous to a cell genome sequence upstream and adjacent to the nucleotide sequence targeted by the first gRNA, a nucleotide sequence comprising a given CRISPR cut site, and a nucleotide sequence that is homologous to a cell genome sequence that is downstream and adjacent to the nucleotide sequence targeted by the second gRNA. The third gRNA comprises a nucleotide sequence that is complementary to the first polynucleotide. The second polynucleotide comprises a nucleotide sequence that is homologous to a cell genome sequence upstream and adjacent to the first polynucleotide, a nucleotide sequence that is a second genomic region of interest, and a nucleotide sequence that is homologous to a cell genome sequence downstream and adjacent to the first polynucleotide.

Another aspect of the invention includes a kit comprising Cas9, a first gRNA, a second gRNA, a third gRNA, a first polynucleotide, a second polynucleotide, and instructional material for use thereof. The first gRNA comprises a nucleotide sequence that is complementary to a cell genome sequence that is upstream of the first genomic region of interest, and the second gRNA comprises a nucleotide sequence that is complementary to a cell genome sequence that is downstream of the first genomic region of interest. The first polynucleotide comprises a nucleotide sequence that is homologous to a cell genome sequence upstream and adjacent to the nucleotide sequence targeted by the first gRNA, a nucleotide sequence comprising a given CRISPR cut site, and a nucleotide sequence that is homologous to a cell genome sequence that is downstream and adjacent to the nucleotide sequence targeted by the second gRNA.

The genomic region of interest can be a DNA or RNA sequence.

In certain embodiments, the first polynucleotide introduces a new/given CRISPR cut site and its associated protospacer adjacent motif (PAM) sequence into the cell genome. In one non-limiting example, the PAM sequence is 5'-NGG-3', however any PAM can be introduced by the methods of the present invention. In one embodiment, the PAM is considered a "landing pad".

In certain embodiments, the cell is a eukaryotic cell. The eukaryotic cell can be selected from the group consisting of a mammalian cell, a human cell, or a yeast cell. In certain embodiments, the cell is a prokaryotic cell, or a plant cell, or a fungal cell, or a metazoan cell. It should be understood by one skilled in the art that the invention is not limited to only these cells but rather any cell type or cell line can be used.

In certain embodiments, the genome editing system or kit is multiplexed, allowing multiple genes to be edited simultaneously. In one embodiment, two genomic regions are edited simultaneously. In another embodiment, more than two genomic regions are edited simultaneously.

CRISPR/Cas9

The CRISPR/Cas9 system is a facile and efficient system for inducing targeted genetic alterations. Target recognition by the Cas9 protein requires a 'seed' sequence within the guide RNA (gRNA) and a conserved di-nucleotide containing protospacer adjacent motif (PAM) sequence upstream of the gRNA-binding region. The CRISPR/Cas9 system can thereby be engineered to cleave virtually any DNA sequence by redesigning the gRNA in cell lines (such as 293T cells), primary cells, and CAR T cells. The CRISPR/Cas9 system can simultaneously target multiple genomic loci by co-expressing a single Cas9 protein with two or more gRNAs, making this system uniquely suited for multiple gene editing or synergistic activation of target genes.

The Cas9 protein and guide RNA form a complex that identifies and cleaves target sequences. Cas9 is comprised of six domains: REC I, REC II, Bridge Helix, PAM interacting, HNH, and RuvC. The Red domain binds the guide RNA, while the Bridge helix binds to target DNA. The HNH and RuvC domains are nuclease domains. Guide RNA is engineered to have a 5' end that is complementary to the target DNA sequence. Upon binding of the guide RNA to the Cas9 protein, a conformational change occurs activating the protein. Once activated, Cas9 searches for target DNA by binding to sequences that match its protospacer adjacent motif (PAM) sequence. A PAM is a two to six nucleotide base sequence within one nucleotide downstream of the region complementary to the guide RNA. In one non-limiting example, the PAM sequence is 5'-NGG-3'. When the Cas9 protein finds its target sequence with the appropriate PAM, it melts the bases upstream of the PAM and pairs them with the complementary region on the guide RNA. Then the RuvC and HNH nuclease domains cut the target DNA after the third nucleotide base upstream of the PAM.

One non-limiting example of a CRISPR/Cas system used to inhibit gene expression, CRISPRi, is described in U.S. Publication No. US20140068797. CRISPRi induces permanent gene disruption that utilizes the RNA-guided Cas9 endonuclease to introduce DNA double stranded breaks which trigger error-prone repair pathways to result in frame shift mutations. A catalytically dead Cas9 lacks endonuclease activity. When coexpressed with a guide RNA, a DNA recognition complex is generated that specifically interferes with transcriptional elongation, RNA polymerase binding, or transcription factor binding. This CRISPRi system efficiently represses expression of targeted genes.

CRISPR/Cas gene disruption occurs when a guide nucleic acid sequence specific for a target gene and a Cas endonuclease are introduced into a cell and form a complex that enables the Cas endonuclease to introduce a double strand break at the target gene. In certain embodiments, the CRISPR/Cas system comprises an expression vector, such as, but not limited to, an pAd5F35-CRISPR vector. In other embodiments, the Cas expression vector induces expression of Cas9 endonuclease. Other endonucleases may also be used, including but not limited to, T7, Cas3, Cas8a, Cas8b, Cas10d, Cse1, Csy1, Csn2, Cas4, Cas10, Csm2, Cmr5, Fok1, other nucleases known in the art, and any combination thereof.

In certain embodiments, inducing the Cas expression vector comprises exposing the cell to an agent that activates an inducible promoter in the Cas expression vector. In such embodiments, the Cas expression vector includes an inducible promoter, such as one that is inducible by exposure to an antibiotic (e.g., by tetracycline or a derivative of tetracycline, for example doxycycline). However, it should be appreciated that other inducible promoters can be used. The inducing agent can be a selective condition (e.g., exposure to an agent, for example an antibiotic) that results in induction of the inducible promoter. This results in expression of the Cas expression vector.

In certain embodiments, guide RNA(s) and Cas9 can be delivered to a cell as a ribonucleoprotein (RNP) complex. RNPs are comprised of purified Cas9 protein complexed with gRNA and are well known in the art to be efficiently delivered to multiple types of cells, including but not limited to stem cells and immune cells (Addgene, Cambridge, MA, Minis Bio LLC, Madison, WI).

The guide RNA is specific for a genomic region of interest and targets that region for Cas endonuclease-induced double strand breaks. The target sequence of the guide RNA sequence may be within a loci of a gene or within a non-coding region of the genome. In certain embodiments, the guide nucleic acid sequence is at least 10, 11, 12, 13, 14, 15, 16, 17, 18, 19, 20, 21, 22, 23, 24, 25, 26, 27, 30, 31, 32, 33, 34, 35, 36, 37, 38, 39, 40 or more nucleotides in length.

Guide RNA (gRNA), also referred to as "short guide RNA" or "sgRNA", provides both targeting specificity and scaffolding/binding ability for the Cas9 nuclease. The gRNA can be a synthetic RNA composed of a targeting sequence and scaffold sequence derived from endogenous bacterial crRNA and tracrRNA. gRNA is used to target Cas9 to a specific genomic locus in genome engineering experiments. Guide RNAs can be designed using standard tools well known in the art.

In the context of formation of a CRISPR complex, "target sequence" refers to a sequence to which a guide sequence is designed to have some complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides. In certain embodiments, a target sequence is located in the nucleus or cytoplasm of a cell. In other embodiments, the target sequence may be within an organelle of a eukaryotic cell, for example, mitochondrion or nucleus. Typically, in the context of an endogenous CRISPR system, formation of a CRISPR complex (comprising a guide sequence hybridized to a target sequence and complexed with one or more Cas proteins) results in cleavage of one or both strands in or near (e.g., within about 1, 2, 3, 4, 5, 6, 7, 8, 9, 10, 20, 50 or more base pairs) the target sequence. As with the target sequence, it is believed that complete complementarity is not needed, provided this is sufficient to be functional.

In certain embodiments, one or more vectors driving expression of one or more elements of a CRISPR system are introduced into a host cell, such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In certain embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g., each in a different intron, two or more in at least one intron, or all in a single intron).

In certain embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Additional domains that may form part of a fusion protein comprising a CRISPR enzyme are described in US20110059502, incorporated herein by reference. In certain embodiments, a tagged CRISPR enzyme is used to identify the location of a target sequence.

Conventional viral and non-viral based gene transfer methods can be used to introduce nucleic acids in mammalian and non-mammalian cells or target tissues. Such methods can be used to administer nucleic acids encoding components of a CRISPR system to cells in culture, or in a host organism. Non-viral vector delivery systems include DNA plasmids, RNA (e.g., a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell (Anderson, 1992, Science 256:808-813; and Yu, et al., 1994, Gene Therapy 1:13-26).

In certain embodiments, the CRISPR/Cas is derived from a type II CRISPR/Cas system. In other embodiments, the CRISPR/Cas system is derived from a Cas9 protein. The Cas9 protein can be from *Streptococcus pyogenes, Streptococcus thermophilus*, or other species. The term "Cas9" should be interpreted to include any and all types and/or variants of Cas9. Examples of Cas9 variants include but are not limited to Cas9-nickase (Cas9n), nuclease dead Cas9 (dCas9) fused to the non-specific endonuclease FokI (dCas9-FokI), "enhanced Cas9", "high-fidelity Cas9", eSpCas9, spCas9-HF1, HypaCas9, *S. pyogenes* VQR, EQR and VRER mutants, "non-Sp" Cas9s, and full nuclease variants.

In general, Cas proteins comprise at least one RNA recognition and/or RNA binding domain. RNA recognition and/or RNA binding domains interact with the guiding RNA. Cas proteins can also comprise nuclease domains (i.e., DNase or RNase domains), DNA binding domains, helicase domains, RNAse domains, protein-protein interaction domains, dimerization domains, as well as other domains. The Cas proteins can be modified to increase nucleic acid binding affinity and/or specificity, alter an enzymatic activity, and/or change another property of the protein. In certain embodiments, the Cas-like protein of the fusion protein can be derived from a wild type Cas9 protein or fragment thereof. In other embodiments, the Cas can be derived from modified Cas9 protein. For example, the amino acid sequence of the Cas9 protein can be modified to alter one or more properties (e.g., nuclease activity, affinity, stability, and so forth) of the protein. Alternatively, domains of the Cas9 protein not involved in RNA-guided cleavage can be eliminated from the protein such that the modified Cas9 protein is smaller than the wild type Cas9 protein. In general, a Cas9 protein comprises at least two nuclease (i.e., DNase) domains. For example, a Cas9 protein can comprise a RuvC-like nuclease domain and a HNH-like nuclease domain. The RuvC and HNH domains work together to cut single strands to make a double-stranded break in DNA. (Jinek, et al., 2012, Science, 337:816-821). In certain embodiments, the Cas9-derived protein can be modified to contain only one functional nuclease domain (either a RuvC-like or a HNH-like nuclease domain). For example, the Cas9-derived protein can be modified such that one of the nuclease domains is deleted or mutated such that it is no longer functional (i.e., the nuclease activity is absent). In some embodiments in which one of the nuclease domains is inactive, the Cas9-derived protein is able to introduce a nick into a double-stranded nucleic acid (such protein is termed a "nickase"), but not cleave the double-stranded DNA. In any of the above-described embodiments, any or all of the nuclease domains can be inactivated by one or more deletion mutations, insertion mutations, and/or substitution mutations using well-known methods, such as site-directed mutagenesis, PCR-mediated mutagenesis, and total gene synthesis, as well as other methods known in the art.

In one non-limiting embodiment, a vector drives the expression of the CRISPR system. The art is replete with suitable vectors that are useful in the present invention. The vectors to be used are suitable for replication and, optionally, integration in eukaryotic cells. Typical vectors contain transcription and translation terminators, initiation sequences, and promoters useful for regulation of the expression of the desired nucleic acid sequence. The vectors of the present invention may also be used for nucleic acid standard gene delivery protocols. Methods for gene delivery are known in the art (U.S. Pat. Nos. 5,399,346, 5,580,859 & 5,589,466, incorporated by reference herein in their entireties).

Further, the vector may be provided to a cell in the form of a viral vector. Viral vector technology is well known in the art and is described, for example, in Sambrook et al. (4th Edition, Molecular Cloning: A Laboratory Manual, Cold Spring Harbor Laboratory, New York, 2012), and in other virology and molecular biology manuals. Viruses, which are useful as vectors include, but are not limited to, retroviruses, adenoviruses, adeno-associated viruses, herpes viruses, Sindbis virus, gammaretrovirus and lentiviruses. In general, a suitable vector contains an origin of replication functional in at least one organism, a promoter sequence, convenient restriction endonuclease sites, and one or more selectable markers (e.g., WO 01/96584; WO 01/29058; and U.S. Pat. No. 6,326,193).

Introduction of Nucleic Acids

Methods of introducing nucleic acids into a cell include physical, biological and chemical methods. Physical methods for introducing a polynucleotide, such as DNA or RNA, into a cell include transfection, transformation, transduction, calcium phosphate precipitation, lipofection, particle bombardment, microinjection, electroporation, and the like. RNA and DNA can be introduced into cells using commercially available methods which include electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany). RNA and DNA can also be introduced into cells using cationic liposome mediated transfection using lipofection, using polymer encapsulation, using peptide mediated transfection, or using biolistic particle delivery systems such as "gene guns" (see, for example, Nishikawa, et al. Hum Gene Ther., 12(8):861-70 (2001).

Biological methods for introducing a polynucleotide of interest into a cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362. Non-viral vector such as plasmids can also be used to introduce nucleic acids or polynucleotides into a cell. In certain embodiments plasmids containing guide RNAs are transfected into a cell.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Regardless of the method used to introduce exogenous nucleic acids into a host cell, in order to confirm the presence of the nucleic acids in the host cell, a variety of assays may be performed. Such assays include, for example, "molecular biological" assays well known to those of skill in the art, such as gel electrophoresis, Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, Molecular Cloning: A Laboratory Manual", fourth edition (Sambrook et al., (2012) *Molecular Cloning*, Cold Spring Harbor Laboratory); "Oligonucleotide Synthesis" (Gait, M. J. (1984). Oligonucleotide synthesis. IRL press); "Culture of Animal Cells" (Freshney, R. (2010). Culture of animal cells. Cell Proliferation, 15(2.3), 1); "Methods in Enzymology" "Weir's Handbook of Experimental Immunology" (Wiley-Blackwell; 5 edition (Jan. 15, 1996); "Gene Transfer Vectors for Mammalian Cells" (Miller and Carlos, (1987) Cold Spring Harbor Laboratory, New York); "Short Protocols in Molecular Biology" (Ausubel et al., Current Protocols; 5 edition (Nov. 5, 2002)); "Polymerase Chain Reaction: Principles, Applications and Troubleshooting", (Babar, M., VDM Verlag Dr. Müller (Aug. 17, 2011)); "Current Protocols in Immunology" (Coligan, John Wiley & Sons, Inc. Nov. 1, 2002).

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

The materials and methods employed in these experiments are now described.

Construction of Plasmids.

The base plasmid used for all plasmid construction was pRS315, a yeast centromeric plasmid containing a LEU2 marker. In order to create plasmids containing a single gRNA cassette, a 388 bp gRNA cassette sequence modified from the template created by (DiCarlo et al., 2013. *Nucl. Acid Res.* 41, 4336-4343) was ordered (Integrated DNA Technologies). The cassette contains a promoter and terminator as well as the 20 bp targeting sequence in between them to determine cutting specificity. These sequences were constructed with a BamHI cut site on the 3' end and a HindIII cut site on the 5' end of the cassette. Upon receipt, these sequences and pRS315 were digested with the appropriate enzymes and ligated to form plasmids containing a gRNA cassette. In order to create plasmids containing two gRNA cassettes, the two cassettes were individually ordered with the first containing a NotI site and a BamHI site and the second containing an XmaI site and a HindIII site. The two were then ligated into pRS315 in two separate transformations to create a plasmid containing two gRNAs separated by 12 base pairs.

Introducing the CAS9 Gene into Yeast.

All strains were created from WP35, a W303 strain with one copy of the $P_{GAL1}$-YFP construct inserted into the ho locus. The rest of the yeast genome was unaltered. To insert CAS9 into this strain, plasmid #43802 was obtained from Addgene. This plasmid (DiCarlo et al., 2013. *Nucl. Acid Res.* 41, 4336-4343), contains the CAS9 gene under a constitutive TEF1 promoter along with a TRP1 marker. To insert it into WP35, the centromeric region was removed from the plasmid, and then the plasmid was linearized in the TRP1 gene using the MfeI enzyme. The linear product was transformed into WP35 using the standard lithium acetate (LiOAc) transformation technique. This resulted in the strain GE1.

Introducing Rational Edits on the GAL1 and GAL80 Promoters.

The first step of editing at the GAL1 promoter ($P_{GAL1}$) consisted of transforming GE1 with a plasmid containing gRNAs targeting two sites flanking $P_{GAL1}$, with the goal of cutting out the entirety of $P_{GAL}$. A donor oligonucleotide carrying a novel 30 bp CRISPR cut and PAM site in between 50 bp regions homologous to each genomic region flanking the GAL1 promoter was co-transformed (LiOAc technique) with the plasmid containing two gRNAs so that cells could use the donor as a repair template. The transformed cells were then grown on –LEU plates for two days after which colonies were PCR tested and sequenced to verify that editing had taken place. After this, replica plating between rich media (YPD) and –LEU media was used to locate colonies which had lost the centromeric plasmid used in the first step.

The second step of the editing process consisted of transforming (using the LiOAc technique) the intermediate strain carrying the 30 bp novel PAM site with a plasmid containing a gRNA cassette targeting the new CRISPR cut site in the presence of a new donor oligonucleotide. The donor consisted of an edited version of the $P_{GAL1}$ in between 50 bp sequences homologous to the genomic regions flanking the cut site. The transformed cells were then grown on –LEU plates for two days after which colonies were PCR tested and sequenced to verify that editing had taken place.

Editing $P_{GAL80}$ involved the same two-step process, but used gRNAs and donors that were relevant to $P_{GAL80}$. Finally, to construct the multiplexed strains, the transformations for the first step of the editing process were performed successively in order to create an intermediate yeast strain with both $P_{GAL1}$ and $P_{GAL80}$ replaced by two novel PAM sites. The second step of the editing process was completed simultaneously for the $P_{GAL1}$ and $P_{GAL80}$ loci by using a single plasmid containing two gRNAs (each targeting one locus) and two separate donor oligonucleotides carrying the edited $P_{GAL1}$ and $P_{GAL80}$ sequences.

Quantifying the Efficiency of the CRISPR Editing.

The editing efficiency was calculated by dividing the number of correctly edited colonies (as identified by PCR confirmation and sequencing) by the total number of colonies examined. The use of a selectable marker on the gRNA-containing plasmid ensured that only colonies which received a plasmid could grow and be used for analysis. To quantify the efficiency of the first step of the editing process, results obtained from targeting the GAL80 promoter site were used. Two independent transformations were conducted, 8 and 24 colonies were collected from the two transformations, and the editing efficiency values were calculated separately. As a result, 6 out of 8 colonies and 14 out of 24 colonies were counted as correct. The results were combined to provide the overall efficiency in terms of mean and standard error of the mean (S.E.M., N=2) as presented herein. In quantifying the efficiency of the second step of the editing process, three independent transformations were conducted by simultaneously editing the GAL80 and GAL1 promoters, 24 colonies were collected from each transformation, and the editing efficiency values were calculated separately. The results were combined to provide the overall efficiency in terms of mean and standard error of the mean (S.E.M., N=3).

Growth Conditions, Media, and Flow Cytometry Data Analysis.

Cells were grown in the appropriate synthetic amino acid dropout media. All growths were conducted in duplicate at 30° C. in a shaking incubator in 5 mL of media. Cells were first grown overnight for 22 hours in minimal media containing 0.1% mannose as the carbon source, reaching to an optical density ($OD_{600}$) between 0.075 and 0.15. They were subsequently diluted into the induction media containing 0.1% mannose and the appropriate concentration of galactose, and grown for another 22 hours, reaching to a cell density between 0.075 and 0.15. After the induction period, single cell fluorescence values were analyzed using flow cytometry (Stratedigm-8 with HTAS). Each FACS sample had on average 3,000 cells after gating. Log-amplified fluorescence measurements for the gated cells were converted to linear scale for analysis. A threshold for ON state (75.7 a.u.) was selected based on fluorescence measurements from uninduced, unedited cells and uniformly applied to all samples. The fraction of ON cells was then quantified for each sample. For each galactose concentration that resulted in at least 5% ON cell, the mean expression level of the such cells in the ON state was also quantified.

The results of the experiments are now described.

Example 1: Scarless Genome Editing in Live Cells

To demonstrate the viability of this new technique, a strain of S. cerevisiae was chosen in which one copy of the canonical GAL1 promoter driving the yellow fluorescent protein (YFP) has been integrated into the ho locus (Acar et al., 2005. Nature 435, 228-232 and Acar et al. 2010. Science 329, 1656-1660) (FIG. 1A). By targeting this promoter, the influence of any edits on the output of YFP fluorescence in environments containing various concentrations of galactose could be seen.

The first step of the genome editing process was to replace the existing $P_{GAL1}$ with a short (30 bp) region containing a novel CRISPR cut site (FIG. 1A). To do this, gRNAs targeting the nearest available cut sites immediately before and after the GAL1 promoter were added to a pRS315 plasmid containing a yeast centromeric element and a LEU2 marker. In addition, a donor oligonucleotide was created containing the novel cut site flanked by 50 bp of homology to each of the regions immediately adjacent to the cut sites. The plasmid and donor oligonucleotide were co-transformed into a yeast strain containing CAS9 driven by a constitutive promoter as well as the $P_{GAL1}$-YFP construct described elsewhere herein. Because of the relative proximity of the cut sites, the cellular repair machinery treats the two as a single break, which is repaired through the use of the added donor oligonucleotide while the intervening region is lost. The end result of this step is the replacement of the original $P_{GAL1}$ and small adjacent regions including the original PAM sites with a 30 bp novel DNA sequence containing a new CRISPR cut site.

Figure 1B:
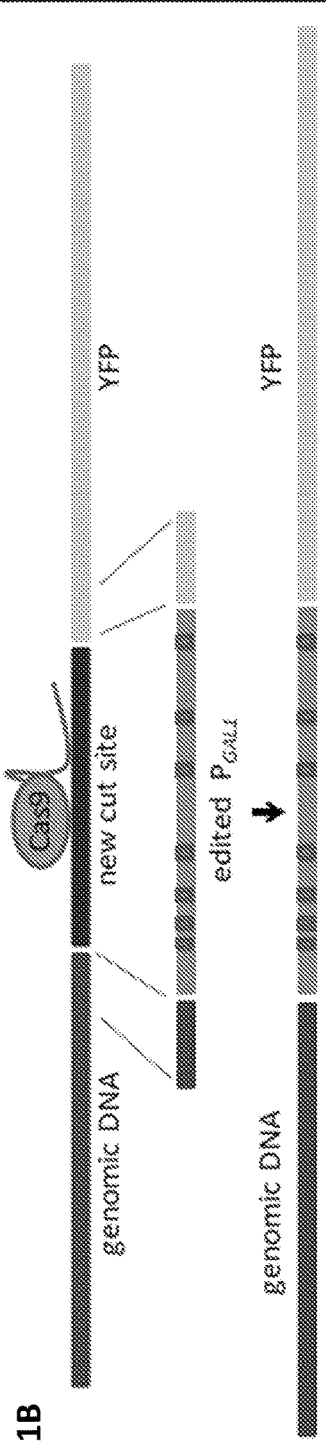

The second step of the editing process begins upon creation of the new strain described elsewhere herein. This involves inserting a gRNA targeting the introduced PAM site into a pRS315 plasmid and co-transforming it into the new yeast strain along with a new piece of donor DNA, which consists of the original promoter containing any desired edits and 50 bp of homology to each end of the new break (FIG. 1B). The repair replaces the adjacent regions lost in the previous step and adds the newly edited $P_{GAL1}$ region. Ultimately, the only changes to the original strain are those desired. The targeting and PAM sites targeted in the first step were reintroduced such that no trace of the editing process remains in the final genome (FIG. 1B).

Example 2: Characterization of Editing Efficiency

Figure 1C:
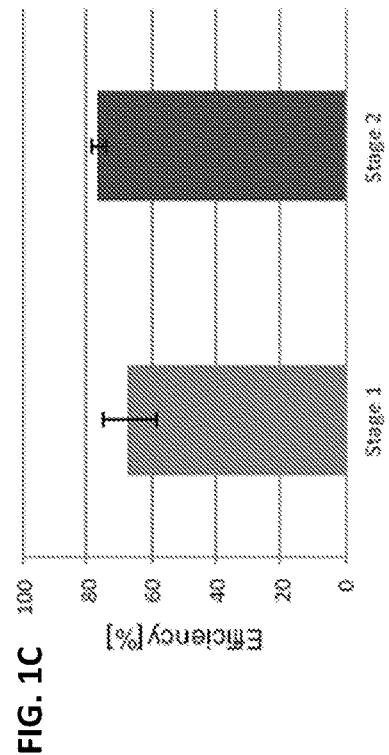

The editing efficiency for both steps of the technique was measured (FIG. 1C), as efficiency is a key factor for any genome editing technique. The initial step had an efficiency of 63%. The first step must only be completed once for any editing to be conducted at the relevant locus. The efficiency of the second editing step is much more important and this step was found to have an efficiency of 77% (FIG. 1C).

Figure 2A:
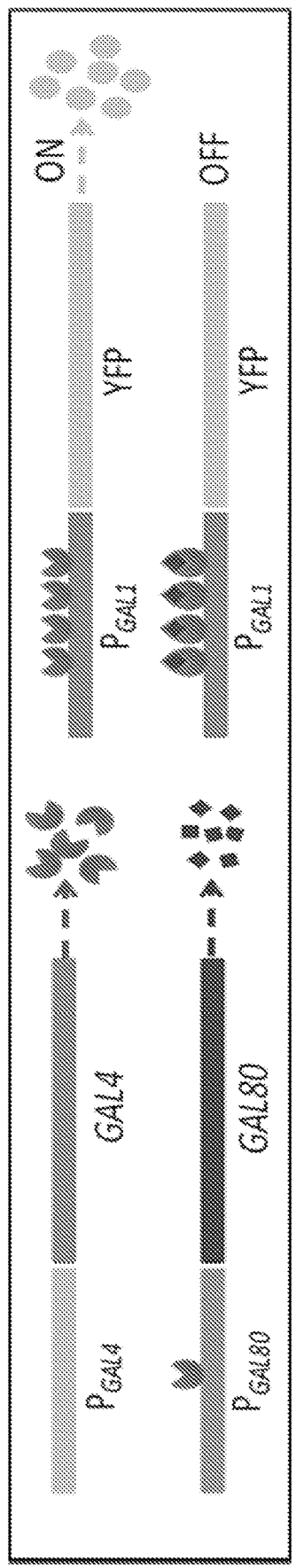
FIGS. 2A-2D are a series of images and graphs illustrating components of the GAL network and characterization of GAL1 promoter activity.

Example 3: Editing GAL1 Promoter Architecture and Measuring Promoter Activity in Single Cells To functionally validate the technique of the present invention, the phenotypic consequences of introducing rational edits to a promoter were evaluated. The effects of removing Gal4 binding sites from the canonical GAL1 promoter, which is a faithful reporter of the yeast galactose (GAL) network activity, were investigated. The constitutively expressed Gal4 protein serves as the main transcriptional activator of the GAL network. It activates transcription from all network promoters, including that of the GAL1 promoter, by binding to a 17 bp site (CGG-N(11)-CCG) on the promoters. On the other hand, Gal80 repressor proteins negatively regulate the network activity by binding to Gal4 on promoter sites (FIG. 2A). Galactose relieves Gal80 repression via Gal3 proteins. Activated Gal3 binds to Gal80, leading to the dissociation of Gal80 from Gal4 proteins. There is no known crosstalk between the GAL network and any other gene except for an inhibitor is dependent on the presence of glucose, making it ideal for study in conditions without the presence of glucose.

Figure 2B:
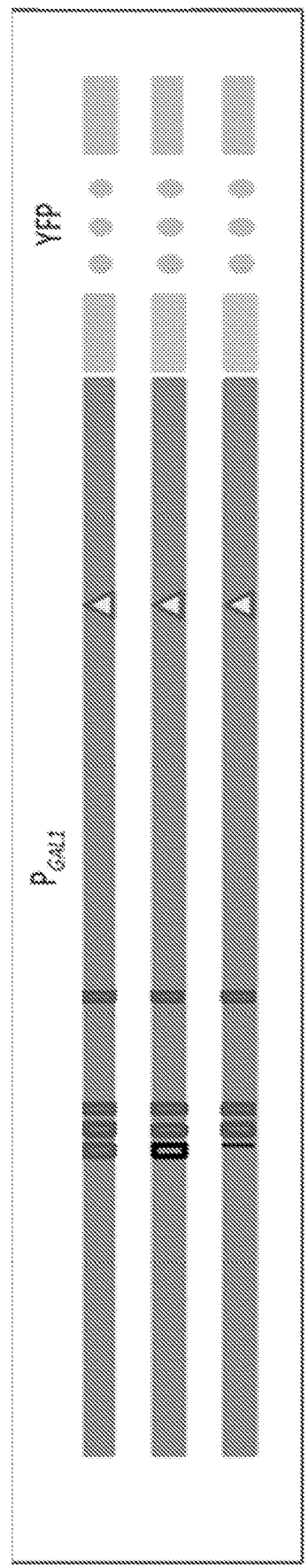

The GAL network is induced by galactose in a bimodal fashion. The activity of the unedited wild type GAL1 promoter driving YFP was used as a reference. Yeast cells were grown for 22 hours in the presence of various galactose concentrations (0%, 0.025%, 0.05%, 0.1%, 0.2%, 0.4%, 0.5%) in addition to 0.1% mannose Mannose was used as a non-inducing sugar that is metabolized by both OFF and ON cells of the bimodal distribution. At the end of the 22-hour period, single cell YFP expression levels of ~3,000 cells were measured using a flow cytometer (FACS), and two important phenotypes associated with a bimodal distribution were quantified for each condition: fraction of ON cells and mean expression level of the ON cells (FIG. 2B).

Altering the architecture of the GAL1 promoter can potentially change the fraction of ON cells, the mean expression level of the ON state, or both. The native GAL1 promoter contains three Gal4 binding sites immediately adjacent to each other followed by a fourth binding site with a different sequence 45 base pairs downstream of the previous three (FIG. 2B). The 185-190 base pairs downstream of the fourth site form a TATA box and the 5'-ATG-3' start codon is 145 base pairs downstream of the TATA box (FIG. 2B). The four Gal4 binding sites were altered in two ways: by simply removing the 17 bp binding site from the promoter outright and by recoding the conserved 5'-CGG-3' and 5'-CCG-3' sequences of the site into randomized A/T sequences of the same length, abolishing the binding of Gal4 on that position while keeping the number of base pairs intact.

Figure 2C:
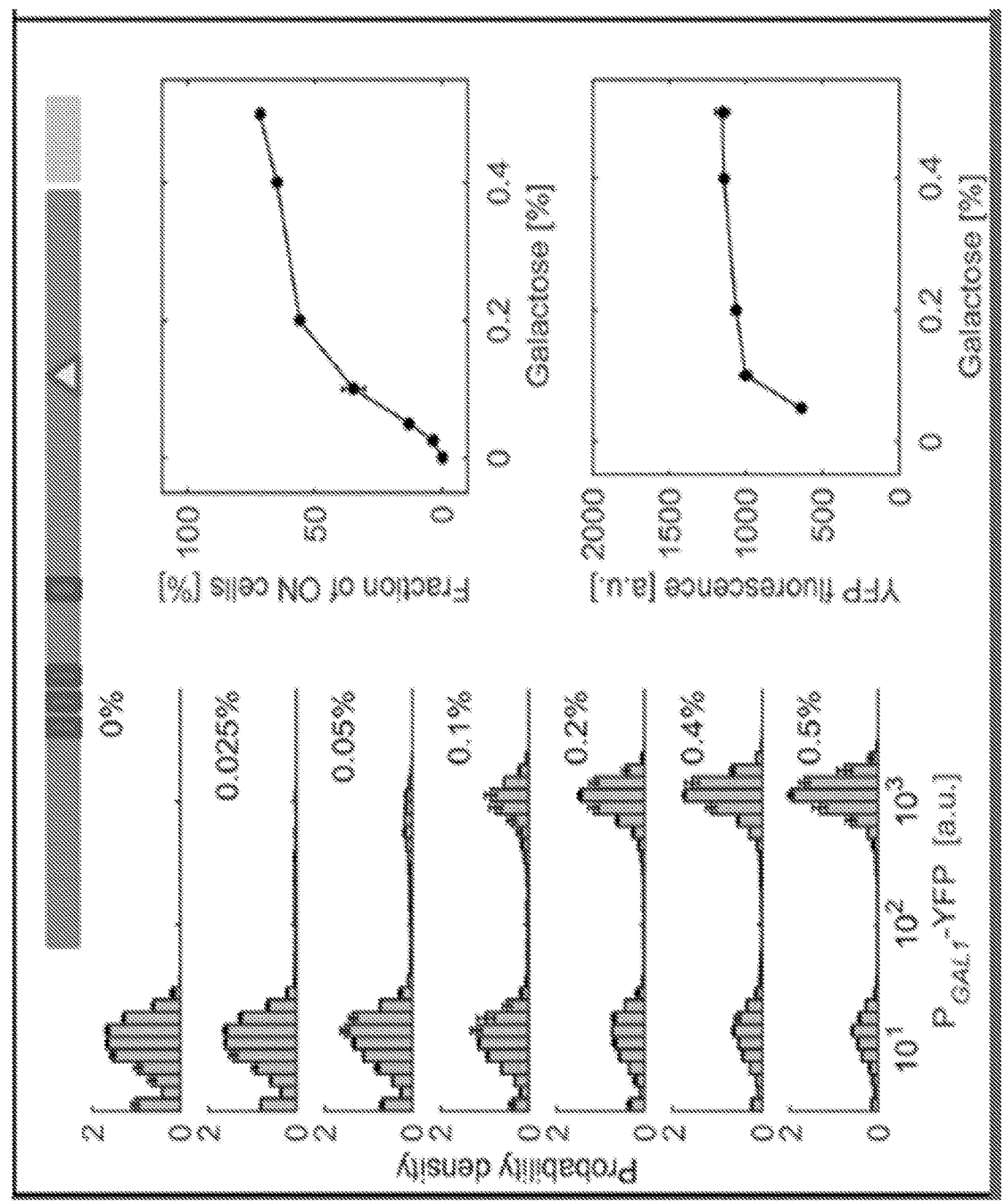
Figure 2D:
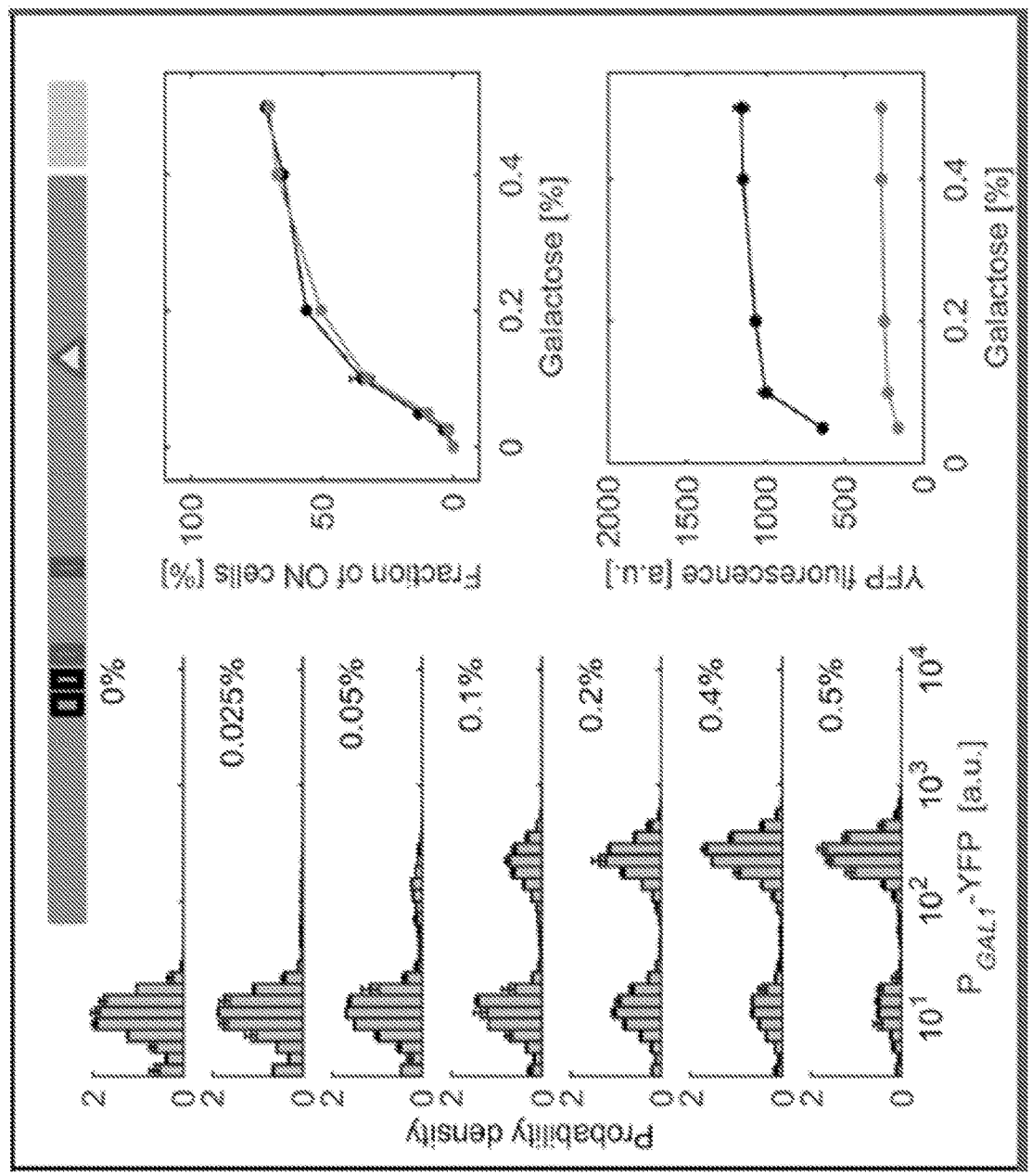

To investigate the phenotypic consequences of these binding site alterations on the activity of the GAL1 promoter, galactose induction experiments were performed and measured the resulting promoter activity profiles in single cells. FIG. 2C shows results from the wild type strain, while FIG. 2D shows, as an example, results from one of the promoter-edited strains. In the edited strain, the first and second Gal4 binding sites were recoded to neutral sites on the GAL1 promoter. Compared to the wild type promoter activity, the recoding of these two binding sites resulted in a reduction of the ON-state mean expression level, but a nearly identical fraction of ON cells. These results verify that edits made using this method can produce phenotypic changes in vivo.

Figure 3A:
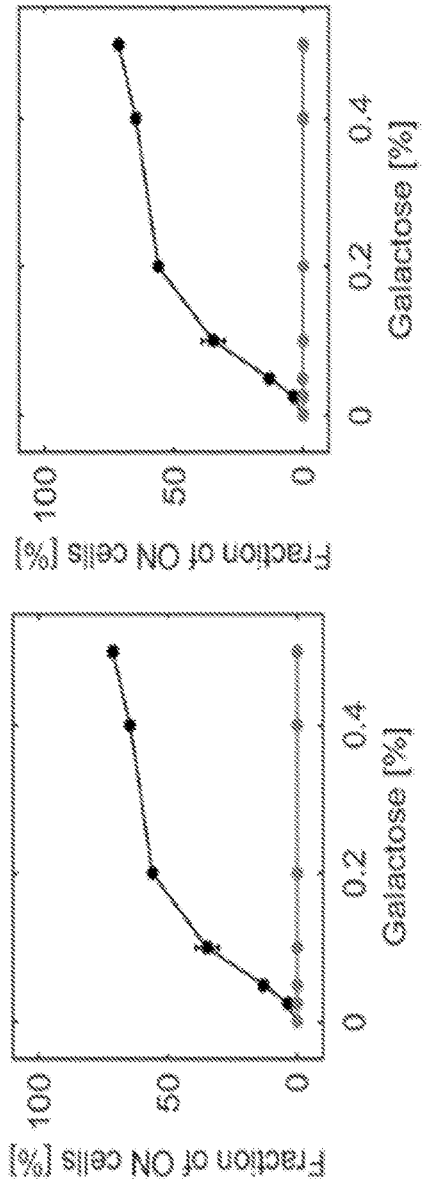
FIGS. 3A-3D are a series of graphs and images illustrating systematic editing of the canonical Gal4 binding sites on the GAL1 promoter. Each horizontal bar indicates one strain and illustrates the specific edits introduced in the GAL1 promoter. The filled boxes are Gal4 binding sites while removing a Gal4 binding site by recoding is depicted by an empty box. A triangle indicates the TATA box and the black line indicates the removal of a Gal4 binding site.
Figure 13A:
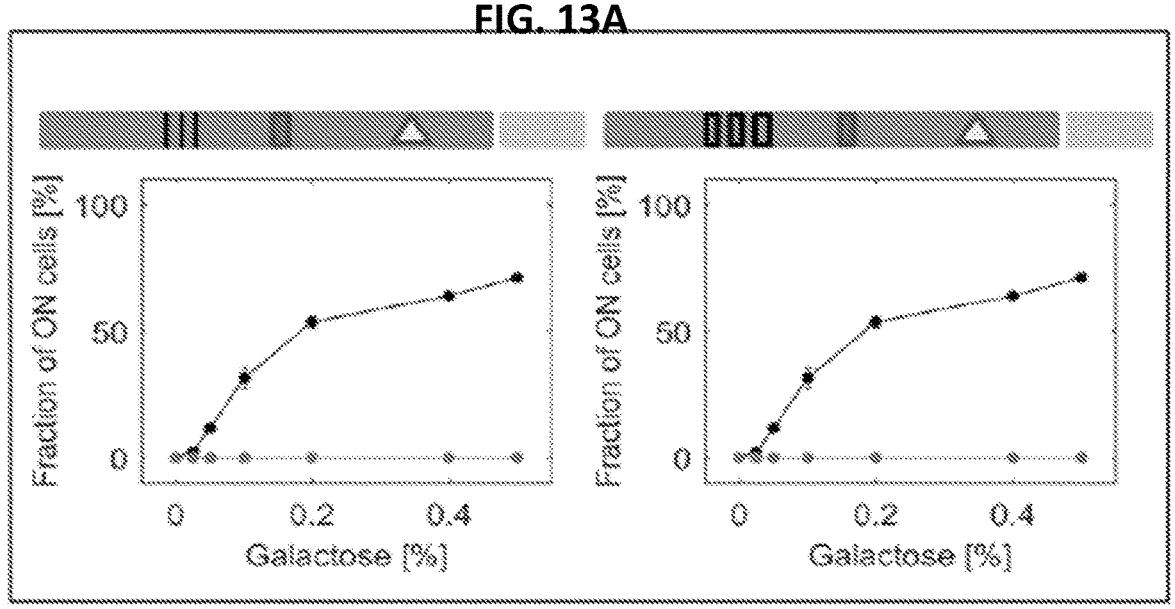
FIGS. 13A-13C are a series of graphs and images demonstrating that the fourth Gal4 binding site in the GAL1 promoter is neither necessary nor sufficient to induce PGAL1-YFP expression. Each horizontal bar indicates one strain and illustrates the specific edits introduced in the GAL1 promoter. The filled boxes are Gal4 binding sites while elimination of a Gal4 binding site by recoding is depicted by an empty box. A triangle indicates the TATA box and the black line indicates the removal of a Gal4 binding site. Wild type data are plotted in black as the reference while the data of each bar-illustrated strain are shown in grey. Each panel depicts either the fraction of ON cells in percent or the mean expression level of ON cells in arbitrary units (a.u.). The mean ON expression level plots only include galactose concentrations at which both strains plotted have at least 5% ON cells. Error bars indicate SEM (N=3 for all wild type data).
Figure 13B:
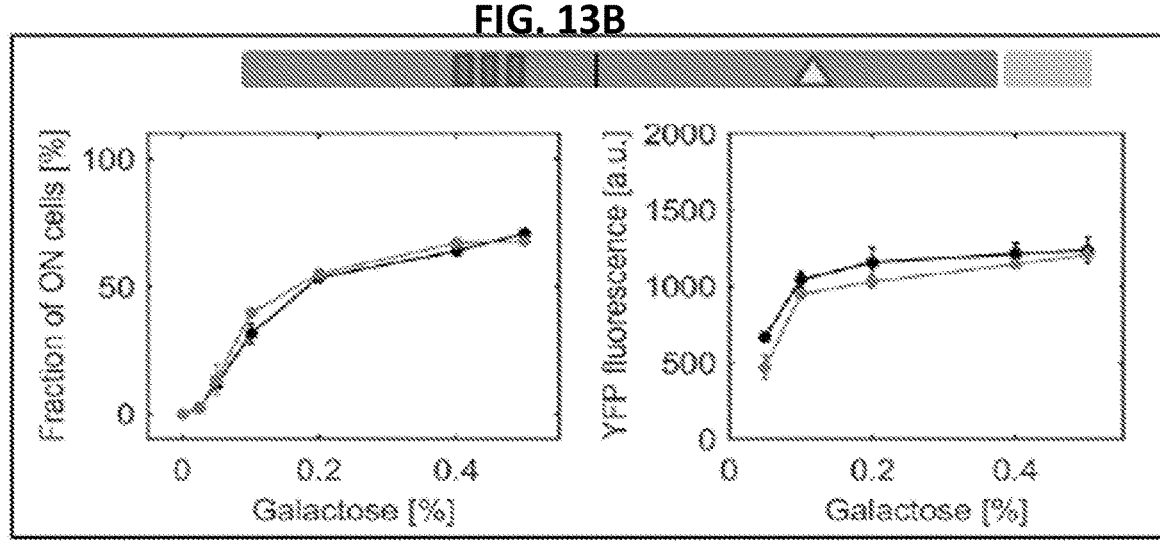
Figure 13C:
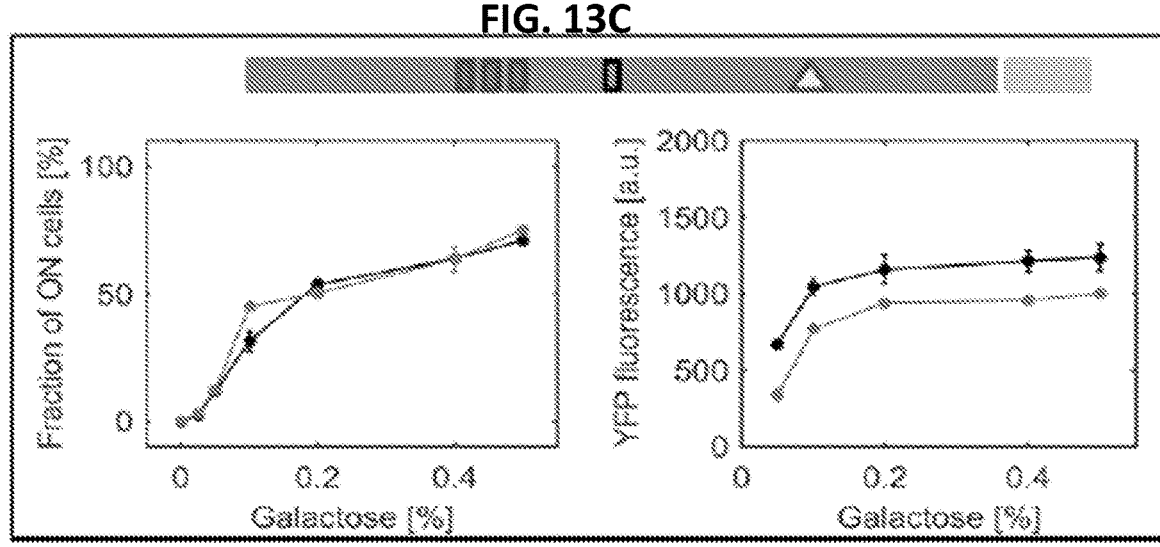

Example 4: Mechanistic Insights into the Differential Activities of the Edited GAL1 Promoters In an effort to further understand how the changes in promoter activity are caused by the addition or removal of Gal4 binding sites, each of the three main Gal4 binding sites on the PGAL1-YFP construct were combinatorially removed or recoded and the resulting promoter activity profiles were measured and compared to the unedited promoter's activity. YFP profiles were examined from the two strains in which all three of the immediately adjacent Gal4 binding sites were removed or recoded. It was discovered that that these strains lacked any YFP expression (FIG. 3A, FIG. 13A). In addition, when the fourth binding site was removed or recoded, the changes did not have any effect on GAL1 activity (FIGS. 13B-13C). These results indicate that the fourth binding site is neither necessary nor sufficient for promoter activity. It was thus concluded that this site was not relevant to the GAL1 promoter's activity and treated it as such for the remainder of this study. The difference of this site from the canonical motif further supports the phenotypically validated conclusion.

Figure 3B:
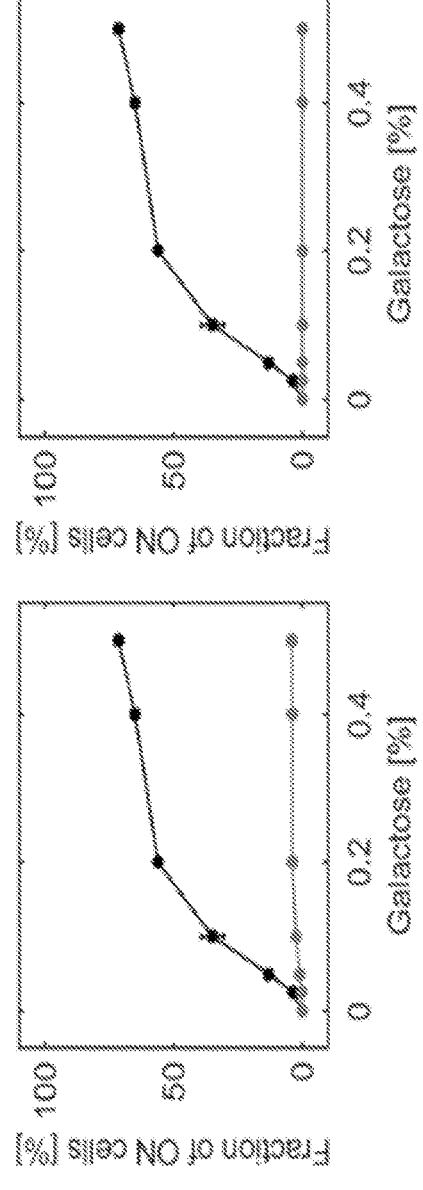
Figure 3C:
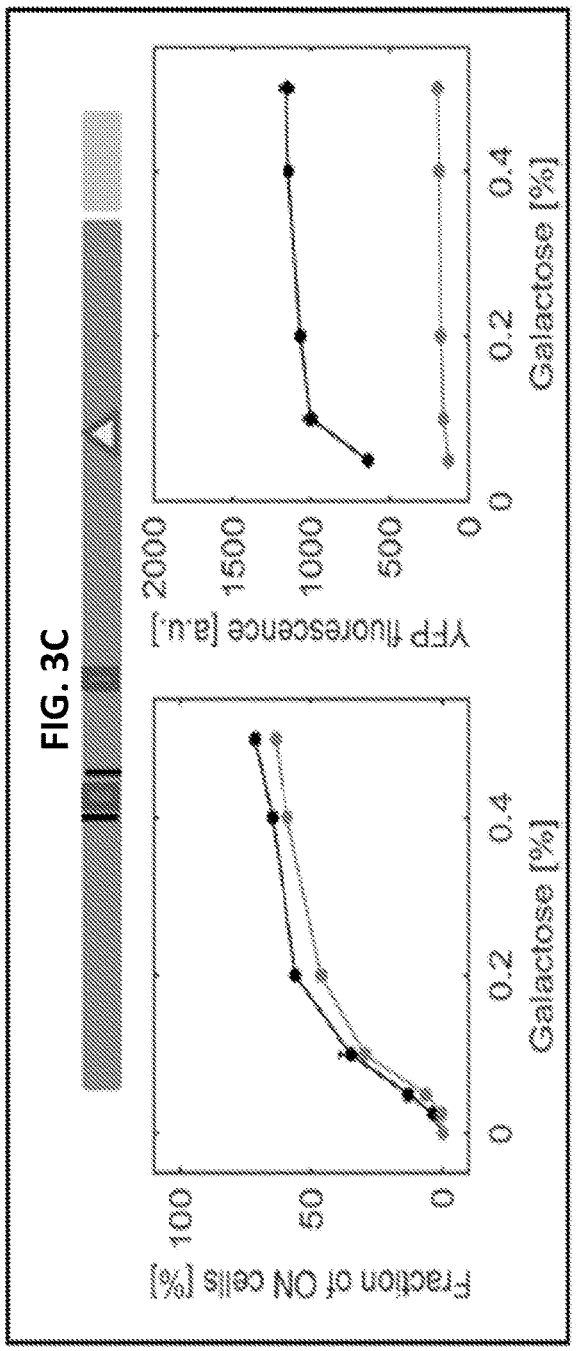
Figure 3D:
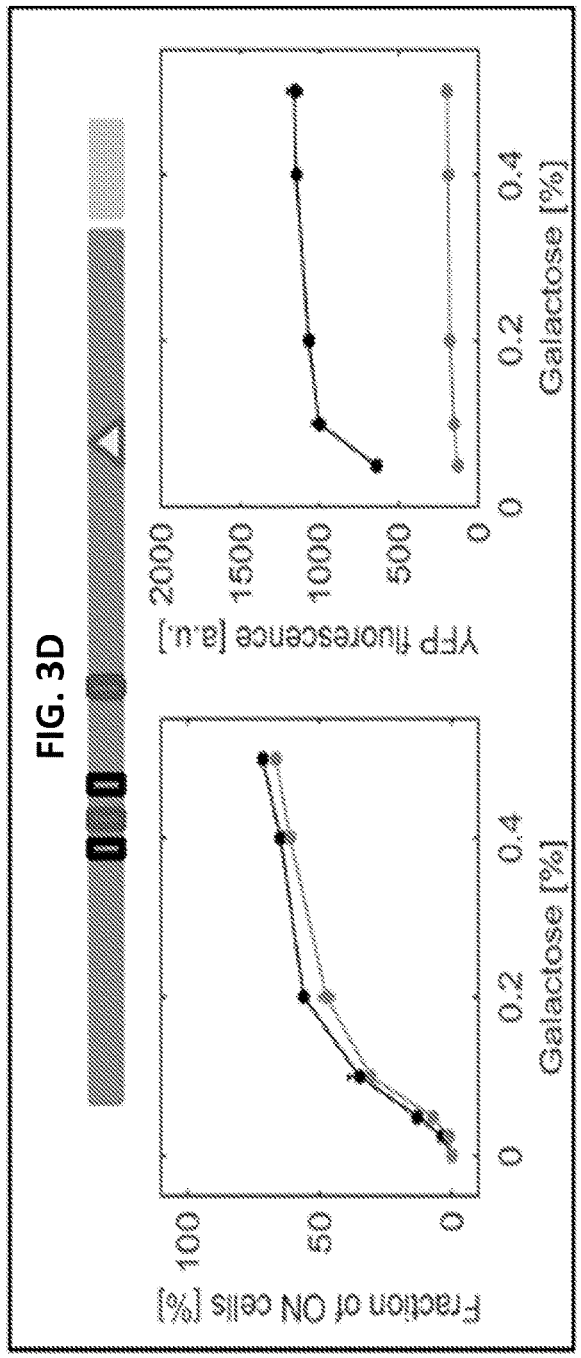
Figure 4A:
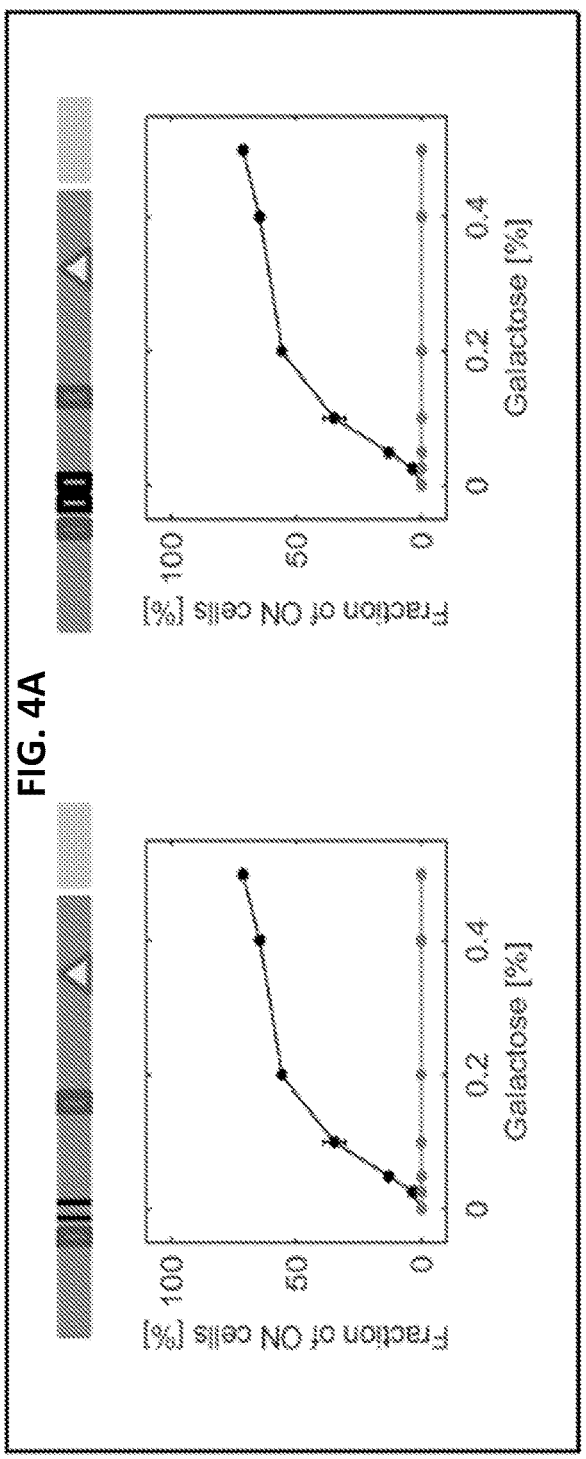
FIGS. 4A-4B are a series of images showing additional GAL1 promoter architectures phenotypically characterized. Each horizontal bar indicates one strain and illustrates the specific edits introduced in the GAL1 promoter. The filled boxes are Gal4 binding sites while removing a Gal4 binding site by recoding is depicted by an empty box. A triangle indicates the TATA box and the black line indicates the removal of a Gal4 binding site.
Figure 4B:
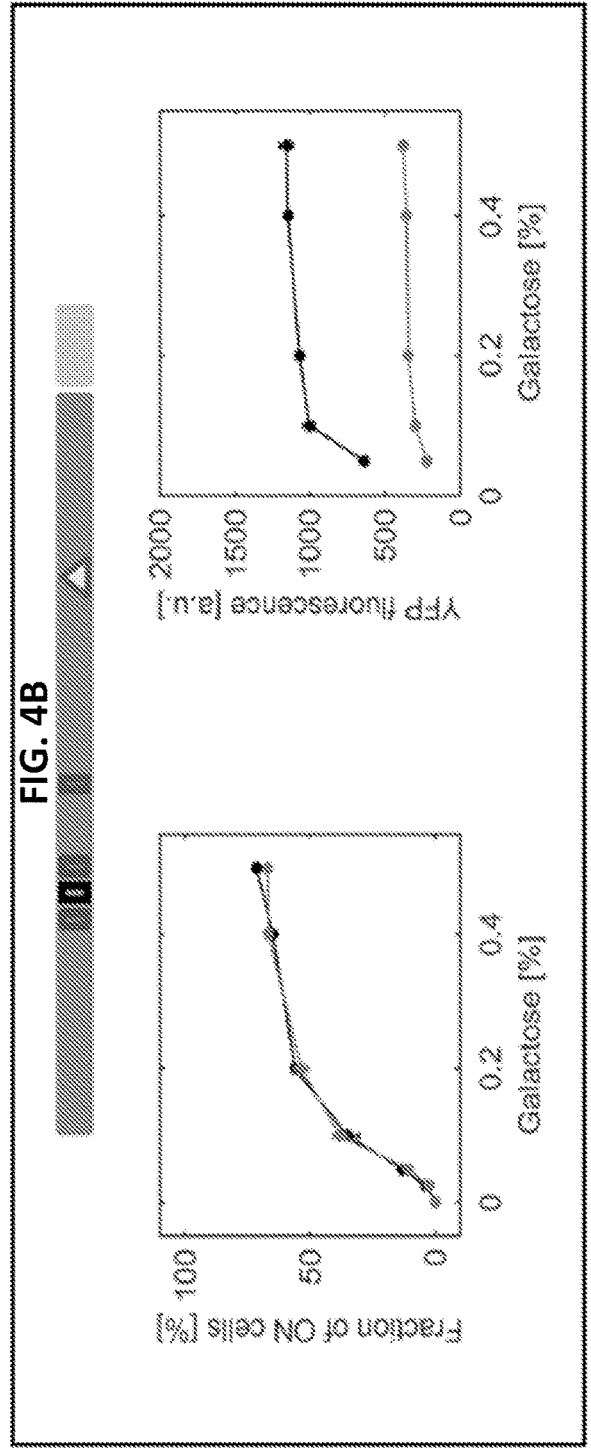

Focusing on the first three canonical Gal4 binding sites, the promoter-edited strains were examined to determine if removing or recoding the first Gal4 binding site (by itself or together with the second site) had an effect on transcriptional activity from the GAL1 promoter. Similar to the results observed by editing the GAL80 promoter (FIGS. 5A-5E), removing or recoding the first site prevented any activity from the promoter despite the presence of the remaining two binding sites (FIG. 3B). More surprising was the observation that recoding both the first and third Gal4 binding sites restored the wild type activity in the promoter in terms of the fraction of ON cells but not in terms of the expression level of the ON state (FIG. 3D). Removing the first and third binding site locations had the same effect (FIG. 8C). Similar phenotypes were also seen for other GAL1 promoter edits (FIGS. 8A-8B). Removing or recoding the third binding site prevented any activity from the promoter despite the presence of the other two binding sites (FIGS. 8A-8B). While the hypothesis that the number of transcription factor binding sites on a promoter is the key determinant of promoter activity was initially appealing, results from three promoter architectures contradicted this idea. Two of these represent promoter designs in which the second and third binding sites had both been either removed or recoded, leaving only the first Gal4 binding site intact (FIG. 4A). According to the binding site number hypothesis, the activity from these two promoters should have been similar to the activity from those promoters carrying only the second Gal4 binding site intact (FIGS. 3C-3D, FIG. 8C). Instead, having only the first Gal4 binding site intact resulted in the abolishment of all activity from the promoter, while having only the second Gal4 binding site resulted in a promoter activity profile matching the wild type in terms of the fraction of ON cells. The other promoter architecture which generated results contradictory to the binding site number hypothesis was the one containing intact first and third Gal4 binding sites with the second site recoded (FIG. 4B). Despite having two functional binding sites, the phenotypic characteristics of this promoter resembled those promoters (FIG. 2D, FIGS.

3C-3D, FIG. 8C) with only one functional binding site. These findings, together with the ones observed from the edited GAL80 promoters (FIGS. 5A-5E), led to the rejection of the hypothesis that the number of transcription factor binding sites was the sole key factor in setting promoter activity levels.

As an alternative hypothesis, in certain embodiments the relative position of the Gal4 binding site(s) and other promoter elements, such as the TATA box, is an important parameter influencing the promoter activity levels. The fact that Gal4 binding site(s) are involved in the looping of DNA for a stable transcriptional initiation provides a mechanistic basis for this hypothesis. Accepting distance between important promoter elements as a key factor does not fully discard potential contributions from the number of binding sites on promoter activity. Indeed, removing a binding site automatically alters the relative distances between promoter elements, meaning that the parameters of binding site number and distance cannot be fully orthogonal. Without wishing to be limited by any theory, when crucial spacing needs between promoter elements are not met, the effects of transcription factor binding site number can be muted due to disruption of the spacing necessary for proper folding of DNA and transcriptional initiation.

Without wishing to be bound by specific theory, the hypothesis based on the relative positioning of promoter elements explains why the two strains with only the left Gal4 binding site intact (FIG. 4A) failed to be inducible. Having only one binding site was not the culprit as having only the middle binding site had produced a wild-type like fraction of ON cells (FIG. 3C-3D, FIG. 8C). This indicates that, compared to the phenotypic effect of the middle binding site, having only the left site increased the distance between the site and downstream promoter elements, leading to the deactivation of the promoter. The relative positioning hypothesis also explains the re-activation of the GAL1 promoter when two Gal4 binding sites are separated by 20 bp (FIG. 4B), as the promoter was inactive when two binding sites were separated by 2 bp (FIG. 3B).

Example 5: Editing the GAL80 Promoter Sequence

To move the phenotypic characterization of the editing approach to the gene network level and to test the approach on the editing of a promoter functioning in its natural location, rational edits were introduced on the endogenous GAL80 promoter that contains a single Gal4 binding site (FIG. 5A, red box). Four strains carrying different edits on the GAL80 promoter were constructed, and the resulting activity of the GAL network was measured using YFP driven by the wild type GAL1 promoter.

In the first strain, a new Gal4 binding site was inserted immediately before the existing one (FIG. 5B) on the GAL80 promoter, while in the second strain the existing base pairs were recoded before the existing Gal4 binding site into a second Gal4 binding site (FIG. 5C), a change doubling the number of binding sites but not increasing the length of the promoter. Both of these strains showed a massive increase in the fraction of ON cells—in the recoded strain, virtually all cells were in the ON state even in the absence of galactose. Since Gal80 is a repressor protein, these findings indicate that the alterations made on the GAL80 promoter greatly reduced or eliminated GAL80 expression, thus allowing GAL1 promoter to be activated in a much larger fraction of cells.

In the third strain, a new Gal4 binding site was added immediately downstream of the existing one (FIG. 5D), while in the fourth strain the existing base pairs were recoded downstream of the existing Gal4 binding site into a second Gal4 binding one (FIG. 5E). The results from the recoded strain (FIG. 5E) resembled the previous two strains discussed above in that the expression of GAL80 seemed to be completely eliminated at all galactose concentrations used. Compared to the unedited strain, the strain with one Gal4 binding site added downstream from the original site showed a reduction in the fraction of ON cells while keeping the mean YFP expression levels of the ON cells to be roughly the same (FIG. 5D). This result indicates higher GAL80 expression levels in this strain compared to wild type. These results suggest that while binding site number is clearly important for setting promoter expression level or strength, it is not the only factor. The location of binding sites within the promoter is also of utmost importance. In one non-limiting example, when two Gal4 binding sites are adjacent to each other (FIGS. 5B-5E), their relative positioning to the other promoter elements determines if transcription proceeds (FIGS. 5D-5E) or is blocked (FIGS. 5B-5C). Studies utilizing single molecule imaging techniques will help elucidate how such transcriptional inactivation occurs.

Example 6: Introducing Simultaneous Edits on the GAL1 and GAL80 Promoters

Figure 6A:
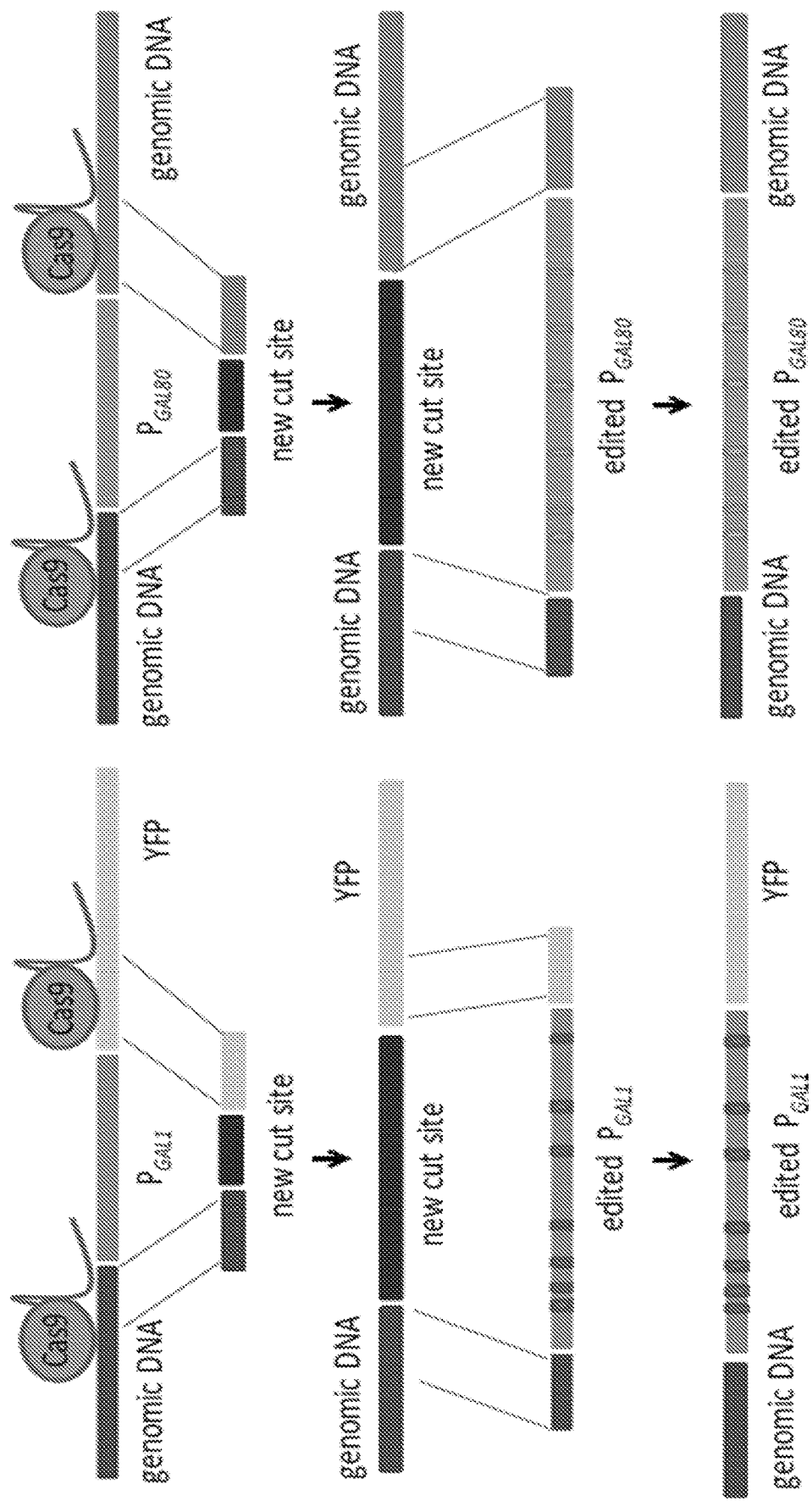

To further investigate the findings and expand the applicability of the method, edits were simultaneously introduced on two different genomic locations: GAL80 promoter at its endogenous location and GAL1 promoter driving YFP at the ho locus. A strain was constructed containing novel targeting and PAM sites replacing both GAL1 and GAL80 promoters. This strain was transformed with a plasmid containing two gRNAs, one for each promoter site, as well as donors carrying the edited promoters (FIG. 6A). To find out the combined efficiency of simultaneous editing at both genome locations, editing efficiency was examined for both locations individually and together. Using targeted sequencing, it was discovered that 76% of the colonies were successfully edited at the GAL1 promoter, 83% were successfully edited at the GAL80 promoter, and 69% were successfully were edited at both locations (FIG. 6B).

To measure the phenotypic consequences of the dual edits, a strain was constructed by combining two specific sets of edits previously introduced on GAL1 (FIG. 2D) and GAL80 (FIG. 5C) promoters. When introduced into the wild type background, the GAL1 promoter edits (the first and second binding site locations recoded) gave rise to ON cell fractions similar to the wild type strain, however, the expression level of the ON state was drastically reduced (FIG. 2D; FIG. 6C). On the other hand, when introduced into the wild type background, the GAL80 promoter edit (recoding a second Gal4 binding site upstream of the original one), led to increases in the fraction of ON cells and ON-state expression levels (FIG. 5C; FIG. 6C). Analyzing the fraction of ON cells in the strain carrying the GAL1 and GAL80 dual edits (FIG. 6C, left panel) showed that the GAL80 edit, which lowered GAL80 protein expression, dictated the phenotype of the dual edit strain; this was consistent with the phenotypic effect of the GAL1 edits being neutral (FIG. 6C, left panel). However, when analyzing the phenotype of mean ON-state expression levels, it was observed that the GAL1 edit, which lowered the GAL1 expression mean (FIG. 2D, right panel), dictated the phenotype of the dual edit strain. This was also consistent with the fact that the phenotypic effect of the GAL80 edits was considerably less intense than that of the GAL1 edit (FIG. 6C, right panel).

Figure 10A:
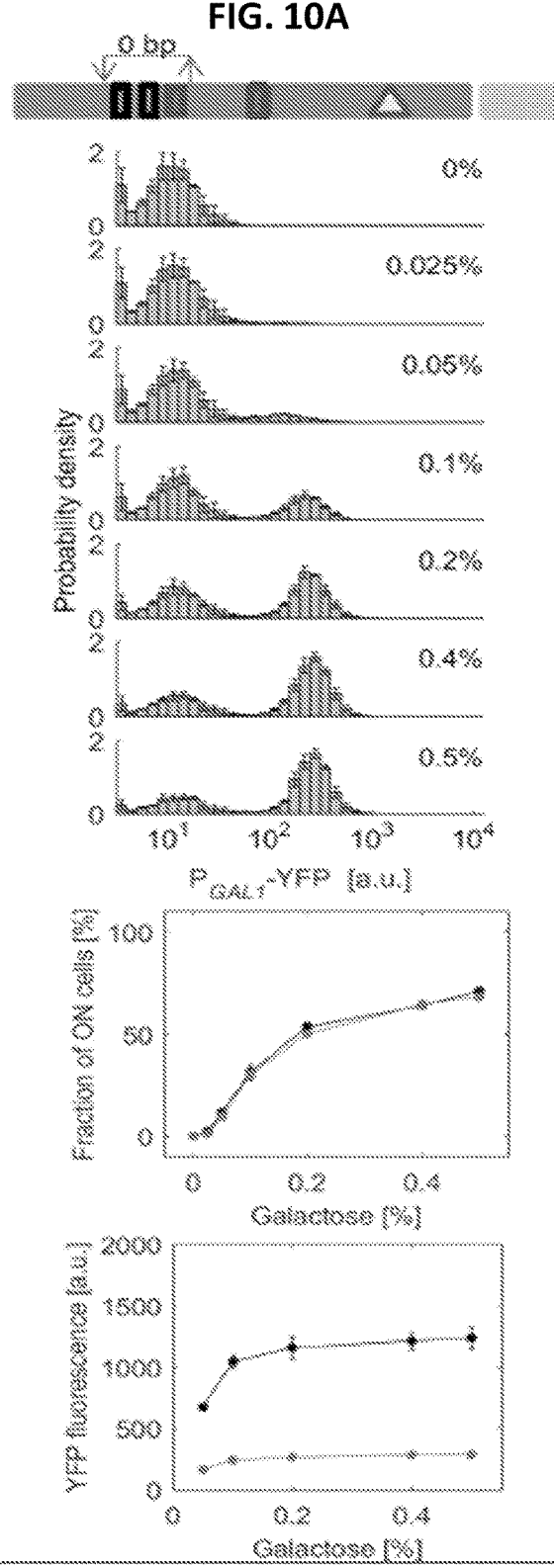
FIGS. 10A-10D are a series of plots and images showing phenotypic characterization of systematic spacing changes in the GAL1 promoter. Each horizontal bar indicates one strain and illustrates the specific edits introduced in the GAL1 promoter. The filled boxes are Gal4 binding sites while removing a Gal4 binding site by recoding is depicted by an empty box. A triangle indicates the TATA box and the black line indicates the removal of a Gal4 binding site. Arrows above the promoter indicate the number and position of base pairs moved from one location within the promoter to another. Wild type data is plotted in black as the reference while the data of each bar-illustrated strain are shown in grey. Histograms show the flow cytometry data at seven concentrations of galactose as indicated from 0% to 0.5%. Each panel depicts either the fraction of ON cells in percent or the mean expression level of the ON cells in arbitrary units (a.u.), reported by the edited $P_{GAL1}$-YFP. The mean ON expression level plots only include galactose concentrations at which both strains plotted have at least 5% ON cells. Error bars indicate SEM (N=3).
Figure 10B:
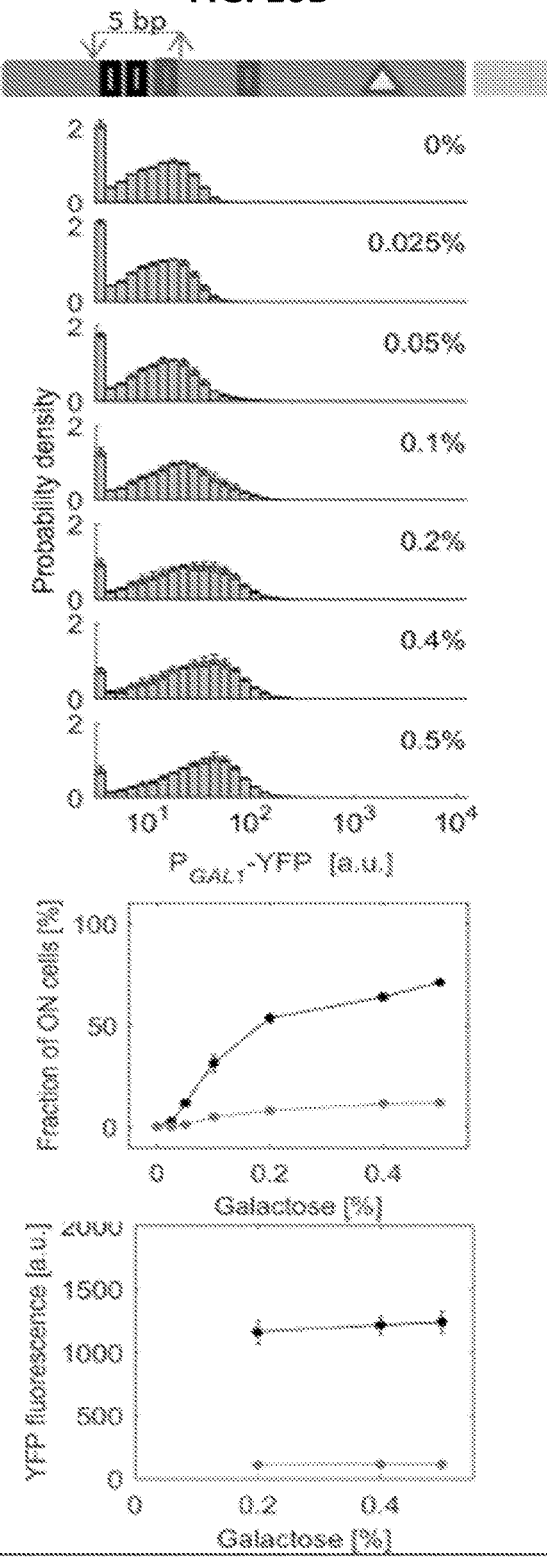
Figure 10C:
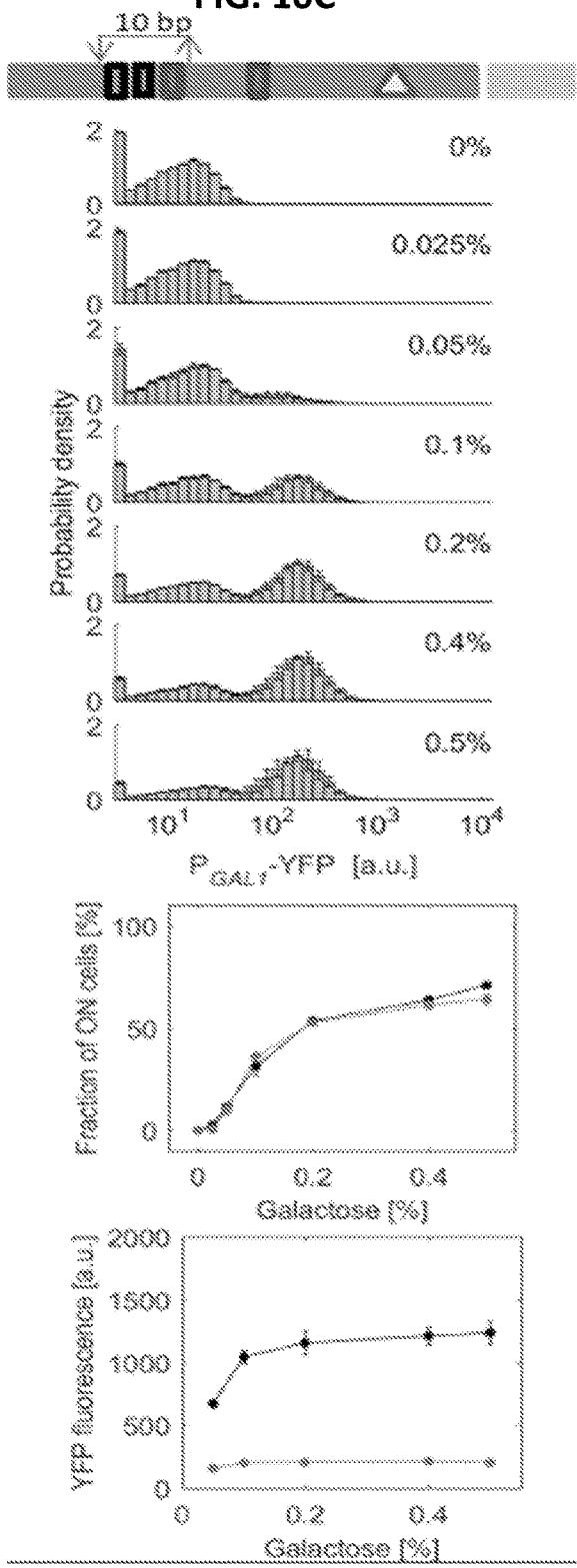

Example 7: Systematic Alterations of Distance Between Specific Promoter Elements To further confirm the hypothesis that the spacing of key promoter elements can have a drastic impact on promoter activity, three additional strains were constructed in which the distance between the third Gal4 binding site and the TATA box was shortened by 5, 10, or 17 base pairs. This was done by moving the 5, 10, or 17 bp-long GAL1 promoter region immediately downstream of the third Gal4 binding site to a location immediately upstream of the first Gal4 binding site. These strains were built off of the strain seen in FIG. 2D, as having only one canonical binding site allowed easier interpretation of the results. The resulting three strains therefore had the single intact Gal4 binding site moved 5, 10, or 17 bp closer to other promoter elements, such as the transcription start site (TSS) and the TATA box, and moved the same distance away from the 5' end of the promoter. The strain in which the Gal4 binding site was moved 5 bp closer to the TSS and TATA box (FIG. 10B) displayed an almost complete lack of promoter activity. In contrast, its parent strain (FIG. 2D and FIG. 10A) displayed a fraction of ON cells virtually identical to that of the wild type. However, the strain in which the Gal4 binding site was moved 10 bp closer to the TSS and TATA (FIG. 10C) closely resembled its parent (FIG. 10A). Even more interestingly, the strain in which the Gal4 binding site was moved 17 bp closer to the TSS and TATA box (FIG. 10D) had a similar fraction of ON cells to both its parent and to the wild type strain, but had a much higher mean expression level than its parent, even higher than the wild type.

Figure 10D:
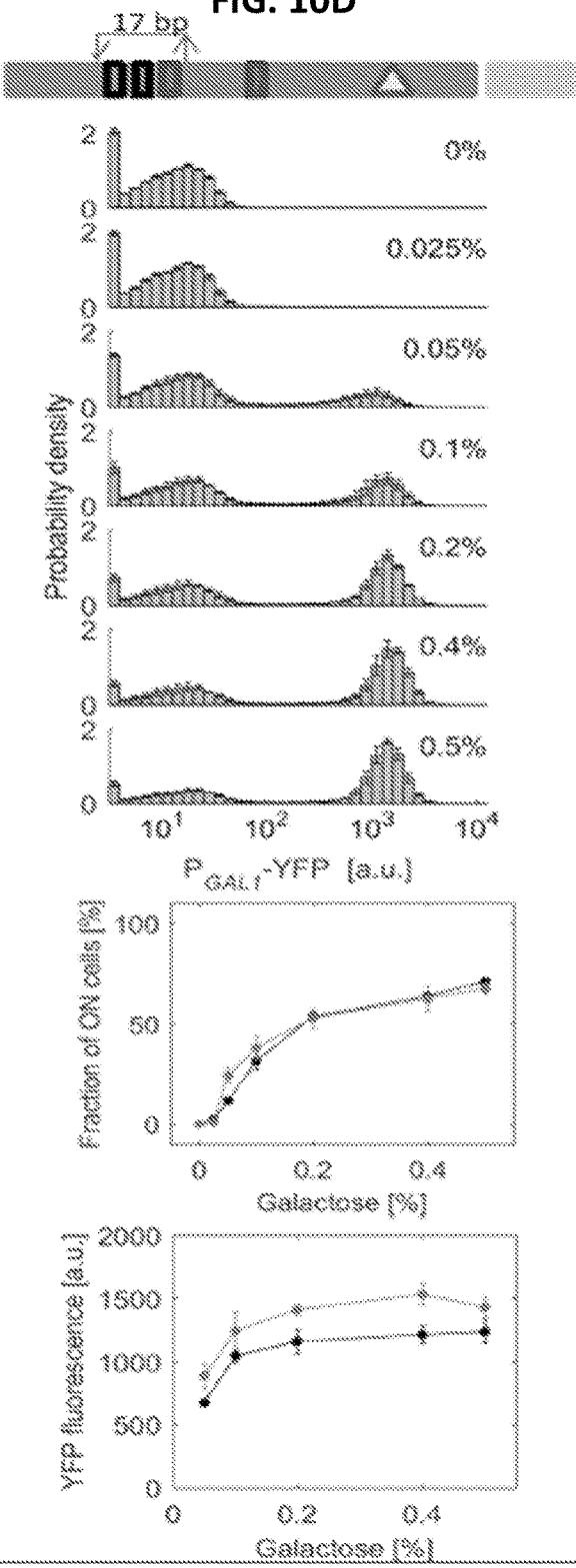
Figure 12:
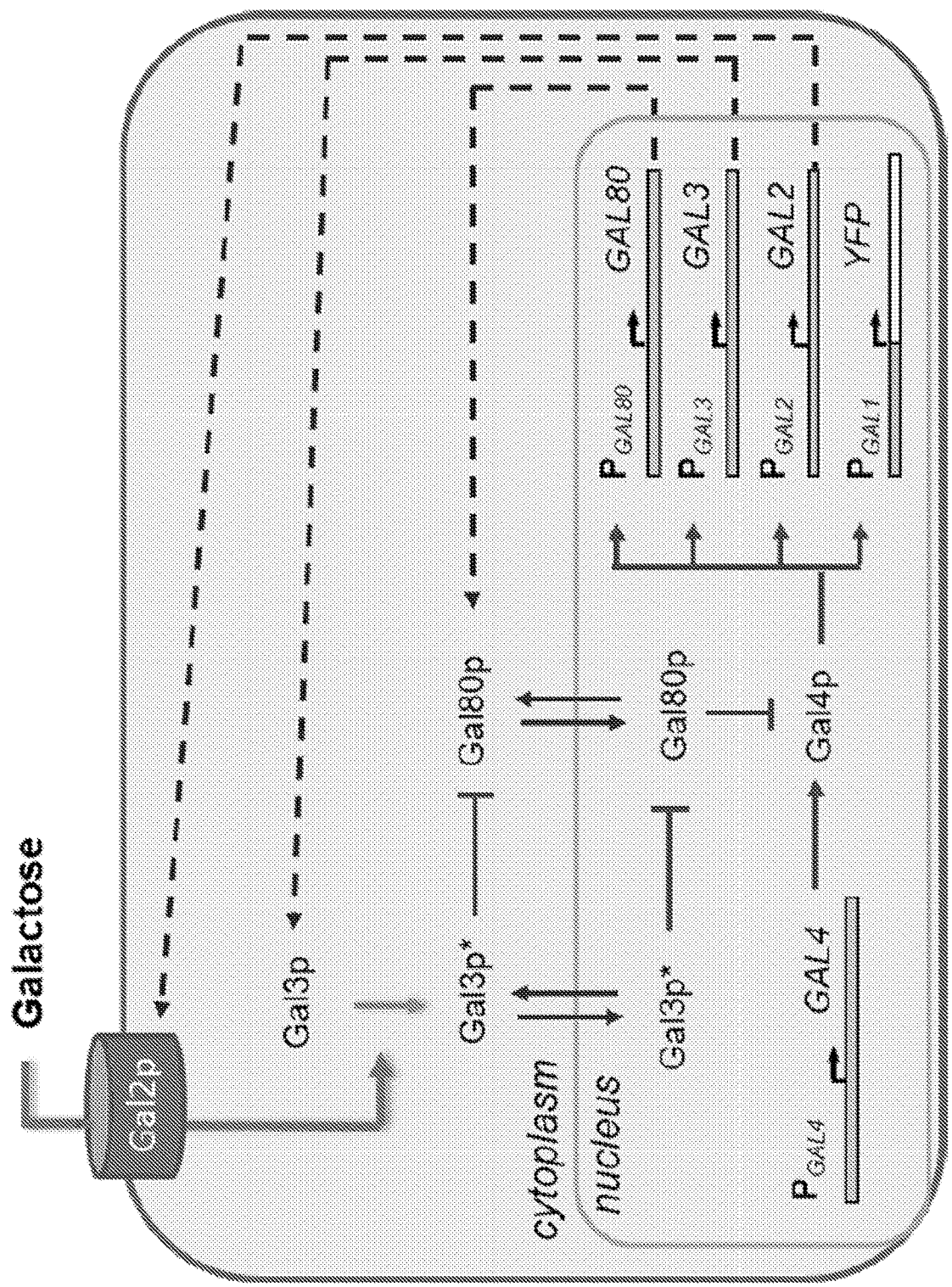
FIG. 12 is a schematic depicting the yeast galactose regulatory network. Related to FIG. 2A. Galactose network architecture built by the regulatory genes. The solid black lines denote the four-stage signaling cascade. The galactose-bound state of Gal3p is denoted by Gal3p*. Pointed and blunt arrows reflect activation and inhibition, respectively. The dashed arrows denote feedback loops established by Gal2p, Gal3p and Gal80p. The constitutive expression of the Gal4 proteins is also depicted. The double arrows denote translocation of Gal80p and Gal3p* between cytoplasm and nucleus. Acting in parallel to the main inducer of the network, Gal3p, the relatively weak network inducer Gal1p, its galactose-bound form Gal1p*, and the positive-feedback loop it mediates are not drawn due to space constraints.

These results show that the spacing between various promoter elements is crucial for promoter activity. The stark difference among strains with their Gal4 binding sites located only a few base pairs closer to or farther from the TSS and TATA box illustrates that a change in the relative position of various promoter elements is capable of almost completely eliminating activity from a promoter (FIG. 10B), keeping activity almost exactly the same (FIG. 10C), or massively increasing expression compared to the parent strain (FIG. 10D). The changes made to the number of Gal4 binding sites also resulted in small spacing changes which were originally ignored, such as those in FIG. 5C (right panel), but without wishing to be bound by specific theory, are likely to be the cause of the loss of expression from the promoter. Without wishing to be bound by specific theory, these phenotypic changes can be explained by the positioning of the binding sites on the DNA helix itself. A helical turn of the DNA is known to be ~10.5 bp, so a change of 5 bp should place the Gal4 binding sites on the opposite side of the DNA compared to the original, potentially resulting in a loss of interaction between the DNA bound-Gal4 and the transcriptional machinery. However, a change of 10 bp would bring the Gal4-bound site back to its original position in three-dimensional space, potentially explaining why expression is restored. The increased expression level resulting from the 17 bp shortening is harder to fully explain as the 17 bp change is expected to lead to both a partial helical turn and a change in position along the DNA strand. However, this result still reinforces the main hypothesis that the spacing of key promoter elements is critical for setting specific promoter activity levels.

While there may still be a number of unknown factors influencing the overall promoter activity from each new configuration of the GAL1 promoter, an initial model was elucidated (FIGS. 11A-11D) based on strains in which the third Gal4 binding site is systematically moved towards the TSS and TATA box. The wild type promoter architecture carries three canonical binding sites on which Gal4 proteins bind. The presence of transcriptional mediators induces the bending of the Gal4-bound DNA in order to facilitate stable assembly of the transcriptional machinery including RNA polymerase (FIG. 11A). On a promoter with a single active binding site, Gal4 binds to that site and interacts with the transcriptional machinery, causing promoter activation but with a lower expression level (FIG. 11B). When the single Gal4 binding site is moved 5 bp closer to the TATA box, the site-bound Gal4 protein is rotated almost a full half turn around the DNA helix, causing all expression to be lost, likely due to the loss of interactions between Gal4 and the transcriptional machinery on the promoter (FIG. 11C). However, when the single binding site is moved 10 bp closer to the TATA box, the site-bound Gal4 protein is rotated almost full circle around the DNA helix, leading to promoter activity levels very similar to the levels seen without the 10 bp change. This result indicates that the 10 bp move restores the interaction of the Gal4 protein with the transcriptional machinery (FIG. 11D). This model explains why small changes in spacing caused loss of activity from the GAL1 promoter in many of the edited promoters examined in this study.

In the present study, a novel application of the CRISPR/Cas9 genome editing technology was introduced. This technique allows truly scarless editing of large genomic regions in live yeast cells by preserving endogenous PAM sites. As demonstrated herein, by removing the region of interest and then replacing it with its edited version, any number of edits can be made to a genomic region. Constructing an intermediate strain by introducing a novel PAM site is necessary for completely scarless editing. This is due to the inability to introduce donor oligonucleotides retaining the original PAM sites which are present outside of the region to edit. If donors with the original PAM sites were used, the CRISPR machinery would not be able to differentiate between the editing donor and the to-be-edited genome and would cut both. The use of this method to overcome this significant obstacle is a major advantage over any other in vivo editing method for sensitive genomic regions.

The method presented herein can be extended to many other organisms and widely used in a broad range of fields and applications, including directed evolution performed in vivo. There is currently no easy method to create synthetically modified organisms containing libraries of mutations at specific regions in their genome. Such an ability would greatly enrich the technique of directed evolution, as edited genes could be expressed in their native loci and without copy number variations, both of which have been inevitable disadvantages of the traditional plasmid-based directed evolution technique.

Using the scarless genome editing method disclosed herein, previously unknown characteristics of the canonical GAL1 and GAL80 promoters, which are commonly used not only in yeast studies but also in many other eukaryotic organisms, were elucidated. Yeast strains were constructed with edited promoters and the effect of transcription factor binding site number and location was examined in vivo. Several surprising results recited herein provide important insights into a more comprehensive understanding of genotype-phenotype relationships in eukaryotes. For example, having two Gal4 binding sites immediately adjacent to each other did not result in promoter activation even in high concentrations of galactose, while promoters with either one or three Gal4 binding sites immediately adjacent to each other had normal promoter activation. When the two Gal4 binding sites were separated by only 20 bp, the promoter was still functional in an activity pattern similar to the wild type. This pattern held true when new Gal4 binding sites were added upstream of the existing site on the GAL80 promoter, but actually increased promoter activation when added downstream. Obtained using the marker-free, precise, scarless genome editing technique of the present invention, results from this study undoubtedly reinforce the idea that the relative positioning of promoter elements is of great importance to promoter activity in live single cells. Simply adding transcription factor binding sites to a promoter can have nonlinear consequences for transcriptional activation instead of enhancing gene expression.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of performing scarless genome editing in an isolated eukaryotic cell comprising a cell genome, the method comprising:
   a. introducing into the cell a catalytically active, human codon optimized S. pyogenes Cas9, a first guide RNA (gRNA), a second gRNA, and a first polynucleotide;
      wherein the first gRNA comprises a nucleotide sequence that is complementary to a cell genome sequence that is upstream of a first genomic region of interest;
      wherein the second gRNA comprises a nucleotide sequence that is complementary to a cell genome sequence that is downstream of the first genomic region of interest;
      wherein the first polynucleotide comprises a nucleotide sequence that is homologous to a cell genome sequence upstream and adjacent to the nucleotide sequence targeted by the first gRNA, a nucleotide sequence comprising a given CRISPR cut site, and a nucleotide sequence that is homologous to a cell genome sequence downstream and adjacent to the nucleotide sequence targeted by the second gRNA;
      wherein the first genomic region of interest is excised from the cell genome and replaced in the cell genome with the first polynucleotide; and
   b. introducing into the cell a catalytically active, human codon optimized S. pyogenes Cas9, a third gRNA, and a second polynucleotide;
      wherein the third gRNA comprises a nucleotide sequence that is complementary to the first polynucleotide;
      wherein the second polynucleotide comprises a nucleotide sequence that is homologous to a cell genome sequence upstream and adjacent to the first polynucleotide, a nucleotide sequence that is a second genomic region of interest, and a nucleotide sequence that is homologous to a cell genome sequence downstream and adjacent to the first polynucleotide; and
      wherein the first polynucleotide is excised from the cell genome and replaced in the cell genome with the second polynucleotide.

2. The method of claim 1, wherein the first genomic region of interest comprises a promoter sequence.

3. The method of claim 1, wherein the first genomic region of interest comprises a non-coding sequence.

4. The method of claim 1, wherein the first genomic region of interest comprises a coding sequence.

5. The method of claim 1, wherein the first genomic region of interest comprises a DNA sequence.

6. The method of claim 1, wherein the first genomic region of interest comprises an RNA sequence.

7. The method of claim 1, wherein the nucleotide sequence comprising a given CRISPR cut site comprises a protospacer adjacent motif (PAM) sequence.

8. The method of claim 7, wherein the PAM sequence comprises 5'-NGG-3'.

9. The method of claim 1, wherein the eukaryotic cell is selected from the group consisting of a mammalian cell, a human cell, and a yeast cell.

10. The method of claim 1, further comprising editing a third genomic region of interest wherein the editing comprises:

a. introducing into the cell a catalytically active, human codon optimized *S. pyogenes* Cas9, a fourth guide RNA (gRNA), a fifth gRNA, and a third polynucleotide;
  - wherein the fourth gRNA comprises a nucleotide sequence that is complementary to a cell genome sequence that is upstream of the third genomic region of interest;
  - wherein the fifth gRNA comprises a nucleotide sequence that is complementary to a cell genome sequence that is downstream of the third genomic region of interest;
  - wherein the third polynucleotide comprises a nucleotide sequence that is homologous to a cell genome sequence upstream and adjacent to the nucleotide sequence targeted by the fourth gRNA, a nucleotide sequence comprising a given CRISPR cut site, and a nucleotide sequence that is homologous to a cell genome sequence downstream and adjacent to the nucleotide sequence targeted by the fifth gRNA;
  - wherein the third genomic region of interest is excised from the cell genome and replaced in the cell genome with the third polynucleotide; and b. introducing into the cell a catalytically active, human codon optimized *S. pyogenes* Cas9, a sixth gRNA, and a fourth polynucleotide;
  - wherein the sixth gRNA comprises a nucleotide sequence that is complementary to the third polynucleotide;
  - wherein the fourth polynucleotide comprises a nucleotide sequence that is homologous to a cell genome sequence upstream and adjacent to the third polynucleotide, a nucleotide sequence that is a fourth genomic region of interest, and a nucleotide sequence that is homologous to a cell genome sequence downstream and adjacent to the third polynucleotide; and
  - wherein the third polynucleotide is excised from the cell genome and replaced in the cell genome with the fourth polynucleotide.

11. The method of claim 1, further comprising wherein the method is multiplexed by editing at least one additional genomic region of interest.

\* \* \* \* \*

SEQUENCE LISTING

<160> NUMBER OF SEQ ID NOS: 27

<210> SEQ ID NO 1
<211> LENGTH: 668
<212> TYPE: DNA
<213> ORGANISM: Artificial sequence
<220> FEATURE:
<223> OTHER INFORMATION: Artificially synthesized

<400> SEQUENCE: 1

```
ttatattgaa ttttcaaaaa ttcttacttt tttttttggat ggacgcaaag aagtttaata      60
atcatattac atggcattac caccatatac atatccatat ctaatcttac ttatatgttg     120
tggaaatgta aagagcccca ttatcttagc ctaaaaaaac cttctctttg gaactttcag     180
taatacgctt aactgctcat tgctatattg aagtacggat tagaagccgc cgagcgggcg     240
acagccctcc gacggaagac tctcctccgt gcgtcctcgt cttaccggt cgcgttcctg      300 aaacgcagat gtgcctcgcg ccgcactgct ccgaacaata aagattctac aatactagct     360
tttatggtta tgaagaggaa aaattggcag taacctggcc ccacaaacct tcaaattaac     420
gaatcaaatt aacaaccata ggatgataat gcgattagtt ttttagcctt atttctgggg     480
taattaatca gcgaagcgat gatttttgat ctattaacag atatataaat ggaaaagctg     540
cataaccact ttaactaata ctttcaacat tttcagtttg tattacttct tattcaaatg     600
tcataaaagt atcaacaaaa aattgttaat atacctctat actttaacgt caaggagaaa     660
aaactata                                                             668
```

<210> SEQ ID NO 2
<211> LENGTH: 283
<212> TYPE: DNA
<213> ORGANISM: Artificial sequence
<220> FEATURE:
<223> OTHER INFORMATION: Artificially synthesized

<400> SEQUENCE: 2

```
atggcgcaag ttttccgctt tgtaatatat atttataccc ctttcttctc tcccctgcaa      60
tataatagtt taattctaat attaataata tcctatattt tcttcattta ccggcgcact     120
ctcgcccgaa cgacctcaaa atgtctgcta cattcataat aaccaaaagc tcataacttt     180
tttttttgaa cctgaatata tatacatcac atatcactgc tggtccttgc cgaccagcgt     240
atacaatctc gatagttggt ttcccgttct ttccactccc gtc                       283
```

<210> SEQ ID NO 3

<211> LENGTH: 651
<212> TYPE: DNA
<213> ORGANISM: Artificial sequence
<220> FEATURE:
<223> OTHER INFORMATION: Artificially synthesized

<400> SEQUENCE: 3

```
ttatattgaa ttttcaaaaa ttcttacttt tttttttggat ggacgcaaag aagtttaata      60
atcatattac atggcattac caccatatac atatccatat ctaatcttac ttatatgttg     120
tggaaatgta aagagcccca ttatcttagc ctaaaaaaac cttctctttg gaactttcag     180
taatacgctt aactgctcat tgctatattg aagtaagcgg gcgacagccc tccgacggaa     240
gactctcctc cgtgcgtcct cgtcttcacc ggtcgcgttc ctgaaacgca gatgtgcctc     300
gcgccgcact gctccgaaca ataaagattc tacaatacta gcttttatgg ttatgaagag     360
gaaaaattgg cagtaacctg ccccacaaa ccttcaaatt aacgaatcaa attaacaacc      420
ataggatgat aatgcgatta gttttttagc cttatttctg gggtaattaa tcagcgaagc     480
gatgattttt gatctattaa cagatatata aatggaaaag ctgcataacc acttaactaa    540
atactttcaa cattttcagt ttgtattact tcttattcaa atgtcataaa agtatcaaca     600
aaaaattgtt aatatacctc tatactttaa cgtcaaggag aaaaaactat a              651
```

<210> SEQ ID NO 4
<211> LENGTH: 617
<212> TYPE: DNA
<213> ORGANISM: Artificial sequence
<220> FEATURE:
<223> OTHER INFORMATION: Artificially synthesized

<400> SEQUENCE: 4

```
ttatattgaa ttttcaaaaa ttcttacttt tttttttggat ggacgcaaag aagtttaata      60
atcatattac atggcattac caccatatac atatccatat ctaatcttac ttatatgttg     120
tggaaatgta aagagcccca ttatcttagc ctaaaaaaac cttctctttg gaactttcag     180
taatacgctt aactgctcat tgctatattg aagtaagatg cgtcctcgtc ttcaccggtc     240
gcgttcctga acgcagatg tgcctcgcgc cgcactgctc cgaacaataa agattctaca     300
atactagctt ttatggttat gaagaggaaa aattggcagt aacctggccc cacaaaacctt    360
caaattaacg aatcaaatta acaaccatag gatgataatg cgattagttt tttagcctta    420
tttctggggt aattaatcag cgaagcgatg attttttgatc tattaacaga tatataaatg    480
gaaaagctgc ataaccactt aactaatac tttcaacatt ttcagtttgt attacttctt      540
attcaaatgt cataaaagta tcaacaaaaa attgttaata tacctctata ctttaacgtc    600
aaggagaaaa aactata                                                    617
```

<210> SEQ ID NO 5
<211> LENGTH: 668
<212> TYPE: DNA
<213> ORGANISM: Artificial sequence
<220> FEATURE:
<223> OTHER INFORMATION: Artificially synthesized

<400> SEQUENCE: 5

```
ttatattgaa ttttcaaaaa ttcttacttt tttttttggat ggacgcaaag aagtttaata      60
atcatattac atggcattac caccatatac atatccatat ctaatcttac ttatatgttg     120
tggaaatgta aagagcccca ttatcttagc ctaaaaaaac cttctctttg gaactttcag     180
taatacgctt aactgctcat tgctatattg aagtatctat tagaagccga aaagcgggcg     240
```

| | |
|---|---|
| acagccctcc gacggaagac tctcctccgt gcgtcctcgt cttcaccggt cgcgttcctg | 300 |
| aaacgcagat gtgcctcgcg ccgcactgct ccgaacaata aagattctac aatactagct | 360 |
| tttatggtta tgaagaggaa aaattggcag taacctggcc ccacaaacct tcaaattaac | 420 |
| gaatcaaatt aacaaccata ggatgataat gcgattagtt ttttagcctt atttctgggg | 480 |
| taattaatca gcgaagcgat gattttgat ctattaacag atatataaat ggaaaagctg | 540 |
| cataaccact ttaactaata cttcaacat tttcagtttg tattacttct tattcaaatg | 600 |
| tcataaaagt atcaacaaaa aattgttaat atacctctat actttaacgt caaggagaaa | 660 |
| aaactata | 668 |

<210> SEQ ID NO 6
<211> LENGTH: 668
<212> TYPE: DNA
<213> ORGANISM: Artificial sequence
<220> FEATURE:
<223> OTHER INFORMATION: Artificially synthesized

<400> SEQUENCE: 6

| | |
|---|---|
| ttatattgaa ttttcaaaaa ttcttacttt tttttttggat ggacgcaaag aagtttaata | 60 |
| atcatattac atggcattac caccatatac atatccatat ctaatcttac ttatatgttg | 120 |
| tggaaatgta aagagcccca ttatcttagc ctaaaaaaac cttctctttg gaactttcag | 180 |
| taatacgctt aactgctcat tgctatattg aagtatctat tagaagccga aaagtttgcg | 240 |
| acagcccttt tacggaagac tctcctccgt gcgtcctcgt cttcaccggt cgcgttcctg | 300 |
| aaacgcagat gtgcctcgcg ccgcactgct ccgaacaata aagattctac aatactagct | 360 |
| tttatggtta tgaagaggaa aaattggcag taacctggcc ccacaaacct tcaaattaac | 420 |
| gaatcaaatt aacaaccata ggatgataat gcgattagtt ttttagcctt atttctgggg | 480 |
| taattaatca gcgaagcgat gattttgat ctattaacag atatataaat ggaaaagctg | 540 |
| cataaccact ttaactaata cttcaacat tttcagtttg tattacttct tattcaaatg | 600 |
| tcataaaagt atcaacaaaa aattgttaat atacctctat actttaacgt caaggagaaa | 660 |
| aaactata | 668 |

<210> SEQ ID NO 7
<211> LENGTH: 668
<212> TYPE: DNA
<213> ORGANISM: Artificial sequence
<220> FEATURE:
<223> OTHER INFORMATION: Artificially synthesized

<400> SEQUENCE: 7

| | |
|---|---|
| ttatattgaa ttttcaaaaa ttcttacttt tttttttggat ggacgcaaag aagtttaata | 60 |
| atcatattac atggcattac caccatatac atatccatat ctaatcttac ttatatgttg | 120 |
| tggaaatgta aagagcccca ttatcttagc ctaaaaaaac cttctctttg gaactttcag | 180 |
| taatacgctt aactgctcat tgctatattg aagtatctat tagaagccga aaagtttgcg | 240 |
| acagcccttt taataaagac tctccttatt gcgtcctcgt cttcaccggt cgcgttcctg | 300 |
| aaacgcagat gtgcctcgcg ccgcactgct ccgaacaata aagattctac aatactagct | 360 |
| tttatggtta tgaagaggaa aaattggcag taacctggcc ccacaaacct tcaaattaac | 420 |
| gaatcaaatt aacaaccata ggatgataat gcgattagtt ttttagcctt atttctgggg | 480 |
| taattaatca gcgaagcgat gattttgat ctattaacag atatataaat ggaaaagctg | 540 |

```
cataaccact ttaactaata cttteaacat tttcagtttg tattacttct tattcaaatg    600
tcataaaagt atcaacaaaa aattgttaat atacctctat actttaacgt caaggagaaa    660
aaactata                                                             668
```

<210> SEQ ID NO 8
<211> LENGTH: 304
<212> TYPE: DNA
<213> ORGANISM: Artificial sequence
<220> FEATURE:
<223> OTHER INFORMATION: Artificially synthesized

<400> SEQUENCE: 8

```
atggcgcaag ttttccgctt tgtaatatat atttataccc ctttcttctc tcccctgcaa     60
tataatagtt taattctaat attaataata tcctatattt tcttcattta ctacggatta    120
gaagccgccg agcggcgcac tctcgcccga acgacctcaa aatgtctgct acattcataa    180
taaccaaaag ctcataactt ttttttttga acctgaatat atacatcca catatcactg    240 ctggtccttg ccgaccagcg tatacaatct cgatagttgg tttcccgttc tttccactcc    300
cgtc                                                                 304
```

<210> SEQ ID NO 9
<211> LENGTH: 303
<212> TYPE: DNA
<213> ORGANISM: Artificial sequence
<220> FEATURE:
<223> OTHER INFORMATION: Artificially synthesized

<400> SEQUENCE: 9

```
atggcgcaag ttttccgctt tgtaatatat atttataccc ctttcttctc tcccctgcaa     60
tataatagtt taattctaat attaataata tcctatattt tcttcattta ccggcgcact    120
ctcgcccgac ggaagactct cctccgtgaa cgacctcaaa atgtctgcta cattcataat    180
aaccaaaagc tcataacttt tttttttgaa cctgaatata tacatcac atatcactgc    240 tggtccttgc cgaccagcgt atacaatctc gatagttggt ttcccgttct ttccactccc    300
gtc                                                                  303
```

<210> SEQ ID NO 10
<211> LENGTH: 283
<212> TYPE: DNA
<213> ORGANISM: Artificial sequence
<220> FEATURE:
<223> OTHER INFORMATION: Artificially synthesized

<400> SEQUENCE: 10

```
atggcgcaag ttttccgctt tgtaatatat atttataccc ctttcttctc tcccctgcaa     60
tataatagtt taattctaat attaataata tacggattag aagccgccga gcggcgcact    120
ctcgcccgaa cgacctcaaa atgtctgcta cattcataat aaccaaaagc tcataacttt    180
tttttttgaa cctgaatata tacatcacg atatcactgc tggtccttgc cgaccagcgt    240
atacaatctc gatagttggt ttcccgttct ttccactccc gtc                      283
```

<210> SEQ ID NO 11
<211> LENGTH: 283
<212> TYPE: DNA
<213> ORGANISM: Artificial sequence
<220> FEATURE:
<223> OTHER INFORMATION: Artificially synthesized

<400> SEQUENCE: 11

```
atggcgcaag ttttccgctt tgtaatatat atttataccc ctttcttctc tccectgcaa      60 tataatagtt taattctaat attaataata tcctatattt tcttcattta ccggcgcact     120
ctcgcccgac ggaagactct cctccgtgta cattcataat aaccaaaagc tcataacttt     180
tttttttgaa cctgaatata tatacatcac atatcactgc tggtccttgc cgaccagcgt     240
atacaatctc gatagttggt ttcccgttct ttccactccc gtc                       283

<210> SEQ ID NO 12
<211> LENGTH: 668
<212> TYPE: DNA
<213> ORGANISM: Artificial sequence
<220> FEATURE:
<223> OTHER INFORMATION: Artificially synthesized

<400> SEQUENCE: 12
ttatattgaa ttttcaaaaa ttcttacttt ttttttggat ggacgcaaag aagtttaata      60
atcatattac atggcattac caccatatac atatccatat ctaatcttac ttatatgttg     120
tggaaatgta aagagcccca ttatcttagc ctaaaaaaac cttctctttg gaactttcag     180
taatacgctt aactgctcat tgctatattg aagtacggat tagaagccgc cgagtttgcg     240
acagcccttt tacggaagac tctcctccgt gcgtcctcgt cttcaccggt cgcgttcctg     300
aaacgcagat gtgcctcgcg ccgcactgct ccgaacaata aagattctac aatactagct     360
tttatggtta tgaagaggaa aaattggcag taacctggcc ccacaaacct tcaaattaac     420
gaatcaaatt aacaaccata ggatgataat gcgattagtt ttttagcctt atttctgggg     480
taattaatca gcgaagcgat gatttttgat ctattaacag atatataaat ggaaaagctg     540
cataaccact ttaactaata ctttcaacat tttcagtttg tattacttct tattcaaatg     600
tcataaaagt atcaacaaaa aattgttaat atacctctat actttaacgt caaggagaaa     660
aaactata                                                              668

<210> SEQ ID NO 13
<211> LENGTH: 651
<212> TYPE: DNA
<213> ORGANISM: Artificial sequence
<220> FEATURE:
<223> OTHER INFORMATION: Artificially synthesized

<400> SEQUENCE: 13
ttatattgaa ttttcaaaaa ttcttacttt ttttttggat ggacgcaaag aagtttaata      60
atcatattac atggcattac caccatatac atatccatat ctaatcttac ttatatgttg     120
tggaaatgta aagagcccca ttatcttagc ctaaaaaaac cttctctttg gaactttcag     180
taatacgctt aactgctcat tgctatattg aagtacggat tagaagccgc cgagcgggcg     240
acagccctcc gatgcgtcct cgtcttcacc ggtcgcgttc ctgaaacgca gatgtgcctc     300
gcgccgcact gctccgaaca ataaagattc tacaatacta gcttttatgg ttatgaagag     360
gaaaaattgg cagtaacctg gccccacaaa ccttcaaatt aacgaatcaa attaacaacc     420
ataggatgat aatgcgatta gttttttagc cttatttctg ggtaattaa tcagcgaagc     480 gatgattttt gatctattaa cagatatata atggaaaag ctgcataacc actttaacta     540
atactttcaa cattttcagt ttgtattact tcttattcaa atgtcataaa agtatcaaca     600
aaaaattgtt aatatacctc tatactttaa cgtcaaggag aaaaaactat a              651

<210> SEQ ID NO 14
```

<211> LENGTH: 668
<212> TYPE: DNA
<213> ORGANISM: Artificial sequence
<220> FEATURE:
<223> OTHER INFORMATION: Artificially synthesized

<400> SEQUENCE: 14

| | | | | | | |
|---|---|---|---|---|---|---|
| ttatattgaa | ttttcaaaaa | ttcttacttt | tttttggat | ggacgcaaag | aagtttaata | 60 |
| atcatattac | atggcattac | caccatatac | atatccatat | ctaatcttac | ttatatgttg | 120 |
| tggaaatgta | aagagcccca | ttatcttagc | ctaaaaaaac | cttctctttg | gaactttcag | 180 |
| taatacgctt | aactgctcat | tgctatattg | aagtacggat | tagaagccgc | cgagcgggcg | 240 |
| acagccctcc | gaataaagac | tctccttatt | gcgtcctcgt | cttcaccggt | cgcgttcctg | 300 |
| aaacgcagat | gtgcctcgcg | ccgcactgct | ccgaacaata | aagattctac | aatactagct | 360 |
| tttatggtta | tgaagaggaa | aaattggcag | taacctggcc | ccacaaacct | tcaaattaac | 420 |
| gaatcaaatt | aacaaccata | ggatgataat | gcgattagtt | ttttagcctt | atttctgggg | 480 |
| taattaatca | gcgaagcgat | gattttgat | ctattaacag | atatataaat | ggaaaagctg | 540 |
| cataaccact | ttaactaata | ctttcaacat | tttcagtttg | tattacttct | tattcaaatg | 600 |
| tcataaaagt | atcaacaaaa | aattgttaat | atacctctat | actttaacgt | caaggagaaa | 660 |
| aaactata | | | | | | 668 |

<210> SEQ ID NO 15
<211> LENGTH: 634
<212> TYPE: DNA
<213> ORGANISM: Artificial sequence
<220> FEATURE:
<223> OTHER INFORMATION: Artificially synthesized

<400> SEQUENCE: 15

| | | | | | | |
|---|---|---|---|---|---|---|
| ttatattgaa | ttttcaaaaa | ttcttacttt | tttttggat | ggacgcaaag | aagtttaata | 60 |
| atcatattac | atggcattac | caccatatac | atatccatat | ctaatcttac | ttatatgttg | 120 |
| tggaaatgta | aagagcccca | ttatcttagc | ctaaaaaaac | cttctctttg | gaactttcag | 180 |
| taatacgctt | aactgctcat | tgctatattg | aagtaagcgg | gcgacagccc | tccgatgcgt | 240 |
| cctcgtcttc | accggtcgcg | ttcctgaaac | gcagatgtgc | ctcgcgccgc | actgctccga | 300 |
| acaataaaga | ttctacaata | ctagctttta | tggttatgaa | gaggaaaaat | tggcagtaac | 360 |
| ctggccccac | aaaccttcaa | attaacgaat | caaattaaca | accataggat | gataatgcga | 420 |
| ttagtttttt | agccttattt | ctggggtaat | taatcagcga | agcgatgatt | tttgatctat | 480 |
| taacagatat | ataaatggaa | aagctgcata | accactttaa | ctaatactttt | caacattttc | 540 |
| agtttgtatt | acttcttatt | caaatgtcat | aaaagtatca | acaaaaaatt | gttaatatac | 600 |
| ctctatactt | taacgtcaag | gagaaaaaac | tata | | | 634 |

<210> SEQ ID NO 16
<211> LENGTH: 668
<212> TYPE: DNA
<213> ORGANISM: Artificial sequence
<220> FEATURE:
<223> OTHER INFORMATION: Artificially synthesized

<400> SEQUENCE: 16

| | | | | | | |
|---|---|---|---|---|---|---|
| ttatattgaa | ttttcaaaaa | ttcttacttt | tttttggat | ggacgcaaag | aagtttaata | 60 |
| atcatattac | atggcattac | caccatatac | atatccatat | ctaatcttac | ttatatgttg | 120 |
| tggaaatgta | aagagcccca | ttatcttagc | ctaaaaaaac | cttctctttg | gaactttcag | 180 |

```
taatacgctt aactgctcat tgctatattg aagtatctat tagaagccga aaagcgggcg    240
acagccctcc gaataaagac tctccttatt gcgtcctcgt cttcaccggt cgcgttcctg    300
aaacgcagat gtgcctcgcg ccgcactgct ccgaacaata aagattctac aatactagct    360
tttatggtta tgaagaggaa aaattggcag taacctggcc ccacaaacct tcaaattaac    420
gaatcaaatt aacaaccata ggatgataat gcgattagtt ttttagcctt atttctgggg    480
taattaatca gcgaagcgat gattttgat ctattaacag atatataaat ggaaaagctg    540
cataaccact ttaactaata ctttcaacat tttcagtttg tattacttct tattcaaatg    600
tcataaaagt atcaacaaaa aattgttaat atacctctat actttaacgt caaggagaaa    660
aaactata                                                              668
```

<210> SEQ ID NO 17
<211> LENGTH: 633
<212> TYPE: DNA
<213> ORGANISM: Artificial sequence
<220> FEATURE:
<223> OTHER INFORMATION: Artificially synthesized

<400> SEQUENCE: 17

```
ttatattgaa ttttcaaaaa ttcttacttt tttttggat ggacgcaaag aagtttaata     60
atcatattac atggcattac caccatatac atatccatat ctaatcttac ttatatgttg    120
tggaaatgta aagagcccca ttatcttagc ctaaaaaaac cttctctttg gaactttcag    180
taatacgctt aactgctcat tgctatattg aagtacggat tagaagccgc cgagtgcgtc    240
ctcgtcttca ccggtcgcgt tcctgaaacg cagatgtgcc tcgcgccgca ctgctccgaa    300
caataaagat tctacaatac tagctttat ggttatgaag aggaaaaatt ggcagtaacc    360
tggccccaca aaccttcaaa ttaacgaatc aaattaacaa ccataggatg ataatgcgat    420 tagttttta gccttatttc tggggtaatt aatcagcgaa gcgatgattt ttgatctatt    480
aacagatata taaatggaaa agctgcataa ccactttaac taatactttc aacattttca    540
gtttgtatta cttcttattc aaatgtcata aaagtatcaa caaaaaattg ttaatatacc    600
tctatacttt aacgtcaagg agaaaaaact ata                                 633
```

<210> SEQ ID NO 18
<211> LENGTH: 668
<212> TYPE: DNA
<213> ORGANISM: Artificial sequence
<220> FEATURE:
<223> OTHER INFORMATION: Artificially synthesized

<400> SEQUENCE: 18

```
ttatattgaa ttttcaaaaa ttcttacttt tttttggat ggacgcaaag aagtttaata     60
atcatattac atggcattac caccatatac atatccatat ctaatcttac ttatatgttg    120
tggaaatgta aagagcccca ttatcttagc ctaaaaaaac cttctctttg gaactttcag    180
taatacgctt aactgctcat tgctatattg aagtacggat tagaagccgc cgagtttgcg    240
acagcccttt aataaagac tctccttatt gcgtcctcgt cttcaccggt cgcgttcctg    300
aaacgcagat gtgcctcgcg ccgcactgct ccgaacaata aagattctac aatactagct    360
tttatggtta tgaagaggaa aaattggcag taacctggcc ccacaaacct tcaaattaac    420
gaatcaaatt aacaaccata ggatgataat gcgattagtt ttttagcctt atttctgggg    480
taattaatca gcgaagcgat gattttgat ctattaacag atatataaat ggaaaagctg    540
```

| cataaccact ttaactaata ctttcaacat tttcagtttg tattacttct tattcaaatg | 600 |
| tcataaaagt atcaacaaaa aattgttaat atacctctat actttaacgt caaggagaaa | 660 |
| aaactata | 668 |

<210> SEQ ID NO 19
<211> LENGTH: 972
<212> TYPE: DNA
<213> ORGANISM: Artificial sequence
<220> FEATURE:
<223> OTHER INFORMATION: Artificially synthesized

<400> SEQUENCE: 19

| ttatattgaa ttttcaaaaa ttcttacttt ttttttggat ggacgcaaag aagtttaata | 60 |
| atcatattac atggcattac caccatatac atatccatat ctaatcttac ttatatgttg | 120 |
| tggaaatgta aagagcccca ttatcttagc ctaaaaaaac cttctctttg gaactttcag | 180 |
| taatacgctt aactgctcat tgctatattg aagtatctat tagaagccga aaagtttgcg | 240 |
| acagcccttt tacggaagac tctcctccgt gcgtcctcgt cttcaccggt cgcgttcctg | 300 |
| aaacgcagat gtgcctcgcg ccgcactgct ccgaacaata aagattctac aatactagct | 360 |
| tttatggtta tgaagaggaa aaattggcag taacctggcc ccacaaacct tcaaattaac | 420 |
| gaatcaaatt aacaaccata ggatgataat gcgattagtt ttttagcctt atttctgggg | 480 |
| taattaatca gcgaagcgat gattttttgat ctattaacag atatataaat ggaaaagctg | 540 |
| cataaccact ttaactaata ctttcaacat tttcagtttg tattacttct tattcaaatg | 600 |
| tcataaaagt atcaacaaaa aattgttaat atacctctat actttaacgt caaggagaaa | 660 |
| aaactataat ggcgcaagtt ttccgctttg taatatatat ttatacccct ttcttctctc | 720 |
| ccctgcaata taatagttta attctaatat taataatatc ctatatttc ttcatttact | 780 |
| acggattaga agccgccgag cggcgcactc tcgcccgaac gacctcaaaa tgtctgctac | 840 |
| attcataata accaaaagct cataactttt tttttttgaac ctgaatatat atacatcaca | 900 |
| tatcactgct ggtccttgcc gaccagcgta tacaatctcg atagttggtt tcccgttctt | 960 |
| tccactcccg tc | 972 |

<210> SEQ ID NO 20
<211> LENGTH: 388
<212> TYPE: DNA
<213> ORGANISM: Artificial sequence
<220> FEATURE:
<223> OTHER INFORMATION: Artificially synthesized
<220> FEATURE:
<221> NAME/KEY: misc_feature
<222> LOCATION: (270)..(289)
<223> OTHER INFORMATION: n is a, c, g, or t

<400> SEQUENCE: 20

| tctttgaaaa gataatgtat gattatgctt tcactcatat ttatacagaa acttgatgtt | 60 |
| ttctttcgag tatatacaag gtgattacat gtacgtttga agtacaactc tagattttgt | 120 |
| agtgccctct tgggctagcg gtaaaggtgc gcatttttc acaccctaca atgttctgtt | 180 |
| caaaagattt tggtcaaacg ctgtagaagt gaaagttggt gcgcatgttt cggcgttcga | 240 |
| aacttctccg cagtgaaaga taaatgatcn nnnnnnnnnn nnnnnnnnng ttttagagct | 300 |
| agaaatagca agttaaaata aggctagtcc gttatcaact tgaaaagtg gcaccgagtc | 360 |
| ggtggtgctt tttttgtttt ttatgtct | 388 |

```
<210> SEQ ID NO 21
<211> LENGTH: 643
<212> TYPE: DNA
<213> ORGANISM: Artificial sequence
<220> FEATURE:
<223> OTHER INFORMATION: Artificially synthesized

<400> SEQUENCE: 21
ttatattgaa ttttcaaaaa ttcttacttt ttttttggat ggacgcaaag aagtttaata    60
atcatattac atggcattac caccatatac atatccatat ctaatcttac ttatatgttg   120
tggaaatgta aagagcccca ttatcttagc ctaaaaaaac cttctctttg gaactttcag   180
taatacgctt aactgctcat tgctatattg aagtacggat tagaagccgc cgagcgggcg   240
acagccctcc gacggaagac tctcctccgt gcgtcctcgt cttaccggt cgcgttcctg    300 aaacgcagat gtgcaaagat ctacaaatac tagcttttat ggttatgaag aggaaaaatt   360
ggcagtaacc tggccccaca aaccttcaaa ttaacgaatc aaattaacaa ccataggatg   420
ataatgcgat tagttttta gccttatttc tggggtaatt aatcagcgaa gcgatgattt    480
ttgatctatt aacagatata taaatggaaa agctgcataa ccactttaac taatactttc   540
aacattttca gtttgtatta cttcttattc aaatgtcata aaagtatcaa caaaaaattg   600
ttaatatacc tctatacttt aacgtcaagg agaaaaaact ata                     643

<210> SEQ ID NO 22
<211> LENGTH: 668
<212> TYPE: DNA
<213> ORGANISM: Artificial sequence
<220> FEATURE:
<223> OTHER INFORMATION: Artificially synthesized

<400> SEQUENCE: 22
ttatattgaa ttttcaaaaa ttcttacttt ttttttggat ggacgcaaag aagtttaata    60
atcatattac atggcattac caccatatac atatccatat ctaatcttac ttatatgttg   120
tggaaatgta aagagcccca ttatcttagc ctaaaaaaac cttctctttg gaactttcag   180
taatacgctt aactgctcat tgctatattg aagtacggat tagaagccgc cgagcgggcg   240
acagccctcc gacggaagac tctcctccgt gcgtcctcgt cttaccggt cgcgttcctg    300 aaacgcagat gtgcctcgcg ccgcactgct ccgaacaata aagattctac aatactagct   360
tttatggtta tgaagaggaa aaattggcag taacctggcc ccacaaacct tcaaattaac   420
gaatcaaatt aacaaccata ggatgataat gcgattagtt ttttagcctt atttctgggg   480
taattaatca gcgaagcgat gattttgat ctattaacag atatataaat ggaaaagctg    540
cataaccact ttaactaata ctttcaacat tttcagtttg tattacttct tattcaaatg   600
tcataaaagt atcaacaaaa aattgttaat atacctctat actttaacgt caaggagaaa   660
aaactata                                                            668

<210> SEQ ID NO 23
<211> LENGTH: 668
<212> TYPE: DNA
<213> ORGANISM: Artificial sequence
<220> FEATURE:
<223> OTHER INFORMATION: Artificially synthesized

<400> SEQUENCE: 23
ttatattgaa ttttcaaaaa ttcttacttt ttttttggat ggacgcaaag aagtttaata    60
atcatattac atggcattac caccatatac atatccatat ctaatcttac ttatatgttg   120
```

```
tggaaatgta aagagcccca ttatcttagc ctaaaaaaac cttctctttg gaactttcag    180
taatacgctt aactgctcat tgctatattg aagtatgcgt tctattagaa gccgaaaagt    240
ttgcgacagc cctttttacgg aagactctcc tccgcctcgt cttcaccggt cgcgttcctg   300
aaacgcagat gtgcctcgcg ccgcactgct ccgaacaata aagattctac aatactagct    360
tttatggtta tgaagaggaa aaattggcag taacctggcc ccacaaacct tcaaattaac    420
gaatcaaatt aacaaccata ggatgataat gcgattagtt ttttagcctt atttctgggg    480
taattaatca gcgaagcgat gatttttgat ctattaacag atatataaat ggaaaagctg    540
cataaccact ttaactaata ctttcaacat tttcagtttg tattacttct tattcaaatg    600
tcataaaagt atcaacaaaa aattgttaat atacctctat actttaacgt caaggagaaa    660
aaactata                                                             668
```

<210> SEQ ID NO 24
<211> LENGTH: 668
<212> TYPE: DNA
<213> ORGANISM: Artificial sequence
<220> FEATURE:
<223> OTHER INFORMATION: Artificially synthesized

<400> SEQUENCE: 24

```
ttatattgaa ttttcaaaaa ttcttacttt tttttttggat ggacgcaaag aagtttaata    60
atcatattac atggcattac caccatatac atatccatat ctaatcttac ttatatgttg   120
tggaaatgta aagagcccca ttatcttagc ctaaaaaaac cttctctttg gaactttcag   180
taatacgctt aactgctcat tgctatattg aagtatgcgt cctcgtctat tagaagccga   240
aaagtttgcg acagcccttt tacggaagac tctcctccgt cttcaccggt cgcgttcctg   300
aaacgcagat gtgcctcgcg ccgcactgct ccgaacaata aagattctac aatactagct   360
tttatggtta tgaagaggaa aaattggcag taacctggcc ccacaaacct tcaaattaac   420
gaatcaaatt aacaaccata ggatgataat gcgattagtt ttttagcctt atttctgggg   480
taattaatca gcgaagcgat gatttttgat ctattaacag atatataaat ggaaaagctg   540
cataaccact ttaactaata ctttcaacat tttcagtttg tattacttct tattcaaatg   600
tcataaaagt atcaacaaaa aattgttaat atacctctat actttaacgt caaggagaaa   660
aaactata                                                            668
```

<210> SEQ ID NO 25
<211> LENGTH: 668
<212> TYPE: DNA
<213> ORGANISM: Artificial sequence
<220> FEATURE:
<223> OTHER INFORMATION: Artificially synthesized

<400> SEQUENCE: 25

```
ttatattgaa ttttcaaaaa ttcttacttt tttttttggat ggacgcaaag aagtttaata    60
atcatattac atggcattac caccatatac atatccatat ctaatcttac ttatatgttg   120
tggaaatgta aagagcccca ttatcttagc ctaaaaaaac cttctctttg gaactttcag   180
taatacgctt aactgctcat tgctatattg aagtatgcgt cctcgtcttc actctattag   240
aagccgaaaa gtttgcgaca gccctttac ggaagactct cctccgcggt cgcgttcctg    300
aaacgcagat gtgcctcgcg ccgcactgct ccgaacaata aagattctac aatactagct   360
tttatggtta tgaagaggaa aaattggcag taacctggcc ccacaaacct tcaaattaac   420
gaatcaaatt aacaaccata ggatgataat gcgattagtt ttttagcctt atttctgggg   480
```

```
taattaatca gcgaagcgat gatttttgat ctattaacag atatataaat ggaaaagctg    540
cataaccact ttaactaata ctttcaacat tttcagtttg tattacttct tattcaaatg    600
tcataaaagt atcaacaaaa aattgttaat atacctctat actttaacgt caaggagaaa    660
aaactata                                                              668

<210> SEQ ID NO 26
<211> LENGTH: 17
<212> TYPE: DNA
<213> ORGANISM: Artificial sequence
<220> FEATURE:
<223> OTHER INFORMATION: Artificially synthesized
<220> FEATURE:
<221> NAME/KEY: misc_feature
<222> LOCATION: (4)..(14)
<223> OTHER INFORMATION: n is a, c, g, or t

<400> SEQUENCE: 26
cggnnnnnnn nnnnccg                                                    17

<210> SEQ ID NO 27
<211> LENGTH: 25
<212> TYPE: DNA
<213> ORGANISM: Artificial sequence
<220> FEATURE:
<223> OTHER INFORMATION: Artificially synthesized
<220> FEATURE:
<221> NAME/KEY: misc_feature
<222> LOCATION: (6)..(16)
<223> OTHER INFORMATION: n is a, c, g, or t

<400> SEQUENCE: 27
ctcgcnnnnn nnnnnnccga acaat                                           25
```